United States Patent
Wu et al.

(10) Patent No.: US 6,888,047 B1
(45) Date of Patent: May 3, 2005

(54) TRANSGENIC ANIMALS AS URINARY BIOREACTORS FOR THE PRODUCTION OF POLYPEPTIDE IN THE URINE, RECOMBINANT DNA CONSTRUCT FOR KIDNEY-SPECIFIC EXPRESSION, AND METHOD OF USING SAME

(75) Inventors: Xue-Ru Wu, Staten Island, NY (US); Tung-Tien Sun, Scarsdale, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/605,042

(22) Filed: Jun. 26, 2000

Related U.S. Application Data

(63) Continuation-in-part of application No. 09/438,785, filed on Nov. 12, 1999, now abandoned.
(60) Provisional application No. 60/142,925, filed on Jul. 9, 1999, and provisional application No. 60/108,195, filed on Nov. 13, 1998.

(51) Int. Cl.$^7$ ............................................. A01K 67/027
(52) U.S. Cl. ............................... 800/14; 800/4; 800/15; 800/16; 800/17; 800/18; 800/21; 800/25; 435/69.1; 435/320.1; 435/325; 435/455; 523/23.1; 523/23.5
(58) Field of Search .............................. 435/69.1, 320.1, 435/325, 455; 523/23.1, 23.5; 800/4, 14, 15, 16, 17, 18, 21, 25; 536/23.1, 23.5

(56) References Cited

U.S. PATENT DOCUMENTS

| | | | | |
|---|---|---|---|---|
| 5,824,543 A | 10/1998 | Sun | .......................... | 453/320.1 |
| 6,001,646 A | 12/1999 | Sun | .......................... | 435/320.1 |
| 6,339,183 B1 * | 1/2002 | Sun | .............................. | 800/14 |

FOREIGN PATENT DOCUMENTS

| | | |
|---|---|---|
| WO | 0 653 154 A2 | 3/1995 |
| WO | 99/28463 | 6/1999 |
| WO | 00/15772 | 3/2000 |

OTHER PUBLICATIONS

Wood. Phenotype Assesment: Are you missing something? Comp. Med. 50(1): 12–15, 2000.*
Sigmund, Viewpoint: Are studies in genetically altered mice out of control? Arterioscler. Throm. Vasc. Biol. 20:1425–1429, 2000.*
Su et al Uromodulin and Tamm–horsfall protein induce human monocytes to secrete TNFa nd express tissue factor. J Immunolgy 158:3449–3436, 1997.*
Pursel VG et al, Expression and performance in transgenic pigs. J. Reprod. Fert. Sup 40: 235–245 1990.*
Lin J et al A tissue–specific promoter that can drive a foreign gene to express in the suprabasal urothelial cells of transgenic mice.PNAS 92:679–683, 1995.*
Zbikowska et al Uromodulin promoter directs high–level expression of biologically active human a1–antitypsin into mouse urine Biochem J 365:7–11, 2002.*
Jeanpierre et al., Chromosomal assignment of the uromodulin gene (UMOD) to 16p13.11, *Cytogenet Cell Genet* 62: 185–187 (1993).
Kappel et al., Regulating gene expression in transgenic animals, *Current Opinion in Biotechnology* 3:548–553 (1992).
Kerr et al., The bladder as a bioreactor: Urothelium production and secretion of growth hormone into urine, *Nature Biotechnology* 16:75–79 (1998).
Su et al., Uromodulin and Tamm–Horsfall protein induce human monocytes to secrete TNF and express tissue factor, *The American Association of Immunologists* 3449–3456 (1997).
Viville, Mouse genetic manipulation via homologous recombination, *Transgenic Animals: Generation and Use* 307–321 (1997).
Wall, Transgenic livestock: progress and prospects for the future, *Theriogenology* 45:57–68 (1996).
Zhong–Ting et al., Urothelium–specific expression of an oncogene in transgenic mice induced the formation of carcinoma in Situ and invasive transitional cell carcinoma, *Cancer Research* 59:3512–3517 (1999).
Yu et al., Bovine and rodent Tamm–Horsfall protein (THP) genes: Cloning, structural analysis, and promoter identification, *Gene Expression* 4:63–75 (1994).

* cited by examiner

*Primary Examiner*—Jeffrey Fredman
*Assistant Examiner*—Sumesh Kaushal
(74) *Attorney, Agent, or Firm*—Browdy and Neimark, PLLC

(57) ABSTRACT

The invention relates to recombinant DNA constructs, a method for producing a recombinant biologically active protein in vivo in the urine of a non-human mammal using a kidney-specific promoter, such as the uromodulin promoter, and the transgenic non-human mammals that serve as urine-based bioreactors for protein production.

26 Claims, 26 Drawing Sheets

```
         1
   Rat   ...MGQLLSL TWLLLVMVVT PWFTVAGAND SPEARRCSEC HDNATCVLDG
 Mouse   ...MG..IPL TWMLLVMVVT SWFTLAGASN STEARRCSEC HDNATCTVDG
 Human   ...MGQP.SL TWMLMV.VVA SWFITTAATD TSEARWCSEC HSNATCTEDE
Bovine   MKCLFSP.NF MWM.AA.VVT SWVIIPAATD TSSAKSCSEC HSNATCTVDG
         51                              *                100
   Rat   VVTTCSCQAG FTGDGLVCED IDECATPWTH NCS.NSICMN TLGSYECSCQ
 Mouse   VVTTCSCQTG FTGDGLVCED MDECATPWTH NCS.NSSCVN TPGSFKCSCQ
 Human   AVTTCTCQEG FTGDGLTCVD LDECAIPGAH NCSANSSCVN TPGSFSCVCP
Bovine   AATTCACQEG FTGDGLECVD LDECAVLGAH NCSATKSCVN TLGSYTCVCP
         101                                               150
   Rat   DGFRLTPGLG CIDVNECTEQ GLSNCHSLAT CVNTEGSYSC VCPKGYRGDG
 Mouse   DGFRLTPGLG CTDVDECSEQ GLSNCHALAT CVNTEGDYLC VCPKGFTGDG
 Human   EGFRLSPGLG CTDVDECAEP GLSHCHALAT CVNVVGSYLC VCPAGYRGDG
Bovine   EGFLLSSELG CEDVDECAEP GLSRCHALAT CINGEGNYSC VCPAGYLGDG
         151                                               200
   Rat   WYCECSPGFC EPGLDCLPQG PSGKLVCQDP CNVYETLTEY WRSTDYGAGY
 Mouse   WYCECSPSSC EPGLDCLPQG PDGKLVCQDP CNTYETLTEY WRSTEYGVGY
 Human   WHCECSPGSC GPGLDCVPEG ..DALVCADP CQAHRTLDEY WRSTEYGEGY
Bovine   RHCECSPGSC GPGLDCVREG ..DALVCVDP CQVHRILDEY WRSTEYGSGY
         201                           *                  250
   Rat   SCDSDMHGWY RFTGQGGVRM AETCVPVLRC NTAAPMWLNG SHPSSREGIV
 Mouse   SCDAGQHGWY RFTGQGGVRM AETCVPVLAC NTAAPMWLNG SHPSSSEGIV
 Human   ACDTDLRGWY RFVGQGGARM AETCVPVLRC NTAAPMWLNG THPSSDEGIV
Bovine   ICDVSLGGWY RFVGQAGVRL PETCVPVLHC NTAAPMWLNG THPSSDEGIV
         251                        *                      300
   Rat   SRTACAHWSD HCCLWSTEIQ VKACPGGFYV YNLTEPPECN LAYCTDPSSV
 Mouse   SRTACAHWSD HCCRWSTEIQ VKACPGGFYI YNLTEPPECN LAYCTDPSSV
 Human   SRKACAHWSG HCCLWDASVQ VKACAGGYYV YNLTAPPECH LAYCTDPSSV
Bovine   NRVACAHWSG DCCLWDAPIQ VKACAGGYYV YNLTAPPECH LAYCTDPSSV
         301                        *                      350
   Rat   EGTCEECGVD EDCVSDNGRW RCQCKQDFNV TDVSLLEHRL ECEANEIKIS
 Mouse   EGTCEECRVD EDCISDNGRW RCQCKQDSNI TDVSQLEYRL ECGANDIKMS
 Human   EGTCEECSID EDCKSNNGRW HCQCKQDFNI TDISLLEHRL ECGANDMKVS
Bovine   EGTCEECRVD EDCKSDNGEW HCQCKQDFNV TDLSLLERRL ECGVDDIKLS
         351                                               400
   Rat   LSKCQLQSLG FMKVFMYLND RQCSGFSERG ERDWMSIVTP ARDGPCGTVL
 Mouse   LRKCQLQSLG FMNVFMYLND RQCSGFSESD ERDWMSIVTP ARNGPCGTVL
 Human   LGKCQLKSLG FDKVFMYLSD SRCSGFNDRD NRDWVSVVTP ARDGPCGTVL
Bovine   LSKCQLKSLG FEKVFMYLHD SQCSGFTERG DRDWMSVVTP ARDGPCGTVM
         401*                                              450
   Rat   RFNETHATYS NTLYLASEII IRDINIRINF ECSYPLDMKV SLKTSLQPMV
 Mouse   RFNETHATYS NTLYLANAII IRDIIIRMNF ECSYPLDMKV SLKTSLQPMV
 Human   TFNETHATYS NTLYLADEII IRDLNIKINF ACSYPLDMKV SLKTALQPMV
Bovine   TFNETHATYS NTLYLADEII IRDLNIRINF ACSYPLDMKV SLKTSLQPMV
         451                                               500
   Rat   SALNISLGGT GKFTVQMALF QNPTYTQPYQ GPSVMLSTEA FLYVGTMLDG
 Mouse   SALNISLGGT GKFTVRMALF QSPTYTQPYQ GPSVMLSTEA FLYVGTMLDG
 Human   SALNIRVGGT GMFTVRMALF QTPSYTQPYQ GSSVTLSTEA FLYVGTMLDG
Bovine   SALNISMGGT GTFTVRMALF QSPAYTQPYQ GSSVTLSTEA FLYVGTMLDG
         501                *                              550
   Rat   GDLSRFVLLM TNCYATPSSN STDPVKYFII QDRCPHTEDT TIQVTENGES
 Mouse   GDLSRFVLLM TNCYATPSSN STDPVKYFII QDSCPRTEDT TIQVTENGES
 Human   GDLSRFALLM TNCYATPSSN ATDPLKYFII QDRCPHTRDS TIQVVENGES
Bovine   GDLSRFVLLM TNCYATPSSN ATDPLKYFII QDRCPRAADS TIQVEENGES
         551                                               600
   Rat   SQARFSIQMF RFAGNSDLVY LHCEVYLCDT MSEQCKPTCS GTRYRSGNFI
 Mouse   SQARFSVQMF RFAGNYDLVY LHCEVYLCDS TSEQCKPTCS GTRFRCGNFI
 Human   SQGRFSVQMF RFAGNYDLVY LHCEVYLCDT MNEKCKPTCS GTRFRSGSVI
Bovine   PQGRFSVQMF RFAGNYDLVY LHCEVYLCDT VNEKCRPTCP ETRFRSGSII
         601                                          648
   Rat   DQTRVLNLGP ITRQGVQASV SKAASSNLGF LSIWLLLFLS ATLTLMVH
 Mouse   DQTRVLNLGP ITRQGVQASV SKAASSNLRL LSIWLLLFLS ATLIFMVQ
 Human   DQSRVLNLGP ITRKGVQATV SRAF.SSLGL LKVWLPLLLS ATLTLTFQ
Bovine   DQTRVLNLGP ITRKGGQAAM SRAAPSSLGL LQVWLPLLLS ATLTLMSP
```

FIG. 3

```
   1 GGGG/GGGCCC TCGGGAGTTT GGCTAAGTCT TGCAAATGAG CTGTGATGAC
     polycloning site of pBS
  51 AGGTTTGCGC CATATGAGAT CCAGTGACAA GCTCATCTCT AGATGTCTGC
 101 ATACCAATAA GTGACCCATC ATTATGCAAT CAGGCCGGAC TCATCCTCTG
 151 TGGCTTTGTC TCTTACTACT GTAAACTTGA TAACCTATAT GATTTTACCC
 201 ATTTCCCCTC CATGGCACTC AACTCCTC   TTCCTATGTG ACCCTACTTA
 251 TGTCCTATGT GACTCCAGCT GCTTCCTTTG ATGAGAGCCA TCCTGTTCTT
     JP.S3
 301 TCTATGTGAC TCTGCTCACT TCTTCCACGT GACTCCACCA ATCTGTCTAC
 351 ATTGCAGAGT CACTCACAGT TTCTTGAGAG CAGAAGACTC AGAACTGATC
 401 TGTCCTCAAT GTCCTCCCTA CACTTTCTCC TCATAATCCA CATATCTAAA
 451 GCTATAGAGA TAATTTCATG CACTATAGCT TTCAGTACTA TCGTATCTAC
 501 TGTCTCTACC CTGTAACTGG TATCTTCATG ACATCTCGAA TATTTCCAAT
 551 TTCTCTATTG CTGCAAAGTC TTGAGAAGTC TAGTCTTATG GATCTCCTTT
 601 TCTCCTCAGG TCTCCTGGTC TCCACACACC ATTCACACTT CTTGAATATT
     JP.S4
 651 CTTTGAACAT AACAAATTCT CTCCATGGGT TTGTTCCCTC TACCCAAATT
 701 CATGCCTTCA GGATACTTAC TCTGCCCCAT CTTCACTCAT CTCTGCTTTG
 751 GTCATTCAAA TCTCAAATGT AGCCATTTCT AAAAGGCTCT CCAAGAGAAT
 801 AATATTTGAA AGCATTTTGC TATTCTATCA AGTGATCATA CAATGTCTGC
 851 TCCTGCCACC ACCATGACCA TCCCCATGAA TACAGACACT GCCTTCTTAG
     JP.S5
 901 TGTTTGCTGT ATGTGTTCTG TGTGGTACAT TGTAGATAAA TGCTGTAATA
 951 AACATCTGTG GAGCAAATTG AATCATCAGA TAGCACCCTC TCTCTGAGAG
1001 GCATGATCTC ATGGTTATCC CCAAAGCATG AGGTAAGGAC ATTATCCCAG
1051 GTCCATGCTG GTTTCCGTAT TGATTGTTTC TAACACAAAC TTAATAGATT
1101 AAAACAGCAC GGATTTATTC TCACATGTTT TGAGACGCCA GAAATCTGAC
```

FIG.10A

```
1151  ACCAGTTTCA ATGTTTAGAC TTGATGCACA CCTGTAATTC TGGTACTTAG
1201  GAGGCAGATG CAGGGGGACT ATGATTTAAA GCCCATTTTT AAGCTGCTGG
1251  GTGAGAACCT GTCTTGATTT TTTTTTCACA TTGGGCTAAA AGTCAAGGAT
1301  CATCAGGGTT GGTGCATTCT GGAAGAAACC TTTGCCTTGC AGCTTCCAG
1351  AGGGCCGCCA GCATTCCTTG CTTGTGTTT GGTCCTGGAA TCACTGTGAC
1401  CTTATGCTCC ATCCTCACAT TCCCTCTGCA TTTATCCTCT AAGCACCGGT
                                                    JP.S6
1451  GTGCTTGTAT CCAACCTTTA GGAGCCCCAT AGATCCCCCA TTTCTCCTCG
1501  ACTTAATCAC ACCTGTATAA GTACTTTCA CTCTGCAAAG CAATATTTGT
1551  GGGTCCAAGG GATTAGGATG TGGGTATATT TGTGGGTGT CATTATTCAA
1601  TGCTTCATAT TTACACTGTT TCTCTGTTTC ACTTTATTGG GGTACTTGAA
1651  CTTCTAAGAA GAACTGAGGG GTATTGTTGT AGGAACTAAA TTCCCCCATG
1701  GACCTCTGTG CTTTCCACCT ATCACACAAG ACAGAGGGTA TTTGTATTTT
1751  TAGATCCCCA GAAGAAATTC CCACTCTCAA CCCTCCATCC CTGACTTGCT
1801  CACATCTAGA TGAAGCAGGG AACAGCCTGA GNCCTGGAAC TCACTGGAGC
1851  CAGATGACTC TATGGAGTTA GGTTTTAGTA TTCAAGACAC GATGCAAGAC
1901  TCACCTGCCT TCCCCTCACA GACATGTGGC TGCCTGTCAA AGGTGGGGCC
1951  ATGGGGCTGC TGAGACTAAG TCACGTGGAC AGCGCCCATG ACAAGCAGTG
      JP.S7
2001  ACATGGAGAC CAAGGCTGCA GTGTGCATGC TCCACAGGTG CACCTGAAGC
2051  CTCAGAGACG GGAAGAGGAG AGGGAGCAGA AAGATGGGGT ACAGATACCC
2101  CTCTGTTAGG AAGGGCTTCA AAACCGTCTT CTAAGTTTTT GATCCTTTTA
2151  AATGTATCCA CCTGTCACTT GACCCTCTCC TGCTCTGTCT GATCAGCTTC
2201  TCAAAACCCT TCATCCCCTT AACTCCACCC TACTGAAAAA AGATGAAACC
2251  ACTTGTCAAT ATAAACCTCA ACAGCTAAGC ATGGAATACT GTTAACCCCT
2301  CAAGACATAA AGCTGACTGA AGGGATAAGT TTGAAAAAAA TGGGCTTCAG
2351  TTTGCACTAG CTAAGTATGT AACCTTGAAG ATATTACTCA GTTTCTCTGA
2401  ACTTCAGTCT GCTCTCCTAT TTATTGACAA CATGTAAGAG CACATACCGG
2451  GCATTTCTTG TCACCAAATG AAGTTTCCAG TACCAGGAAT GGGTTATATC
```

FIG.10B

2501 TAATCGAGTT GTTGGCCAAA GGAGTTCCAT GGAAACTCCC AAACAATCCA
2551 GGCTATTGGC AAGACTTTTG ATGTCTCTCC ACAAACTGAC AGCAACTGTT
2601 GAAAGACAAT ACCTACACAG CTCACTGAAC ACAGAGAAGC TGAGTTGGTG
2651 CCTACATAAA TCCTCTAGCT CTATGAAGGT CCATAATGGT ATTCATGGCC
2701 CTAGAAGATA CTCTTCCCTC CACCAAAGGA GAAATGTAAA CACTAAGCCA
2751 GCCATAAACC CTTTGGTCTG TTAGAGTGGC CTGCCTGCAA GTTCTGCTGG
2801 TGTAATAATG GCACAGAGCT TGTAGGAGTA ACCAAACAAT ATCTGATAGG
2851 TTAAGGCCCA CTCCATGAGA TCAAACCCAG ACCTAACAAC ACTTGGGTGG
2901 ATGAGAACCC GAGACCAGAT AGGCCAGGGA CCTATGGGAA AACTAAACAT
2951 GACTGTTCTG CTAAAAGAAC CTACCAATAA AATAGCTCCT AGTGACATTC
3001 TGCCATATTT <u>ATAGATCAGT TCCTTGTTCA</u> TCCATCATCA GAAAACTTCC
                      JP.AS14
3051 TCTTCAGTAG ATAGAAACAA ATATAGAGCC CACAGCCAGA TAATATCCAG
3101 AGAGTGAGAT ACCCTGGAAC ACTCAGCTCT AAAAGGGATG TCTCCATCAA
3151 CCCCCCCCCC CCCCACCTTT CAGGACTCAT GAAACCCTCC AGAAGACGAG
3201 TCAGAAAGAG TGTAAGATCC AGAAGGGATG GAGGACATCC AAAACTTAAG
3251 GCCTTCAAGA CACAACTGTA AGGGAACACA TATGAACTTA GAGAGATGGT
3301 GCAGCATGCA CAGAGCCTGC ATGGGCTTGT ACCAGATGGG GTTCTAGAGC
3351 TGAAAGGAGA AATGGATAGC CACTCTGATT CCTAACCCAG AAGTGACCCC
3401 TAACTGATAG TGACTTGCAA ATAAAAAATT AGTCTTTTTT CAAAGGGAGT
3451 CTCACTGGGA AAATAAACCA CTCTAAATAG TAGACCCCAT GCCCAGCAGT
3501 AGATGGCCAA CAGAAAATGA ACTCAATGTC ATCTTTGACC TTCCTTTGTC
3551 GGAAAGCTTT TTGTTTGCTT <u>TTTCTTACCC TACAGGTCCT</u> TTGCATATTT
                                   JP.AS13
3601 ATTATGGTTT CTTGTTTCAG GTTTTAATG GAACTCCTGA GTGTGTGAAT
3651 GTGTGTGTCT CTGCATACAT GTGTGTTTCT TAAGCCCGTT CTTTTTCTTT
3701 TCTTCTCTTT ATTGTTTAAA AAACAATTG TTCTTTATTT TATTATTATT
3751 CCTTATTTTA GACAGAAACA TTGTGGATCC AGATGGGAGA AGAGGTTGGA
3801 GGAATTGGGA GGAGTAAAGG GACAGAAACC ATAATCAGGG GGAACCATAA

FIG. 10C

```
3851  TCAGGGAGAA CCATAATCAG GGGGAGCCAT AATCAGGGGG AGCCATAATC
3901  CAAGGGAACC ATAATCAGAA TATACTGTAT GAAAAAAATT CTATTTTCAA
3951  TAAAAAAAGA ATAAAAAAAA AACAGTCTGA CTGAAGAATA GCACTTGGTA
4001  AGTAACTCTT GTTATAACAA TCCATATCAA ATGCCCTGCC TGTGTTAGCA
4051  AGTTAAGAGA AAAGATTATT CCAAGAGATC CAAGTCTCCT TCAAAACCAA
                                     ZT.S1
4101  GTGTGTACAG AACATTGTCT GAGGAGTAAG ATTGCATTTG CAACATGCA
4151  TGTCTTTAAT GGTGTGGAGA ATTTCAGTGG AGTTGGCACG TCAGAAAGCA
                                     JP.AS12
4201  CACTGGTGAA AAATGGAGAG AATAGATATA TCCTTTGAGA AATTTGGTCT
4251  CAAAAAGTAG GGTATCAAAT TACTTGGTGT CTGTGAGATC AATTGGTTGT
4301  CTCTGTAGGT TAGCTTACAT AGGAGACAGG AATAAGTGAA GGAGAGAAGG
4351  GAGGACATTG GAGCACCCAA GGAGAGAGGG ACCTTCCTCC TAAAAGTGAA
4401  TGAGGTGGCC TTCATTCCAA GGAGAAGAGA TTCAGGTCGC CCGGGAAGAT
4451  GAGGGACCAA CATCCACAAG GAATGGCAGG AAGTCATCCT GTGTGCATAA
4501  ATGGAGAGAG GGGGTCAAAG ATGGAGCAAA GAAGGATGAG CAAGAAAATG
4551  GTGGATGTGG ATACTCTGAG GATGGCCTGG CTGTGGTGAG CAAAATGTGG
4601  GCAAAGTGGC ACTCCATGAA CAAGACAGCT TGCTCTGTTT GCAGATCCTT
4651  AAATAAAGGC ACATGGCATG CCATGGAGGC TAGGGGAGTG GAGGGGAAAG
4701  GTATATAGAT AGATGCAGAA GTACCAGAGG AGCCAGGAAG GACAGGAGTA
4751  GGAGGGACAG GTTTGCACAA GGCTTTGTCC TCTCCCCACC AGCTCTCTCT
                            JP.AS11
4801  CCCTTCTGTA TATGCACATA CACAGTGAGC TAGTGTGCAT ATGTGTGCAC
4851  ATATGCATGT GATGAACAGA GGCCAGTCTT GGGTGTCAGT CTTCAGGCCC
4901  TATCTACCTT GTTTTTGAGA CAATCTCACT TGAGTGAGTT GAGTGACTCT
4951  CCTAGTATTC TACAGAGGTT TCCTCAGGTG GGAGGAATG GGTGGGAGAA
5001  GCAAATTTAA GACTGGTTGA TTTCTTGAAT TTCAGTGGGC TTGGGAAATA
5051  GCAGCTATAT ATTCAGTTTC CTCGTTCCTG GCTGGCTTCC TGGGGTGATC
5101  AGAGCAGAGT ATAGTAGCCC TGTGTGGCAG TCACACCAAG CAGACAGAAG
5151  ATAGGGCATG GCTCTGGTGT GGCTGGTAGA CATAGGAAAG GATCCTTGTA
```

FIG.10D

```
5201  GCAAGATGTT TGCCATCTCC AGAGACTTAG ACAGCCCAGG AAAGTTTGTC
5251  CTCCCAGGAC CAGCCAGCAC TGAGACTGGA ATGCATCAAA TCCAGAGACC
                       JP.AS10
5301  AGAAAGCACG GTGCTAGCAC TTAGGAAGAG ACACTAGCCC AAAGTCTCCT
5351  TGCTCCTGCC TAAAGCTTTG CCAATTCTGC AAACCTTGAA AAATTAGCAT
5401  CTTTAAATTC AGAAGGGATA CAAGAAGAGA ACTTACATGG GACCTTGTAA
5451  AAAAGCATAG GGCATCAGTA ACTAAAGTTA CAAAGATAAC AATCAGTGGT
           ZT.S2
5501  GAGTGAACAA AGGACATGGC CATGTTTTTT TTGTTATGAA ACACACGCAC
5551  AGGCACAGGC ACTCACGTGT GCGCACGCGC GCACACACAC ACACGCGCAC
5601  ACACACACAC ACGCATGCAC ACATGCACCA CACACAAACT GCAAAAGTGA
5651  ATAAAAAGAT ATTTCTCACT TTGGCAAAGT GGATGGAAAG TTGATCAAAA
5701  TGAAAGTTAT ACTCAGAACT ATTTGTACT AGAGGGAGGT TATAAATTAT
                                           JP.AS9
5751  TGTTATTGTT ATATTCTATT TTACTGTTTG TGGCAGCCTA AGTTGGTCTT
5801  GAACTCACTA TGAAGCTAGC AATGACCTTG AGCTTCTGAT CCTTATATCT
5851  ACACTCTCAA GTGCCCAGAT TATAAGTGTG CACCACTATA CTCAGTTTAT
5901  GCTGTGCTAA GGACTAAGCC CAATTATACA AACACACACA CATATATACA
5951  CACATACACA CACACACACA CGTATATATA TGTATATATA TATACATACA
6001  TACACACACA CACACACATA TATGTAAAAT TTGGGAAGAT ATATCAATCT
6051  TCTTTAAAGT ACATGCTACT TTGGTCCAAA ACTTTCACTT TTAGGAAGTT
6101  AAGAAGGAAG AGACAGAATA AGAGATGTCC CAAGAAAGTC AGTGTGGTTG
6151  TCTTAGTTAT GCTTCCTGCT CAGTCAATGT TTCAGATTTT TCTCAGCACA
                  JP.AS8
6201  ATGACATCTA TTCTATCAAG TTTTTGATAA CTCTTTACAT GGGACTGGGT
6251  GTGGCTTGTG GCTCTAGCTA TTTCTATTTG TGACTGCCTA TCAGCAAAGC
6301  ATCCACTTCA GACTTTGACT CAAACATCAC CAAGTATTCC CACTTGCATT
6351  GTCTCTGTTA ACCAGCATCA CTGTTCACAG GGCAGGGCAT CACATCTCAC
6401  AAAGGGAAAG GGAAAGGGAA GAGTTAAATT CCCTGGGATA CTAGTCACGG
6451  TGGACTCAGG CAAACAGCCT CTTCAATTGT AAGATGATTC CCTAGTCCAA
                                                    JP.AS6
6501  GGACCCTCTA CTGTTTGGAC TCCAGTCTTG TCTGACAGAG GTCCAGTTCA
```

FIG.10E

```
6551  GGAGTGTCCA GATGGTCTGA TAACCTGATG CCATTCTCAG AGACTCTTTC
6601  CTGTCTGGAA TCTAGTGAGG AGGACTTATC TGGTGAAGCT GTCCTTTAGA
6651  ACAGGAGTGT GTTCCAGTCT TCAAAGCAAA CATTCCTTTT ATCCTAACAC
6701  AGTCTGACTT CAGATATACT GTCTTTTTCC TGGCTCCTTG GGCTTAGGTC
6751  TACCTTGTCC TTGCCCAGGT CCAAGAAAAG GCCCAGAACC TTGGCACTGT
6801  TTTGCCAGTT AATGTCTAAC TGAGGAATGT CTTGCTGCCA AAAGGTGAAA
6851  ACAGAGACCT TGTATTTCCA GGCACAGGTG TGACCCCAAT GTCAATCATT
6901  TTGTGTCTAA CTCCCAGGGG AAAAACTAAC AACAAGAC TCATGGCTTG
                                              ZT.S3
6951  GAAAAGGTGA ATTCTATGCC AAAAGGGAAG GAAAGTTCTA CCCCCACAGA
                          ZT.S4
7001  AACAATCTCA GAGGGCAGAA GCAGAGAATA ATCTGAGGGA GAGGGCCAGC
7051  CAAGGGCAGG CAAGTATATA TTGATCACAG GCACTTACTT GTGAATGGAC
                                                       EXON 1
7101  CAGTCCTGTC CTGGGTTCAG GTAAGGCTGT ATGAAACTGT CACCCCCATA
                     JP.AS15
7151  TCCACTTCTC CTCTATCTAA TCCCATTATA TTTCAGGGAG GTTGTGGTAG
                                                     JP.AS4
7201  AAGCTTAGCT TCTGGACACT GGGGTCCCAT GCTAACCTTC ATGGCATCCT
7251  GGTATGCTGC TGTAAAACCT AGGGTAATGC TTGCATCCAT CTGGAATTAT
7301  TTCACCTGTT GCAACCACAA TCATTTGAA AATACTAGTA TGTATTATAG
7351  TTATGTATGT ATATAGAGTT AATCATCTCT AAAGCTCCTT ATCTTTTGCC
7401  ATTTCTTTAC ATGAGTTGTA TGAAGATGTA GACGATATTC ATTATTCTCT
7451  TTGGTATCTA GCACCTTGTT TGGCACATAA TACTACTCAA TAAGGGTTTG
7501  TTGAATGAAT AAGTAGGTGA GAGCAAATTG TAAGTTCAGG TAATCACGAA
7551  CTTCCTGTAA AACTCCAAGG CTGCCTCCAG TAAGGTATAA GTCCTGAGTG
7601  AGCCTTTCCC CATCTTGCAA CTTTTTGCTC CAAATGAAAG ACTCAGTTCT
7651  TCAAAATGTG CAGCACATGG AGGTTTGCGA CATAGGGGTG TATTCACAGA
7701  GGCTTCGGAA GCCCACCAAA CCTACAGTTA GATCACTGTA CAGTCTTCCT
        JP.AS2
7751  TTTACATACA AGCTGTGCCT CCTGGTNTAC ATCCATGCTG TTTTCTGATC
7801  CATATAGAGG GTACACAACA AAAGCATTTC TTCTGTCTAT AGGGAAGCAA
7851  ATTAGATCAT GCATGTGCCT CACCCACCTC TGTTCTCATG ATTTCAGGCA
```

FIG.10F

```
                                                              EXON 2
7901   TCAGAAACAC AAGGGAAATC CAAAGTACCT AACCCATCCT TGCCTTTGGG
7951   CAGGTGTTTC CAGGACAGAG GGCAGAGTGT AAAGGATGGG GATCCCTTTG
8001   ACCTGGATGC TGCTGGTAAT GATGGTAACC TCCTGGTTCA CTCTGGCTGA
8051   AGCCAGTAAC TCAACAGAAG CGAGTAAGTG TGTGTGTGTG TGTGTGTGTG
8101   TGTGTGTGTG TGTGTAGAGA AATGTTCCCT TTGCAGAAGC AATCTTAATC
                        JP.S1
8151   CCTCTTTTAG CACACTTGAT GTGATCTTTA TTTTAAGCCC ATTTCTCAGA
8201   TTGTAATGAG CACAGGACTC ACTTCGAAGT TTTGTTAAGA TGCAAATTCT
8251   ACTTTAGTAG GTCTAGCAAG GGG/CCGAGA CTCTGAATTA ATAGCAGCGT
                             APA/KPN JUNCTION
8301   GTGGGTGATG TTTCTGGTGG GACAAGGGGC TAAAACACCT CTGAACCATT
8351   TCTGCACTTC ACGGTAAAGT CACAAGCATG CCCAGATACA TAAGAGATTT
8401   GACCCACCTC TCCTGTAAGT GTGAAGTCAT CCCATGGGGG TAGCTTTGCC
8451   TTCCACCCTG GAGTACTCTG GAATTACACT AAGTATAATT GTGAGGTCAT
8501   GGTTAAAAGC ACATGTTCTG TGGTCAGGCC ATGTGCGTGT ACCCTGTTTG
8551   ACAACTGGCT TGCTCGTTCT GAATGTCAAT ATTCTTTTCT GTAAATGAAG
8601   AAAATGAAAA TGGGTTCCAG CGGCAGGGGG TGTGCCCTGG GGAGGATTCG
8651   CTAAACTCTA GACTGAAAAG TCAATGAATA GAGGACTCCA CTCAGGGGAG
8701   CTCGGATGGG TGTGTTTTGA AGGTGCCAAC AACTTAACAA GTCCAGAAAA
8751   GCAAGAAAGT ATGGGCAGGG GCACCTGCCA GCTGCAGGGA TTCTGAAGCT
                        JP.AS5
8801   GGGCTCTTCT GTCCGCAGGA CGGTGTTCTG AATGCCACAA CAACGCCACC
                                          EXON 3
8851   TGCACGGTGG ATGGTGTGGT CACAACGTGC TCCTGCCAGA CCGGCTTCAC
8901   TGGTGATGGG CTGGTGTGTG AGGACATGGA TGAGTGTGCT ACCCCATGGA
8951   CTCACAACTG CTCCAACAGC AGCTGTGTGA ACACCCCGGG CTCGTTTAAG
9001   TGCTCCTGTC AGGATGGTTT TCGTCTGACG CCTGAGCTGA GCTGCACTGA
9051   TGTGGATGAG TGCTCAGAGC AGGGGCTCAG TAACTGTCAT GCCCTGGCCA
9101   CCTGTGTCAA CACAGAAGGC GACTACTTGT GCGTGTGTCC CGAGGGCTTT
9151   ACAGGGGATG GTTGGTACTG TGAGTGCTCC CCAGGCTCCT GTGAGCCAGG
```

FIG.10G

```
9201  ACTGGACTGC TTGCCCCAGG GCCCGGATGG AAAGCTGGTG TGTCAAGACC

9251  CCTGCAATAC ATATGAGACC CTGACTGAGT ACTGGCGCAG CACAGAGTAT

9301  GGTGTGGGCT ACTCCTGTGA CGCGGGTCTG CACGGCTGGT ACCGG
                                                  POLYCLONING SITE OF pBS
```

FIG.10H

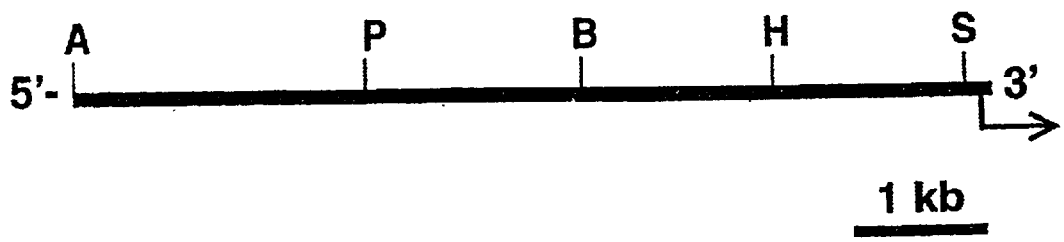

FIG. 11

```
  1  TACTGGCGCA GCACAGAGTA CGGCTCCGGC TACGTCTGTG ATGTCAGTCT
                                           AS14
 51  GGGCGGCTGG TACCGCTTCG TGGGCCAGGG CGGCGTGCGC CTGCCCGAGA
101  CCTGCGTGCC CGTCCTGCAC TGCAACACGG CCGCGCCTAT GTGGCTCAAC
                                               AS15
151  GGCACGCACC CATCGAGCGA CGAGGGCATC GTGAACCGCG TGGCCTGTGC
201  GCACTGGAGC GGCGACTGCT GCCTGTGGGA CGCGCCTGTC CAAGTGAAGG
251  CCTGTGCCGG CGGCTACTAC GTGTACAACC TGACAGAGCC CCCTGAG
             AS17
```

FIG. 12

```
  1  ACTATAGGGC ACGCGTGGTC GACGGCCCGG GCTGGTAAAT CTTAAAAAAA
                      ‾‾‾‾ ‾‾‾‾‾‾‾‾‾‾ ‾‾‾‾‾‾‾‾‾‾ ‾‾
                              AS1
 51  AAAAAAAACA AAAAGAACAT CACTAAGCCC CCCTGCCCTG GCACTTTATT
                                  ‾‾‾ ‾‾‾‾‾‾‾‾‾‾ ‾‾‾‾‾‾‾‾‾‾
                                        AS2
101  GGAAGGTCAA GAACACACTC AACCACACAA GAGATGTGAA CATACCTGTG
     ‾‾‾‾‾‾‾‾‾‾ ‾‾‾‾‾‾‾‾‾‾
             AS3
151  TGGTACCCAA AGACATCCCC TTTCACACAT ACATGACCCT TCCATTGGGT
     ‾‾‾‾‾‾‾‾‾‾ ‾‾‾‾‾                                ‾‾‾‾‾‾
          AS4                                        AS5
201  TGCACATTGC TGTTAGCTTT TTGTTGGAGA AGGGAGCTAG ACACCTCTAC
     ‾‾‾‾‾‾‾‾‾‾
251  ACAACCCCCA ACTGGAGTTC TCTGGAACAG AGTAAATACC ATCGTGTCAT
301  CATGGAGCGC ACACACACTG TGGTCCTGCA ACCTCGATTT GTGTCCTGGC
351  TCTGCTGCTT ACCAATGAAG CAAGTAGCTT AAACCTTCTG AATCTCAAGT
401  TTCCTCACCC TCAAACTATA GCTAAATACA AAAGTCATTT CCCAGGGCCA
451  CTGGAGAGGA TTCTATCAGA TAATGGATAG AAGATGCCTA TCCCAGTGTT
501  TGACATATCC TAAGTGCTTA ATACACGAGA GCTCACCATC TTTACTGGTA
551  TTATTGCACA GAGAAACACA CAAAGTGTCA GTGCCCCTGC TAGGTAGAGA
601  GGGANGCANG GNAAGGAGAT CTGAGCAAAA GGCATAGAAT ATATCAAGCT
651  GGG
```

FIG.13A

```
  1  CGGGGGAAGG TTTATTTTGT TTCTTTTCAA AGGGGGTCTT GNTCTGTCTC
 51  AAAGACCNTA AGGACCATGA AAAAATCTCT TTGTNAAAAG TGCCAAGCGG
101  TCCCCACTCT GAATCTGGGC TTTTCTGCCT GCAGAAAGCT GCTCTGAATG
151  TCACGCCAAT GCCACTTGTA CGGTGGACGG GGCTTGCCAC GACCTGCGCC
201  TGCCAGGAGG GCTTCACTGC GACGGCCTCG AATGTGCGGA TCTGGATGAA
251  TGCGCCATTC TGGGGGCGCA CAACTGCTCC GCCACCAACA GCTGCGTGAA
301  CGCGCTGGGC TCCTACACAT GCGTCTGCCC TGAAGGTTTC CTCCTGAGCT
351  CGGAGCTCGG CTGCGAGGAT GTGGACGAGT GTGCAGAGCC AGGGCTCAGC
401  CGCTGCCACG CCCTGGCCAC CTGCATCAAT GGCGAGGGCA ACTACTCATG
451  CGTGTGTCCC GCGGGCTACG TGGGGACGG  GAGGCACTGT GAGTGTTCCC
501  CGGGCTCCTG CGGGCCTGGG CTAGACTGCG TGCGGGAGGG TGACGCGCTA
551  GTGTGCGCTG ACCCGTGCCA GGCGCACCAC ATCCTGGACG AATACTGGCG
601  CAGCACAGAG TACGGCTCCG GCTACGTCTG TGATGTCAGT CTGGGCGGCT
651  GGTAC
```

FIG.13B

```
  1 ACTATAGGGC ACGCGTGGTC GACGGCCCGG GCTGGTAAAG ACACCCAGAC
 51 TTAGGTTTTG ACAGAGCCTC ATGTTCACCA ACCAGAAATG ACATTCACCA
101 CCTAGGATTG AGAAAAAGAA TATTAGGAAC TTTTATTTTC TTCTGAAGTT
151 ATAGCAAAGA AAGGGGAAAA AAAAAAACAT TCTTATGGGG ATAAACGGG
201 CAAAGGATAC AAACAGTTCA GAAAGAATA AATAGTAAGC AAATGAAAAG
251 ATAACTTCCT TTTTCATCAA AGAACCGCAA AAGTAAATAA TGATAAGATG
301 TTTCTCACTT TTCCACAAAG ATGAAAGTTA ATGCCCAGGG TGGCTGAGTA
351 CTGTGCTGGG ATTGTGAACT AACTGTTATA GATCTCTCTG GGGTGCTGTT
401 TGGGAAGAAA CATCGCTGAA AACTGAGCTA CCTCTTTTCC TATGAAATTC
451 CCCTGAGGAG GTGAGTGAGC CGCTGCTGAT CGTCACCCGA GCACTAGGCC
501 AGACAGAAGG AGAAAGCCCT CAAAGAGGCA ATGCTGTGGA TCACTGTCAT
551 ATTTCCTGCT CAGCCTGAGT TCACATGTGC CTGATTTTTC TCAATATGGC
601 ATTGCCATTA ACGTGGAATT AGGTCAGGAG ACCTAAGGCT GAACCAAGCC
651 CTGTCATTCT CTGCCCCATG ACTGCGCATC ACCAAAACAG CATCGGCAGT
701 GACTTCCACA GATGGTACCA TTGCTATATG CCTTAACTTG CATCATCTCC
751 TTTAATGGCC ATAACAATTC TAGGACACGG GTATTCTTGT TTTACAGATG
801 ATGAAAATTA CCTCTGGAAG GAAAATTACT GGCACACAAA AAACGCTGAC
851 CAGGATTCAG ATAGACTGAC TCCAAAGTCA GTCTGTTCAT CTACAAAATT
901 ATCTACTTCT CAAGGACCTT CCTTCATGGG AATTCAAATT TCTTGATTCA
951 CAGAGCATCT GGTCCAATGA TGTCTGAATT ATCTGCTGTC TCTGACCTTC
```

FIG.14A

```
1001  AGCCATTCTC AGCTCCTTTC CTGATCACAT TGGGACCCCA GGGGAGCTGG

1051  CTGAATCTGT GAGGATGGCA TTTGCTTTGG AATTAAGTGG CCACAAGTAC

1101  ACATCCTGGT GGGGACGATG AGCACCCCTT TTCTCCTGGA GCAGCCTGGC

1151  TTCAGATTCT GGCCTCTGCT TGGCTCCACT TTGTGCTTTT CAATGACCAA

1201  GAAAATCCCA GGCCCTTGGA ATTGTTTACT CAGTTAATTT CTAACTAAAG

1251  AACCTCTTGT TGCCAAAAGG TATAAACAG AGCCCTTGTA GCTGTGGGCA

1301  CAGCTGTGAC CCCCATGTCA ATCATTTGGG GTCTCTACCT ATTAGGGAAA

1351  AGAACAACAA CCACCTCACA GCCTAGAAAA GGAAAACACT GTGTCAAAAG

1401  GGAAAAATAT TCCACCCCCA TTAAAATAAT TAAGAAACAG AACCAGAGGA

1451  TCATTGGAGG AGAGATTGCC AGTGGGGAC AGATGTATAT ATATAGATAT

1501  GAAAGTCACC TACTTGTAAA AGGATTAATT CTACCTTTCT GGTTTCAGGT

1551  AAGGCTATCT GCAGCTCTCA CTTCTCCTAG CCACTTCTCC CATCTAGTCT

1601  TTGCTGGCTC CCATTCTGTT TGAAGGATGG
```

FIG.14B

```
$ type guromodulinpromoter18full.pair;1
  BESTFIT of: Guromodulinpromoter18full   check: 3852   from: 1 to: 1630 to: mouseThppromoterfull.   check: 5595   from: 1 to: 9343

Symbol comparison table: Gencoredisk:[Gcgcore.Data.Rundata]Swgapdna.Cmp
CompCheck: 2335

Gap Weight:       50      Average Match:  10.000
       Length Weight:        3      Average Mismatch: -9.000

Quality:    1617             Length:      534
                Ratio:   3.177               Gaps:       15
   Percent Similarity:  74.385    Percent Identity:   74.385

Match display thresholds for the alignment(s):
                    | = IDENTITY
                    : = 5
                    . = 1

Guromodulinpromoter18full x Thppromoterfull.  March 24, 2000 16:31
```

```
1121 AGCACCCCTTTTCTCCTGGAGCAGCCTGGCTTCAGA............T 1157
     | ||  ||||||  ||||    |||  |||  ||||||||          |
6677 AACATTCCTTTTATCCTAACACAGTCTGACTTCAGATATACTGTCTTTTT 6726

1158 TCTGGCCTCT...GCTTGGCTCCACTTTGTGCTTTTCAATGACCAAGAAA 1204
     |||||  ||    |||| | || |||| |||  | |   |||||||||
6727 CCTGGCTCCTTGGGCTTAGGTCTACCTTGTCCTTGCCCAGGTCCAAGAAA 6776

1205 A.TCCCAGGCCCTTGGAATTGTTTACTCAGTTAATTTCTAACTAAAGAAC 1253
     | |||||  ||||||  |||||| ||||||||| ||||||| |  |||
6777 AGGCCCAGAACCTTGGCACTGTTTTGCCAGTTAATGTCTAACTGAGGAAT 6826

1254 CTCTTGTTGCCAAAAGGTATAAAACAGAGCCCTTGTAGCTGTGGGCACAG 1303
     ||||| ||||||||||||  |||||||||  ||||| |    |||||||
6827 GTCTTGCTGCCAAAAGGT.GAAAACAGAGACCTTGTATTTCCAGGCACAG 6875

1304 CTGTGACCCCCATGTCAATCATTTGGGGTCTCTACCTATTAGGG...AAA 1350
     |||||||| |||||||||||||||  || ||| ||  ||||    |||
6876 GTGTGACCCCAATGTCAATCATTT..TGTGTCTAACTCCCAGGGGAAAAA 6923

1351 AGAACAACAACCACCTCACAGCCTAGAAAAGGAAAACACTGTGTCAAAAG 1400
     ||||||||| ||||  ||  | ||||||||  || || || ||||||
6924 CTAACAACAACAGACTCATGGCTTGGAAAAGGTGAATTCTATGCCAAAAG 6973

1401 GGAA.AAATATTCCACCCCCATTAAAATAAT.TAAGA.AACAGAACCAGA 1447
     ||||  || ||| ||||||    ||| ||| | |||  |||| ||||
6974 GGAAGGAAAGTTCTACCCCCACAGAAACAATCTCAGAGGGCAGAAGCAGA 7023

1448 GGATCATTGGAGGAGAGATTGCCAGTGGGGACAGATGTATATATATAGA 1497
     | || ||  ||||  |||||| |||   || |||||| | ||||||
7024 GAATAATCTGAGG.GAGAGGGCCAGCCAAGGGCAG..GCAAGTATATATT 7070

1498 TATGAAAGTCACCTACTTGTAAAAGGATTAATTCTACCTTTCTGGTTTCA 1547
     || | || ||| |||||||| || ||| | ||     | |||| ||||
7071 GATCACAGGCACTTACTTGTGAATGGACCAGTCCT....GTCCTGGGTTCA 7117
```

FIG.15A

```
1548 GGTAAGGCTATCTGCAGCTCTCACTTCTCCTAGCCACTTCTC..CCATCT 1595
     ||||||||| | || | || |||| | | || |||||||||| | ||||
7118 GGTAAGGCTGTATGAAACTGTCAC.CCCCATATCCACTTCTCCTCTATCT 7166

1596 AGTCTTTGCTGGCTCCCATTCTGTTTGAAGGATG 1629
     |       ||||||| | ||| | ||| |
7167 A...........ATCCCATTATATTTCAGGGAGG 7189
```

FIG.15B

TRANSGENIC ANIMALS AS URINARY BIOREACTORS FOR THE PRODUCTION OF POLYPEPTIDE IN THE URINE, RECOMBINANT DNA CONSTRUCT FOR KIDNEY-SPECIFIC EXPRESSION, AND METHOD OF USING SAME

CROSS-REFERENCE TO RELATED APPLICATIONS

The present application is a continuation-in-part of application Ser. No. 09/438,785, filed Nov. 12, 1999, now abandoned, which claims priority under 35 U.S.C. §119(e) from U.S. provisional application 60/108,195, filed Nov. 13, 1998, and U.S. provisional application 60/142,925, filed Jul. 9, 1999, the entire contents of each of these prior applications are hereby incorporated by reference.

BACKGROUND OF THE INVENTION

1. Field of the Invention

The present invention relates to transgenic animals as urinary bioreactors for the expression and production of polypeptides in the urine. The present invention further relates to a recombinant DNA construct for kidney-specific expression of polypeptides in the urine and to a method for producing such polypeptides in the urine.

2. Description of the Related Art

Significant progress has recently been made in using transgenic animals as bioreactors to produce large quantity and high quality pharmaceuticals. The overall strategy entails the use of tissue-specific promoters to drive the expression of genes encoding medically important molecules. When those molecules are expressed in the target tissue of transgenic animals and secreted into body fluids, they can be harvested, purified and used for treating human diseases. The most notable example is the milk-based bioreactor system, taking advantage of mammary gland-specific gene promoters. U.S. Pat. No. 5,476,995 was one of the first patents directed to transgenic female sheep as milk-based bioreactors that expressed the transgene in the mammary gland so as to produce the target protein in its milk.

A number of proteins have been produced in milk-based bioreactor systems, such as protein C (U.S. Pat. No. 5,589,604), blood coagulation factors (U.S. Pat. No. 5,322,775), fibrinogen (U.S. Pat. No. 5,639,940), antibodies (U.S. Pat. No. 5,625,126) and hemoglobin (U.S. Pat. No. 5,602,306), some of which are now being used in clinical trials. However, even in view of its initial success, a milk-based bioreactor system has several limitations. The first relates to its relatively low degree of cost-effectiveness. For instance, the lactation of transgenic livestock does not occur until an average of one and a half years old. Besides, lactation only occurs in female animals and lasts for a limited period of time. Secondly, purification of target proteins from milk often requires the development of complicated purification schemes (Wilkins et al, 1992). Thirdly, leakage of biologically active proteins from the mammary gland into the blood stream commonly occurs with the possibility of leading to pathological conditions in transgenic animals.

Another potential bioreactor system that can circumvent some of the above-mentioned limitations is a urine-based system where urine is an easily collectable fluid from transgenic livestock animals. This bioreactor system has been recently tested by Kerr and colleagues (1998), among whom is one of the present inventors, in transgenic mice using a urothelium-specific promoter (uroplakin II promoter) to drive human growth hormone (hGH) expression and production. They found that hGH could indeed be found in the urine of these transgenic mice at a concentration of 0.1 mg/ml, indicating that the urothelium can serve as an alternate bioreactor. The major advantages of this urine-based system over milk-based systems are the ability to harvest the product soon after birth and throughout the life of the animal irrespective of sex or reproductive status and the ease of product purification from urine. In addition, livestock urine is a proven, currently utilized source of pharmaceuticals; it is estimated that urine is being collected from 75,000 pregnant horses annually as a source of estrogenic compounds for postmenopausal hormone replacement therapy (Williams, 1994).

Despite these major advantages, several technical problems still exist with the above-mentioned urine-based bioreactor system, the most important being the relatively low yield of urinary hGH (0.1 mg/ml) obtained by Kerr et al (1998), as most of the hGH appear to be trapped in the cytoplasm of the superficial urothelial cells. This relatively low yield may be because the urothelium is not known to be a major secretory epithelium and the purification of a minor protein from urine may require sophisticated purification procedures. In addition, low levels of hGH was found to have leaked into the mouse blood stream, possibly being responsible for the infertility observed in the transgenic female mice.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It is an object of the present invention to overcome the above-mentioned deficiencies in the art by providing a urine-based bioreactor system using a kidney-specific promoter for the expression and production of a recombinant biologically active polypeptide and a targeting system for the apical surface membrane of kidney epithelial cells.

The present invention provides a recombinant DNA molecule containing a kidney-specific promoter operably linked to a heterologous DNA sequence, which kidney-specific promoter is capable of expressing the heterologous biologically active polypeptide, encoded by the heterologous DNA sequence and containing an apical membrane targeting system, in the kidney of a host animal to produce a recombinant biologically active polypeptide in the urine.

As an embodiment of the present invention, the heterologous biologically active polypeptide contains a glycosyl phosphatidylinositol (GPI) signal sequence at its C-terminus to target the heterologous biologically active polypeptide to the apical surface of kidney epithelial cells for secretion into the lumen. In another embodiment, the heterologous biologically active polypeptide can be expressed as a fusion polypeptide between a biologically active polypeptide of interest and uromodulin via a protease-sensitive linker. The C-terminus of this fusion polypeptide is the C-terminus of uromodulin and contains a GPI signal sequence.

A further embodiment of the present invention provides for introducing one or more non-native sites for glycosylation into the heterologous biologically active polypeptide.

Yet another embodiment of the present invention is directed to an operable linkage of the kidney-specific promoter to both the heterologous DNA sequence encoding a heterologous biologically active polypeptide and a DNA sequence encoding phosphatidylinositol-specific phospholipase C (PIPLC), which DNA sequence encoding PIPLC is positioned downstream from the heterologous DNA sequence relative to the kidney-specific promoter.

A further object of the present invention provides a urine-based bioreactor system in which apical surface membrane targeting is enhanced by the inactivation or deletion of basolateral surface membrane targeting signals in the recombinant biologically active polypeptide.

The present invention also provides for a method for producing a recombinant biologically active polypeptide in vivo using a urine-based bioreactor system in transgenic animals. Further provided are transgenic animals, all of whose somatic cells and preferably all of whose germ cells contain a recombinant construct or transgene from which a biologically active polypeptide is produced in recoverable amounts in the urine.

BRIEF DESCRIPTION OF THE DRAWINGS

FIG. 3 is an amino acid sequence comparison/alignment of rat (SEQ ID NO:38), mouse (SEQ ID NO:39), human (SEQ ID NO:40), and bovine (SEQ ID NO:41) uromodulin. Boxes represent potential Asn-linked glycosylation sites and underlines represent the GPI attachment site and indicate that the sequence in this GPI attachment site of uromodulin is highly conserved across species.

FIGS. 10A–10H show the nucleotide sequence of the mouse uromodulin promoter region (SEQ ID NO:1) which is 9,345 bp upstream of the first mouse uromodulin coding exon.

FIG. 11 is a schematic presentation of the mouse uromodulin promoter in which the arrow denotes the transcription initiation site, the letters denote restriction sites (A, ApaI; P, PstI; B, BamHI; H, HindIII; S, SpeI), and the short bar denotes the relative size of the DNA.

FIG. 12 shows the partial cDNA sequence of goat uromodulin gene (SEQ ID NO:2). The location of primers AS14, AS15 and AS17 used for isolation of goat uromodulin genomic DNA is shown in underline.

FIGS. 13A and 13B show the nucleotide sequence of goat uromodulin gene intron 1 (FIG. 13A; SEQ ID NO:3) and exon 3 (FIG. 13B, SEQ ID NO:4). The location of primers AS1, AS2, AS3, AS4 and AS5 used in genomic walking is indicated.

FIGS. 14A and 14B show the nucleotide sequence of the goat uromodulin promoter region (SEQ ID NO:37). The boxed sequence denotes the TATA box and the arrow denotes the putative transcription initiation start site.

FIGS. 15A and 15B show a homology comparison of goat and mouse uromodulin promoter regions corresponding to nucleotide positions 1121–1629 in SEQ ID NO:37 and nucleotide positions 6679–7191 in SEQ ID NO:1 (designated in FIGS. 15A and 15B as nucleotides 6677–7189), respectively. Gaps are denoted by a period (.) between nucleotides.

DETAILED DESCRIPTION OF THE INVENTION

Figure 1:
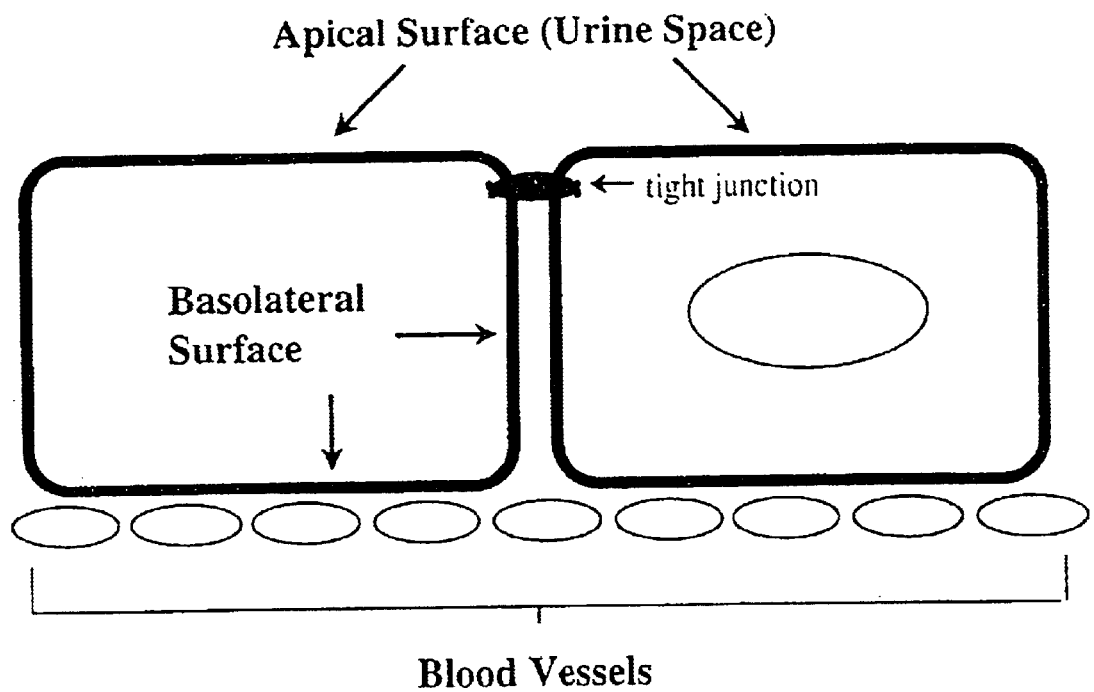
FIG. 1 is a schematic diagram showing the apical and basolateral surfaces of kidney epithelial cells in relation to the urine space (lumen) and blood vessels.

The present invention relates to the development of a bioreactor system in a transgenic mammal where a recombinant biologically active polypeptide is produced and secreted into the urine by the kidney-specific expression of a heterologous polypeptide, which is encoded by a heterologous DNA sequence, under the direction of a kidney-specific promoter, such as the uromodulin promoter. This urine-based mammalian bioreactor system, according to the present invention, is obtained by producing a transgenic mammal in which an isolated DNA molecule containing a recombinant construct or "transgene" for kidney-specific expression and production of the biologically active protein of interest is stably introduced. An example of a urine-based bioreactor system where the protein of interest is expressed in urothelial cells, rather than kidney cells, but which serves as guidance to development of a urine-based bioreactor system, is provided by Lin et al (1995) and Kerr et al (1998). The present invention advantageously combines kidney-specific expression with apical surface membrane targeting to overcome the problems associated with leakage of an expressed heterologous biologically active polypeptide into the bloodstream.

To produce transgenic animals, any method known in the art for introducing a recombinant construct or transgene into an embryo, such as microinjection, cell gun, transfection, liposome fusion, electroporation, and the like, may be used. However, the most widely used method for producing transgenic animals, and the method most preferred according to the present invention, is microinjection, which involves injecting a DNA molecule into the male pronucleus of fertilized eggs (Brinster et al, 1981; Costantini et al, 1981; Harbers et al, 1981; Wagner et al, 1981; Gordon et al, 1976; Stewart et al, 1982; Palmiter et al, 1983; Hogan et al, 1986; U.S. Pat. No. 4,870,009; U.S. Pat. No. 5,550,316; U.S. Pat. No. 4,736,866; U.S. Pat. No. 4,873,191). While the above methods for introducing a recombinant construct/transgene into mammals and their germ cells were originally developed in the mouse, they were subsequently adopted for use with larger animals, including livestock species (WO 88/00239, WO 90/05188, WO 92/11757; and Simon et al, 1988). Microinjection of DNA into the cytoplasm of a zygote can also be used to produce transgenic animals.

Alternatively, a recombinant construct or transgene can be introduced into embryonic stem cells (ES cells) by any method known in the art, such as those identified above as non-limiting examples. The ES cells transformed with the transgene are combined with blastocyst of the same animal species to colonize the embryo (Jaenisch, 1988). In some embryos, these transformed ES cells form the germline of the transgenic animal generated by this procedure. Transformed ES cells can also be used as a source of nuclei for transplantation into an enucleated fertilized oocyte to produce a transgenic animal.

The present invention for producing a biologically active polypeptide in a urine-based mammalian bioreactor system is not limited to any one species of animal, but provides for any appropriate non-human mammal species. For example, while mouse is a mammal species that is routinely used for producing transgenic animals and, thus, serves as a model system to test the transgene, other non-limiting but preferred examples include farm animals, such as pigs, sheep, goats, horses and cattle, which generate large quantities of urine, may be suitably used. A most preferred animal for use as a urinary bioreactor is a goat.

The success rate for producing transgenic animals by microinjection is highest in mice, where approximately 25% of fertilized mouse eggs into which the DNA has been injected, and which have been implanted in a female, will develop into transgenic mice. Although a lower success rate has been achieved with rabbits, pigs, sheep and cattle (Jaenisch, 1988; Hammer et al, 1985 and 1986; Wagner et al, 1984), the production of transgenic livestock is considered by those in the art to be routine and without undue experimentation. Wall et al (1997a), Velander et al (1997), Drohan (1997), Hyttinen et al (1994), Morcol et al (1994), Lubon et al (1997), Houdebine (1997), Wall et al (1997b), Van Cott et al (1997), Cameron (1997), Cameron et al (1994), Niemann (1998) and Hennighausen (1992), among others, have reported and discussed the use of livestock as bioreactors or factories for the production of biologically active proteins.

The introduction of a DNA containing a transgene sequence at the fertilized oocyte stage ensures that the introduced transgene will be present in all of the germ cells and somatic cells of the transgenic animal. The presence of the introduced transgene in the germ cells of the transgenic "founder" animal, in turn, means that all of the founder animal's offspring will carry the introduced transgene in all of their germ cells and somatic cells.

There is no need for incorporating any plasmid or viral sequences with the gene being introduced, (Jaenisch, 1988), although the vector sequence may be useful in some instances. In many cases however, the presence of vector DNA has been found to be undesirable (Hammer et al, 1987; Chaka et al, 1985 and 1986; Kollias et al, 1986; Shani 1986; Townes et al, 1985). For instance, the transgene construct can be excised from the vector used to amplify the transgene in a microbial host by digestion with appropriate restriction enzymes. The transgene is then recovered by conventional methods, such as electroelution followed by phenol extraction and ethanol precipitation, sucrose density gradient centrifugation, chromatography, HPLC, or combinations thereof. It has been reported in U.S. Pat. No. 5,589,604 that high transformation frequencies, on the order of 20% or more, in both mice and pigs were obtained by microinjection with HPLC-purified DNA.

In order for the introduced gene sequence to be capable of being specifically expressed in the kidney of the transgenic animal, the gene sequence must be operably linked to a kidney-specific promoter. A DNA molecule is said to be "capable of expressing" or "capable of directing the expression of" a polypeptide if it contains nucleotide sequences which contain cis-acting transcriptional regulatory information, and such sequences are "operably linked" to nucleotide sequences which encode the polypeptide. An operable linkage is a linkage in which the regulatory DNA sequences and the DNA sequence sought to be expressed are connected in such a way as to permit gene expression. The cis-acting regulatory regions needed for gene expression in general include a promoter region, and such regions will normally include those 5'-non-coding sequences involved with initiation of transcription. A promoter region would be operably linked to a DNA sequence if the promoter were capable of effecting transcription of that DNA sequence. Thus, the DNA sequence encoding a polypeptide of interest is operably linked to a kidney-specific promoter to generate a recombinant construct or "transgene" that is then introduced into the fertilized embryo or ES cells.

Also included in the transgene are nucleotide sequences that encode the signal sequences that direct secretion of the expressed biologically active polypeptide of interest into the urine of the transgenic animal. Both endogenous and heterologous signal sequences (either for the host or for the biologically active protein of interest) can be used, although the endogenous signal sequence of the heterologous protein of interest is preferred. Furthermore, other regulatory sequences in addition to the promoter, such as enhancers, splice signals, ribosome binding sites and polyadenylation sites, etc., may be useful in the transgene construct as would be well-recognized by those of skill in the art.

The preferred promoter in the recombinant construct/transgene for the kidney-specific expression of a heterologous biologically active polypeptide of interest is the promoter for uromodulin. Uromodulin, also named Tamm-Horsfall protein (THP), is by far the most abundant urinary protein of human and other higher mammals, with an excretion rate of up to 200 mg per day (Hunt et al, 1985; Reinhart et al, 1989). This ~90 kDa glycoprotein has several important features that are relevant to its use in a kidney-expressed urine-based bioreactor system. The protein is synthesized by the epithelial cells of the ascending limb of Henle's loop and the beginning portion of the distal convoluted tubule, delivered exclusively to apical membrane and secreted into the urine (Sikri et al, 1981; Bachmann et al, 1990). Rindler et al (1990) established that uromodulin is a cell surface protein anchored onto the apical plasma membrane via a glycosylphosphatidyl inositol (GPI) tail, where phosphatidylimositol-specific phospholipase C (PIPLC)

cleavage in vitro of the GPI linkage completely releases the molecule into the culture medium.

Uromodulin is highly tissue-specific, being expressed only in the kidneys and not in any other epithelial and mesenchymal tissue. Moreover, uromodulin is evolutionarily conserved throughout placental animals. The cDNA sequences reported for rat uromodulin (Fukuoka et al, 1992) and human uromodulin (Hession et al, 1987; Pennica et al, 1987) were found to be 91% and 77% identical with the mouse uromodulin cDNA sequence, respectively (Prasadan et al, 1995). Prasadan and colleagues (1995) also reported that an alignment of uromodulin amino acid sequences from mouse, rat and human showed 91% similarity and 86% identity between mouse and rat, and 79% similarity and 70% identity between mouse and man.

As discussed in the Example 1 presented herein, the laboratory of the present inventors has isolated and sequenced a 9,345 base pair region including about 7 Kb upstream of the coding region of the mouse uromodulin gene, which region contains the mouse uromodulin promoter. This DNA promoter region, or a fragment thereof which retains the tissue specific promoter activity thereof, is used for construction of a transgene with a biologically active polypeptide of interest, i.e., human growth hormone (hGF). While knowledge of the nucleotide sequence of the mouse uromodulin promoter would facilitate the construction of a transgene which is capable of kidney-specific expression of a biologically active polypeptide of interest, such sequence information is not necessary because it is well within the skill of the art to isolate a functional promoter sequence given a uromodulin genomic clone with the upstream promoter region. There is a wealth of scientific literature directed to the isolation and identification of a promoter for a given gene, with the Kahari et al (1990) article on the delineation of functional promoter and regulatory cis-elements being just one representative citation. Clones containing the goat uromodulin gene promoter have also been obtained as disclosed herein in Example 2 with the sequence of the goat uromodulin promoter being presented in FIGS. 11A and 11B. Other uromodulin gene promoters can be further isolated using the genomic walking procedure described for the isolation of the mouse and goat uromodulin gene promoters in the Examples herein.

As a preferred embodiment of the present invention, a uromodulin-based urine bioreactor system has the following advantageous features:

(1) Uromodulin is a kidney-specific and abundantly expressed gene and its synthesis is confined to the thick-ascending limb of Henle's loop and early distal tubules of the kidneys. Biologically important genes under the control of uromodulin promoter are likely to be expressed in the same location and secreted into the urine, where the expressed gene products can be readily purified.

(2) Year-round production, which is independent of age and sex as compared to mammary-based bioreactor.

Uromodulin has already been reported to be evolutionarily conserved, being detectable immunologically in all placental mammals (Kumar et al, 1990). The laboratory of the present inventors has shown by Southern blot hybridization that the uromodulin gene is present as a single copy in many mammals, including all important livestock, such as cattle, sheep, goat, horse and pig. Not only do the uromodulin cDNAs from human, mouse and rat share a high level of identity (on the order of 80% or more), but even the high mannose glycosylation of uromodulin is highly conserved among different species of mammals. This strongly suggests that the promoter sequences of uromodulin are also likely to be conserved among mammals.

Moreover, as evidenced by the numerous examples in the scientific literature of promoters that are interchangeable among species, the uromodulin promoter from one mammal species is believed to be functional in another species. Accordingly, the mouse uromodulin promoter identified herein may be able to be used directly in transgenic livestock to drive kidney-specific expression of the biologically active polypeptide of interest in a urine-based bioreactor system. Alternatively, the uromodulin promoter used in the transgenic livestock to drive kidney-specific expression of the biologically active polypeptide can be its own endogenous uromodulin promoter, such as using the goat uromodulin to drive kidney-specific expression in transgenic goats, or an interchangeable uromodulin promoter from another species of livestock. A computer comparison of the nucleotide sequences of the goat and mouse uromodulin promoter regions determined by the laboratory of the present inventors only found homology (approximately 74%) over a short stretch of about 500 bp that includes the first exon of uromodulin (FIG. 12A). No other significant homology was found within about 1,100 bp of the promoter region 5'-upstream of this short stretch of homology. If it is later determined that the mouse promoter or any other non-native uromodulin promoter does not provide sufficiently kidney-specific expression in the transgenic animal, then the native uromodulin promoter would be used instead in the transgene construct.

The bovine and rat uromodulin promoter regions have already been identified in Yu et al (1994), the entire contents of which are hereby incorporated herein by reference. Specifically, FIG. 5 of Yu et al (1994) shows the nucleotide sequence of the bovine and rat uromodulin promoter regions. These promoter regions, or a fragment thereof with kidney-specific promoting activity, can be used to drive the kidney-specific expression of a heterologous gene in those respective species. If it is determined that the regions of the approximately 600 base pairs upstream of the transcription start site in the bovine and rat sequences of FIG. 5 of Yu et al (1994) do not contain the complete kidney-specific uromodulin promoter sequence for these species, additional nucleotides upstream of the disclosed sequences can readily be obtained and sequenced using the specific sequences as a probe of bovine and rat genomic libraries, or using the technique of genomic walking as described in the examples herein, without the use of undue experimentation.

Uromodulin promoters from other mammalian species can be isolated using the same approaches outlined in the examples provided herein, or using the same approach used in Yu et al (1994), or by hybridization or PCR amplification of genomic libraries or genomic DNAs using probes or primers from the genomic clones of the mouse, goat, rat or cow uromodulin gene. If the need to use a uromodulin promoter from another livestock animal species arises, then information generated from the mouse and goat uromodulin promoters or from the bovine and rat uromodulin promoter region of Yu et al (1994) can be used to facilitate this process. For instance, as the sequence of the mouse and goat uromodulin promoters have now been determined and are reported herein, and the bovine, rat and human promoter regions have been previously reported, oligonucleotide primers based on these sequences can be designed for PCR reactions. Long-range PCR can be performed to directly isolate uromodulin promoters from a pool of genomic DNAs extracted from various livestock animal species. DNA fragments containing the uromodulin promoter from livestock animal species can also be identified by hybridization of genomic libraries of corresponding species with mouse, goat, bovine, rat or human uromodulin promoter probes under hybridization conditions similar to or the same as that used for the Southern blots (Zoo-blots of genomic DNA from various species) disclosed in Example 1 provided herein.

As will be appreciated by those in the art, the uromodulin promoter or any other kidney-specific promoter used in the transgene for directing kidney-specific expression of the biologically active polypeptide of interest can include relatively minor modifications, such as point mutations, small deletions or chemical modifications that do not substantially lower the strength of the promoter or its tissue-specificity.

In addition, the identification of additional promoters active in directing gene expression in the kidney can be routinely performed using the suppression subtraction hybridization library technique. Using this technique, which eliminates the cDNAs that are shared by multiple tissues (Diatchenko et al, 1996), a library highly enriched in kidney-specific cDNAs can be generated. Total RNAs are isolated from stomach, intestine, colon, liver and brain, and Northern blot analysis of these mRNAs using an actin cDNA as a probe is used to demonstrate the intactness of the actin mRNA in all of these preparations. Kidney cDNAs are then used as the "tester", and the cDNAs of all the other non-kidney tissues, referred to as the "drivers", are subtracted from the kidney cDNAs. Using the subtraction library technique, the laboratory of the present inventors had earlier probed the cDNAs of the non-subtracted and the subtracted libraries with actin cDNA or uroplakin Ib cDNA, and the results indicated that the original (non-subtracted) bovine bladder cDNA preparation contained abundant actin mRNA and relatively little uroplakin Ib mRNA. In contrast, the subtracted library contained almost no detectable actin mRNA (at least 50 fold reduction) but greatly increased uroplakin Ib mRNA (>10 to 15 fold enrichment). Multiple cDNA clones have been isolated from the subtraction library and used to probe the mRNAs of various bovine tissues. For example, a uroplakin Ib probe confirmed its bladder specificity.

The laboratory of the present inventors have already been successful in obtaining three unidentified cDNAs in which the tissue distribution pattern showed bladder specificity. Sequencing data indicate that these three bladder-specific clones are novel genes not described previously. In the same manner, kidney-specific genes can be isolated, and any gene that is involved in the structure and function of the excretory tract of the kidney, including proximal, distal tubules, Henle's loop, collecting duct system can be applied in this system to isolate its promoter for use in expressing and producing a biologically active protein in a urine-based kidney bioreactor. Although the suppression subtraction hybridization library technique is the preferred procedure for obtaining tissue-specific genes, kidney-specific genes can also be identified through other well-known methods, including biochemical methods, protein chemistry, monoclonal antibody production, two-dimensional gel electrophoresis, cDNA library screening, expression library screening, differential display, phage display, etc.

Although there is an abundance of evidence suggesting that many important regulatory elements are located 5' to the mRNA cap site (McKnight et al., 1982; Payvar et al., 1983; Renkowitz et al., 1984; Karin et al., 1984) and in a great majority of cases the 5'-flanking region is sufficient to convey the tissue-specificity and high-level expression of a tissue-specific gene, it has been reported that in some instances important regulatory elements, particularly those mediating tissue-specific expression, may reside within the structural gene, i.e., introns, or even the 3'- to it in the untranslated sequences, and contribute to promoter activity (Charnay et al., 1984; Gillies et al., 1983; Sternberg et al., 1988). For example, intron I sequences were found to be important for high-level and tissue-specific expression of an α-skeletal actin gene, a β-globin gene and a peripherin gene (Reecy et al, 1998; James-Pederson et al, 1995; Belecky-Adams et al, 1993). In view of these examples of introns or 3'-untranslated sequences contributing to promoter activity, the constructs to be made may include intron I sequences of a kidney-specific gene and, when necessary, 3'-untranslated sequences placed downstream of the DNA sequence encoding the heterologous polypeptide of interest according to the present invention. In the former case, a fragment will be isolated that spans the 5'-flanking region, the first exon and the first intron, followed by the DNA sequence encoding the biologically active polypeptide of interest. The translation initiation codon of the kidney-specific gene could also be mutated to avoid translation of a truncated protein, and other regions of the kidney-specific gene could also be used to ensure the tissue-specific and high-level expression of the transgene.

As used herein, "biologically active polypeptide" refers to a polypeptide/protein capable of causing some effect within an animal and preferably not within the animal having the transgene. Examples of such polypeptides/proteins include, but are not limited to, adipokinin, adrenocorticotropin, blood clotting factors, chorionic gonadotropin, corticoliberin, corticotropin, cystic fibrosis transmembrane conductance regulators, erythropoietin, folliberin, follitropin, glucagon gonadoliberin, gonadotropin, human growth hormone, hypophysiotropic hormone, insulin, lipotropin, luteinizing hormone-releasing hormone, luteotropin, melanotropin, parathormone, parotin, prolactin, prolactoliberin, prolactostatin, somatoliberin, somatotropin, thyrotropin, tissue-type plasminogen activator, vasopressin, antibodies, peptides, and antigens (for use in vaccines). It will be appreciated by those of skill in the art that the above list is not exhaustive. In addition, new genes for biologically active proteins that will function in the context of the present invention are continually being identified.

Proteins which degrade or detoxify organic material may also be produced by means of the present invention. Such proteins may be those discussed in WO 99/28463, the entire contents of which is hereby incorporated by reference.

The biologically active polypeptide produced in the urine-based bioreactor system according to the present invention can be isolated from the urine of these transgenic animals. Accordingly, the present invention provides a means for isolating large amounts of biologically active polypeptides from the urine of transgenic animals which can be used for a variety of different purposes. Furthermore, the biologically active polypeptide can be readily recovered and purified from the urine as would be well within the skill of those in the art.

Because the uromodulin promoter is a preferred promoter for the kidney-based urinary bioreactor system according to the present invention, a transgenic mouse model, in which a mouse uromodulin promoter is operably linked to a DNA sequence encoding human growth hormone, was generated. As described in Example 3, a transgene containing a 3.0 kb mouse uromodulin promoter and 2.1 kb human growth hormone gene was constructed and injected into the fertilized eggs of FVB/N inbred mice. Out of the 42 live-born animals, three animals carried the transgene as evidenced by the appearance of a 5.1 kb transgene fragment in Southern blot hybridization of tail DNA. Upon radioimmunoassay, two of these founder mice were found to secret human growth hormone into the urine. Unexpectedly however, one of the two positive mice that secreted the human growth hormone died at 4 months of age. The remaining positive mouse showed, in addition to urinary hGH, a high concentration of hGH in the serum. These observations, together with the result that the remaining positive male mouse failed to impregnate two batches of female mates strongly indicate that the leakage of hGH into the serum inadvertently affected the physiology and reproductive ability of the founder animals.

Although the adverse effects of leakage of biologically active molecules into the bloodstream have been well documented in the transgenic bioreactor field, definite solutions are scarce, if not nonexistent. The leakage into the bloodstream in transgenic animals can result in severe consequence including the loss of capacity of the bioreactor, rendering it inefficient or inoperable. In the case of urine-based bioreactor, the yield of hGH is compromised; the leakage of hGH into the bloodstream leads to premature death and infertility of the animals. The success of this bioreactor system therefore largely depends upon whether the leakage problem can be solved.

Cell membranes in polarized epithelial cells are functionally divided into apical and basolateral membranes (FIG. 1). The problem of leakage of hGH into the bloodstream is due to the non-directed secretion of hGH into both the apical surface and the basolateral sides of the membrane which are in close vicinity to blood vessels underlying the epithelial cell layer. A unique aspect of the present invention is directed to apical membrane targeting and urinary secretion of the recombinant proteins, which apical targeting minimizes basolateral leakage of the biologically active polypeptide of interest into the bloodstream and thereby also increasing the amount of hGH being secreted into the urine. When a recombinant polypeptide is targeted to the basolateral surface or lacks an apical targeting signal, this protein can be easily leaked into the blood, potentially causing pathological conditions in transgenic animals. Enhanced apical targeting in uromodulin-synthesizing cells will overcome this problem because the recombinant polypeptide will be directly released into the urinary space.

While a great majority of cellular proteins are either secreted or permanently anchored onto the cell membrane, a small group of proteins are temporarily anchored onto the external surface of the plasma membrane via glycolipids. These anchors are termed glycosyl phosphatidylinositols (GPIs) and cleavage of the GPI by phospholipases can release the protein from the membrane. Although the exact function of the GPI linkage is unclear, one of the proposed functions for a GPI sequence is the possibility that GPI serves as an apical targeting signal. A GPI signal sequence usually contains two parts: a stretch of 17–30 hydrophobic amino acids at the very end of the C-terminus of a protein, which will be cleaved and thus be absent in mature proteins, and a shorter stretch (about 8–14 amino acids) containing small amino acids and serving as the GPI anchorage site. GPI structure and the biosynthesis of GPI anchored membrane proteins are reviewed in Englund (1993) and Udenfriend et al. (1995).

Figure 2:
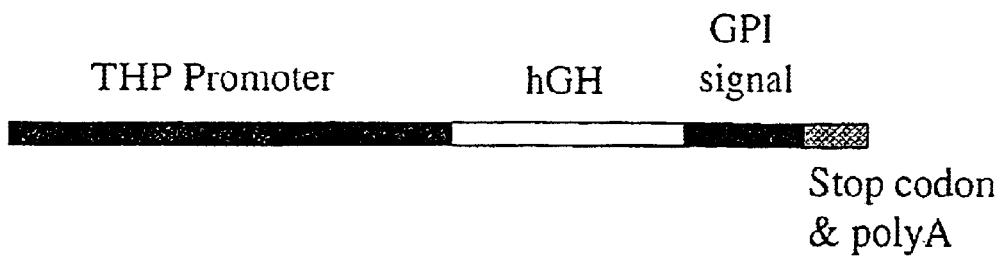
FIG. 2 is a schematic diagram showing an embodiment of a GPI-containing construct. The construct contains, from 5' to 3', the uromodulin promoter, hGH gene, and an in-frame GPI signal sequence followed by a stop codon and polyadenylation signal.

According to a preferred embodiment of the present invention, apical surface membrane targeting is provided by a GPI signal sequence. Therefore, in the present invention, a kidney-specific promoter, preferably the uromodulin promoter, drives the expression of a gene or cDNA encoding a recombinant polypeptide with a GPI signal sequence placed at its C-terminus. This transgene construct will be achieved by constructing from 5'-end to 3'-end, a uromodulin promoter, a DNA sequence encoding a recombinant polypeptide, and a DNA sequence encoding a GPI signal (FIG. 2). This will allow the production of a recombinant polypeptide whose C-terminus is modified with a GPI signal sequence which will be linked with GPI. The GPI sequence can also be located at the N-terminus of the recombinant polypeptide or in the middle of a protein or a fusion protein. With the GPI as an apical targeting signal, the heterologous polypeptide is directed exclusively to the apical surface, instead of to both the apical and basolateral surfaces, where the heterologous polypeptide anchored to the apical membrane will be released into the urine by the action of PIPLC enzyme.

FIG. 3 shows an amino acid alignment/comparison of rat, mouse, human, and bovine uromodulin. At the C-terminus, GPI signal sequence of rat (SEQ ID NO:42), mouse (SEQ ID NO:43), human (SEQ ID NO:44) and bovine (SEQ ID NO:45) are aligned and compared. The underlined sequences denote the GPI attachment site with the GPI addition site most likely being serine. It is clear that there is cross-species conservation of the GPI signal sequences between rat, mouse, human and bovine uromodulin.

Although the GPI signal sequence of uromodulin (THP) is preferred in the transgene construct according to the present invention because uromodulin is naturally targeted to the apical surface and because the uromodulin GPI signal sequence is known to be efficiently cleaved in vivo, GPI signal sequences of other proteins, such as Torpedo acetylcholinesterase (Sikorav et al., 1988; SEQ ID NO:46), placenta alkaline phosphatase (Micanovic et al., 1988; SEQ ID NO:48), *T. brucei* PARP (Clayton et al., 1989; SEQ ID NO:49), hamster prion protein (Stahl et al., 1990; SEQ ID NO:50), rat Thy1 (Seki et al., 1985; SEQ ID NO:51), *T. brucei* VSG (Boothroyd et al.; 1980; SEQ ID NO:52), etc., can be suitably used. In the above-mentioned GPI signal sequences, GPI anchor addition involves the removal of residues C-terminal to residue 13 of SEQ ID Nos: 46–52. It should be noted that even though the GPI signal sequences of these other GPI anchored proteins are not highly sequence conserved, they have structural features that suffice for attachment of the GPI anchor.

An outline of a method for constructing a chimeric polypeptide containing a heterologous polypeptide of interest and GPI signal sequence at its C-terminus is as follows:

1) Creation of a restriction cloning site before the stop codon of hGH by site-directed mutagenesis using the vector containing the uromodulin-hGH construct described in Example 3.

2) Generation of cDNA fragment encoding a GPI-consensus sequence, preferably using the GPI signal sequence of uromodulin. PCR will be performed to amplify a DNA fragment encoding a GPI signal sequence. A restriction cloning site that is identical to the site before the stop codon within hGH will be incorporated into the PCR primers to facilitate cloning, with caution being exercised to ensure that the GPI signal sequence is in the correct translational reading frame with the hGH sequence.

3) Cloning of the DNA fragment encoding the GPI signal sequence into the hGH-encoding DNA sequence.

4) Generation of transgenic mice producing hGH in the urine.

Based on a suitable GPI signal sequence, a universal GPI cassette that is applicable for cloning of a GPI signal sequence at the C-terminus of most, if not all, biologically active polypeptides can be constructed.

An alternative strategy for enhancing the apical secretion of recombinant polypeptides in urine-based kidney bioreactor is to produce a fusion protein between a desired polypeptide and uromodulin. This can be accomplished by constructing a DNA sequence containing the cDNA or gene encoding the desired polypeptide followed by a chemically or enzymatically cleavable linker sequence such as a protease-sensitive linker sequence (e.g., thrombin-sensitive sequence) and by a uromodulin cDNA sequence. This approach has several major advantages. First, since the endogenous uromodulin is predominantly targeted to the apical surface membrane, uromodulin can serve as a carrier for bringing the recombinant heterologous polypeptide to the apical surface. Second, since uromodulin has a tendency to form large, stable aggregates in the urine, the fused polypeptide will likely be more stable in aggregates than as a soluble polypeptide. Third, the aggregated fused polypeptide can be readily purified by first centrifuging the urine to obtain the aggregates, and then cleaving the away the uromodulin portion by using a protease such as thrombin.

The release of uromodulin from the apical membrane into the urine requires the action of the PIPLC enzyme which specifically cleaves the GPI linkage. Likewise, the release of the GPI-linked recombinant polypeptide or recombinant polypeptide-uromodulin fusion protein in uromodulin-synthesizing cells would require a similar mechanism. Although, at the luminal surface of uromodulin-synthesizing cells, there naturally exists functional PIPLC, the amount of the enzyme may not be sufficient to handle large amounts of recombinant polypeptides with a GPI signal sequence. In this respect, overexpression of PIPLC under the direction of a kidney-specific promoter, preferably a uromodulin promoter, will ensure a sufficient amount of PIPLC to efficiently release GPI-anchored recombinant polypeptides from the apical surface. To do this, two constructs, one encoding the recombinant heterologous polypeptide and the other encoding PIPLC, could be co-injected into fertilized eggs to produce an animal bi-transgenic for the recombinant heterologous polypeptide and PIPLC. More likely however, two separate types of transgenic animals instead of a bi-transgenic animal are generated, one of which expresses the recombinant heterologous polypeptide of interest and the other expresses PIPLC. Bi-transgenic animals can then be readily produced by cross-breeding the two separate types of transgenic animals.

Another embodiment of apical surface membrane targeting according to the present invention is to make use of glycosylation of polypeptides as an apical targeting signal. Asn-linked glycosylation has been thought to be a facilitator of apical targeting signal for soluble and membrane proteins in epithelial cells. Although the mechanism is unclear, it has been hypothesized that the glycosylation may serve to interact with lectin-like molecules that are strategically located along the pathway toward the apical surface membrane. By adding one or more non-native glycosylation consensus sequences to a polypeptide which otherwise does not contain a glycosylation site (such as human growth hormone), one could achieve glycosylation, and thereby enhance apical targeting of the polypeptide. The glycosylation consensus sequence is the three amino acid sequence, Asn-Xaa-Ser/Thr, where Xaa can be any amino acid with the exception of proline and aspartic acid. To minimize the number of the amino acid substitutions in a given sequence, a strategy can be employed to introduce a non-native glycosylation site at a sequence containing Asn-Xaa-Xaa (the second Xaa being any amino acid other than Ser/Thr) to Asn-Xaa-Ser/Thr. Alternatively, an original sequence containing Xaa-Xaa-Ser/Thr can be changed to Asn-Xaa-Ser/Thr. To maximize the likelihood of the site being glycosylated, the sites will be designed at β-turns in the structure of the polypeptide, where such non-native sites will have a greater chance of being glycosylated. Globally, the glycosylation consensus sequence can be located at the N- or C-terminus or in the middle of the polypeptide, provided that the mutation of a single amino acid does not impair the original biological function of the polypeptide. For any of the above-mentioned strategies for introducing a glycosylation consensus sequence, any method of site-directed mutagenesis can be performed on cDNA or gene encoding the polypeptide. In order to change a codon encoding any amino acid to Asn (AAU/C), a maximum of 3 point mutations, which can be easily accomplished by routine site-directed mutagenesis, would be required.

In addition to Asn-linked glycosylation, O-glycosylation has been shown to enhance the apical targeting of some epithelial membrane proteins. In general, the sites for O-glycosylation are clusters of serines and threonines (Sadeghi et al., 1999). Proline residues adjacent to serine and threonine residues enhances O-glycosylation (Yoshida et al; 1997). For example, the apical targeting of sucrase isomaltase, an intestinal brush border protein, requires the O-glycosylation of a stretch of 12 amino acids (Ala(37)-Pro (48)) juxtaposed to the membrane anchor. Yoshida et al. (1997) also reported that a sequence stretch containing Xaa-Thr-Pro-Xaa-Pro appears to be a good substrate for O-glycosylation. Accordingly, the Xaa-Thr-Pro-Xaa-Pro sequence stretch can also be introduced into the heterologous polypeptide of interest by site-directed mutagenesis.

An alternative strategy to produce a higher level of PIPLC than is normally produced in uromodulin-synthesizing kidney epithelial cells is to construct a DNA molecule in which a DNA sequence encoding PIPLC is placed 3' (downstream from) of a construct where a kidney-specific promoter is operably linked to a DNA sequence encoding a heterologous polypeptide. The placement of the DNA sequence encoding PIPLC allows the kidney-specific promoter to be operably linked to both the DNA sequence encoding the heterologous protein and the DNA sequence encoding PIPLC. Thus, "bi-cistronic" mRNA can be transcribed from this particular type of construct.

An alternative to apical targeting by the addition of GPI or by glycosylation is the inactivation of potential basolateral targeting signals that are present in the heterologous polypeptide of interest. It has been reported that, in some instances, basolateral targeting depends on a distinctive cytoplasmic targeting signal, for example a tyrosine motif or a di-leucine motif.

The so-called tyrosine motif for basolateral targeting contains a consensus sequence YXXO where the first residue (Y) is tyrosine, the last amino acid (denoted by 0) is a bulky hydrophobic amino acid residue (most commonly Leu), and the middle two residues can be any amino acid residue (Deschanbeault et al., 12991; Stephens et al., 1998). A double or di-leucine motif is also important for basolateral targeting. This motif is basically two (double) leucine residues (di-leucine; Hunziker et al., 1994). The tyrosine and di-leucine motifs are found frequently at the C-terminus of the protein or in the cytoplasmic domain of a membrane protein. Deletion or modification of these motifs will likely lead to the blockage of basolateral targeting. Experimental strategies to be-employed in this alternative to apical targeting include the removal of a segment at the C-terminus of a heterologous polypeptide that contains a basolateral targeting signal sequence, or the mutation of tyrosine and di-leucine motifs contained in basolateral targeting signal sequences on the heterologous polypeptide, such as by site-directed mutagenesis of the encoding DNA sequence.

As will be appreciated by those in the art, any combination of the aforementioned targeting approaches can be used. For example, the GPI and glycosylation approaches can be employed simultaneously, or the addition of GPI and/or glycosylation can be combined with the deletion/inactivation of basolateral targeting signal(s). Furthermore, these targeting approaches are not limited to targeting the apical surface membranes of kidney epithelial cells and are believed to also be applicable to other bioreacteor systems such as the mammary gland, urothelial, and seminal bioreactor systems.

While the production of transgenic animals by the introduction of the transgene into germ line cells is most preferred, it is also contemplated that the transgenic animals, which serve as a urinary bioreactor system, can be generated with vectors that are useful for transforming the kidney into a bioreactor capable of producing a biologically active protein in the urine for isolation. The transformed cells may be germ line or somatic cells.

In an alternative embodiment to introduction into germ line cells, the vector according to the present invention includes a system which is well received by the cells lining the excretory tract of the kidney, including proximal, distal tubules, Henle's loop and collecting duct system. An example of a useful vector system is the Myogenic Vector System (Vector Therapeutics Inc., Houston, Tex.). In this embodiment, the heterologous DNA sequence encoding the biologically active polypeptide, linked to a viral promoter construct capable of directing kidney-specific expression and carried in the vector, is introduced into the kidney of an animal in vivo. Introduction of the vector can be carried out by a number of different methods routine to those of skill in the art. Vectors of the present invention can also be incorporated into liposomes and introduced into the animal in that form. The transgene is absorbed into one or more epithelial cells capable of expressing and secreting the biologically active protein into the urine collecting in the bladder.

Another alternative embodiment for generating a transgenic animal as a kidney-based bioreactor is through the use of targeted homologous recombination, where one copy of the endogenous uromodulin gene is disrupted by insertion of a heterologous gene encoding a biologically active molecule of interest, which heterologous gene is flanked by sequences complementary to the endogenous uromodulin gene. These flanking complementary sequences which direct homologous recombination to an endogenous uromodulin gene are at least 25 base pairs in length, preferably at least 150 base pairs. This technique for generating transgenic animals and cells by homologous recombination is disclosed in WO 90/11354 and U.S. Pat. No. 5,272,071, the entire contents of which are hereby incorporated by reference. Accordingly, if it is desired for the kidney to express and secrete a selected biologically active polypeptide into the urine, then a short sequence on either side of the start codon of the uromodulin coding sequence in a given species can be used as flanking sequences to create a construct that can be inserted at the specific location in the genome of the host animal species which is between the endogenous uromodulin gene promoter and the endogenous uromodulin gene coding sequence. In this way, the expression of the biologically active polypeptide of interest will be driven by the endogenous uromodulin promoter in the transgenic animal. The bovine genomic uromodulin sequence has already been reported (Yu et al., 1994), and the mouse genomic uromodulin sequence as well as the clone containing the goat genomic uromodulin gene sequence surrounding the start codon are disclosed herein.

Having now generally described the invention, the same will be more readily understood through reference to the following examples which are provided by way of illustration and are not intended to be limiting of the present invention.

EXAMPLE 1

Isolation of Mouse Uromodulin Gene Promoter
Generation of Uromodulin cDNA Probes Three probes corresponding to the 5'-end, the middle region and the 3'-end of the full-length uromodulin cDNA (Prasadan et al, 1995) were generated using the reverse transcription-polymerase chain reaction (RT-PCR) method, with three pairs of oligonucleotide primers chemically synthesized based on the published uromodulin cDNA sequence. The set of primers for the 5'-end are 5'-TGGACCAGTCCTGTCCTGGTTCAG-3' (SEQ ID NO:5; sense), and 5'-GGGTGTTCACACAGCTGCTGTTGG-3' (SEQ ID NO:6; antisense). The set of primers for the middle region are 5'-AGGGCTTTACAGGGGATGGTTG-3' (SEQ ID NO:7) and 5'-GATTGCACTCAGGGGGCTCTGT-3' (SEQ ID NO:8) The set of primers for the 3'-end are 5'-GGAACTTCATAGATCAGACCCGTG-3' (SEQ ID NO:9) and 5'-TGCCACATTCCTTCAGGAGACAGG-3' (SEQ ID NO:10). These three pairs of oligonucleotide primers were used to amplify uromodulin cDNA fragments using, as a template, a pool of cDNAs reversed transcribed from mouse kidney RNAs. PCR conditions included the first cycle of 94° C. for 1 min, 55° C. for 1 min, and 72° C. for 2 min; 35 cycles of 95° C. for 2 min, 55° C. for 1 min, and 72° C. for 2 min; and the last cycle of 94° C. for 2 min, 55° C. for 1 min, and 72° C. for 8 min. Agarose gel electrophoresis revealed a 400 bp, a 440 bp and a second 400 bp PCR product for the three sets of primer amplifications, 5'-end, middle region, and 3'-end, respectively. These PCR products were purified by extraction and chromatography using a QIAEX II method (QIAGEN, Valencia, Calif.).

Screening of Mouse Kidney cDNA Library

Figure 4:
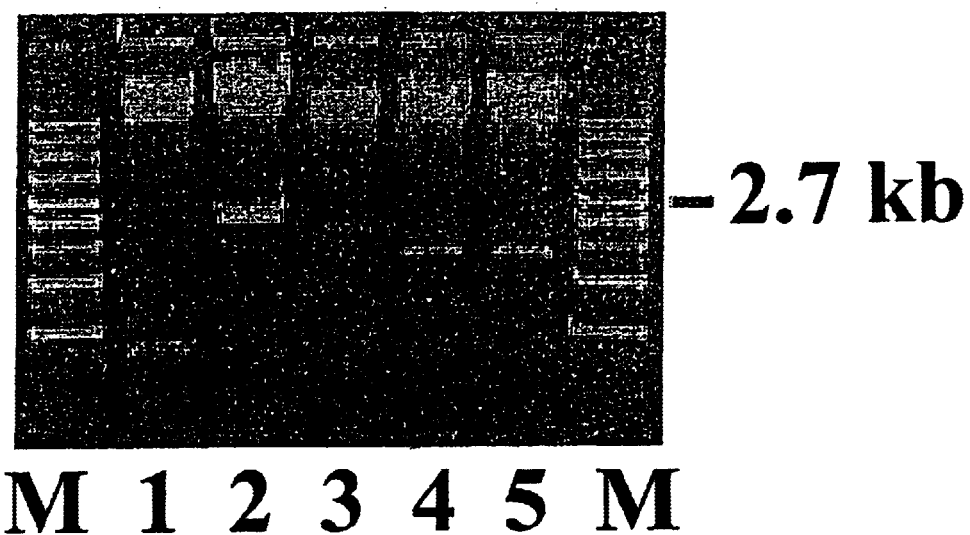
FIG. 4 shows a restriction digestion of five phage clones (lanes 1–5) on agarose gel electrophoresis. M represents lanes of molecular weight markers.
Figure 5:
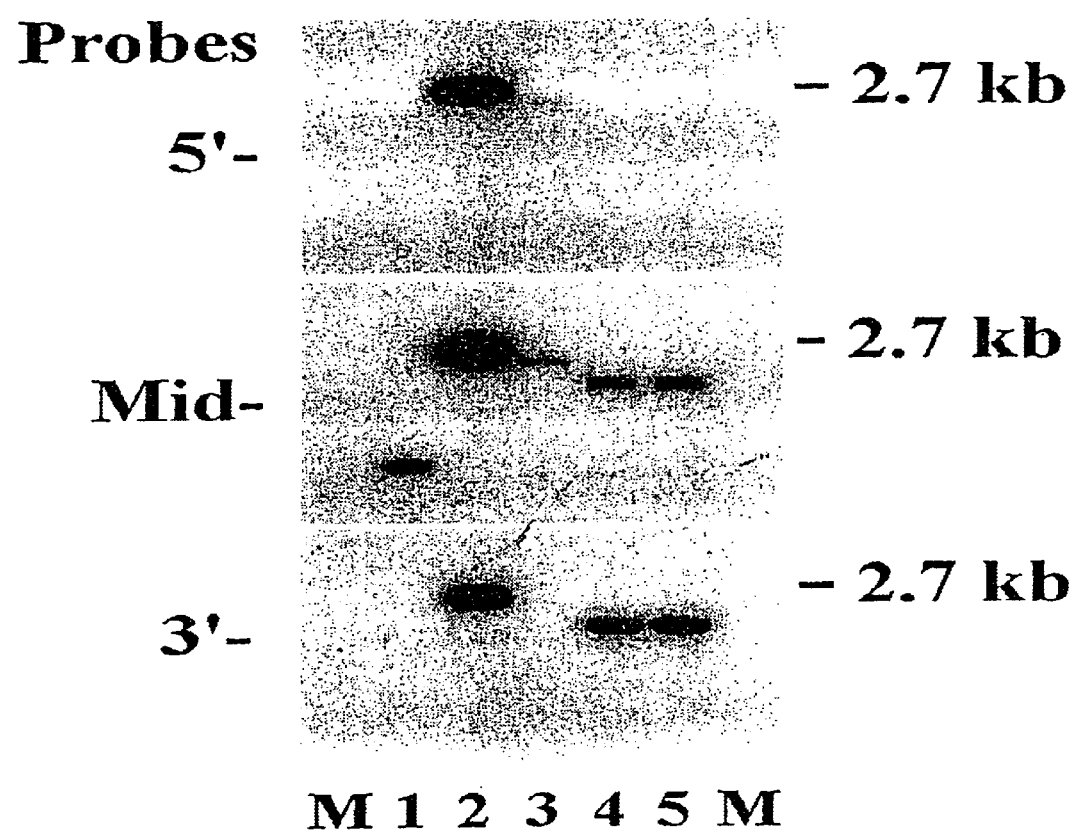
FIG. 5 shows a Southern blot corresponding to the agarose gel shown in FIG. 4 hybridized separately with each of the 5'-end, middle region, and 3'-end probes.

A mixture of the above three uromodulin cDNA probes were $^{32}$P-labeled and used to screen a BALB/c mouse kidney cDNA library (Clontech, Palo Alto, Calif.). A total of $2\times10^5$ phage clones from the cDNA library were plated, lifted onto nylon membrane and hybridized with the mixture of probes at 42° C. for 16 hours in a solution containing 50% Formamide, 5×SSPE, 5× Denhardt's solution, 0.1% SDS and 100 mg/ml denatured salmon sperm DNA. After hybridization, the nylon filters were washed at 65° C. for 1 hour in 1×SSC and 0.1% SDS, and autoradiographed. Five phage clones were identified from the primary screening, and they were plaque-purified and subjected to the secondary screening using the same conditions as the primary screening. Purified phage clones were amplified by plate lysate and analyzed by EcoRI restriction digestion and agarose gel electrophoresis. On agarose gel, the five clones are of different sizes, ranging from 0.2 kb to 2.7 kb (FIG. 4). A 2.7 kb clone hybridized with all three probes indicating that this band likely represented the full-length mouse uromodulin cDNA clone (FIG. 5). This 2.7 kb band was excised from the bacteriophage with EcoRI restriction enzyme, gel-purified, subcloned into the same site of pBluescript KS$^+$ (Stratagene, LaJolla, Calif.), and sequenced. The sequence matched precisely with the published mouse (uromodulin cDNA sequence of Prasadan et al, 1995), further establishing the authenticity of this as mouse uromodulin.

Isolation of Mouse Uromodulin Gene

Figure 6:
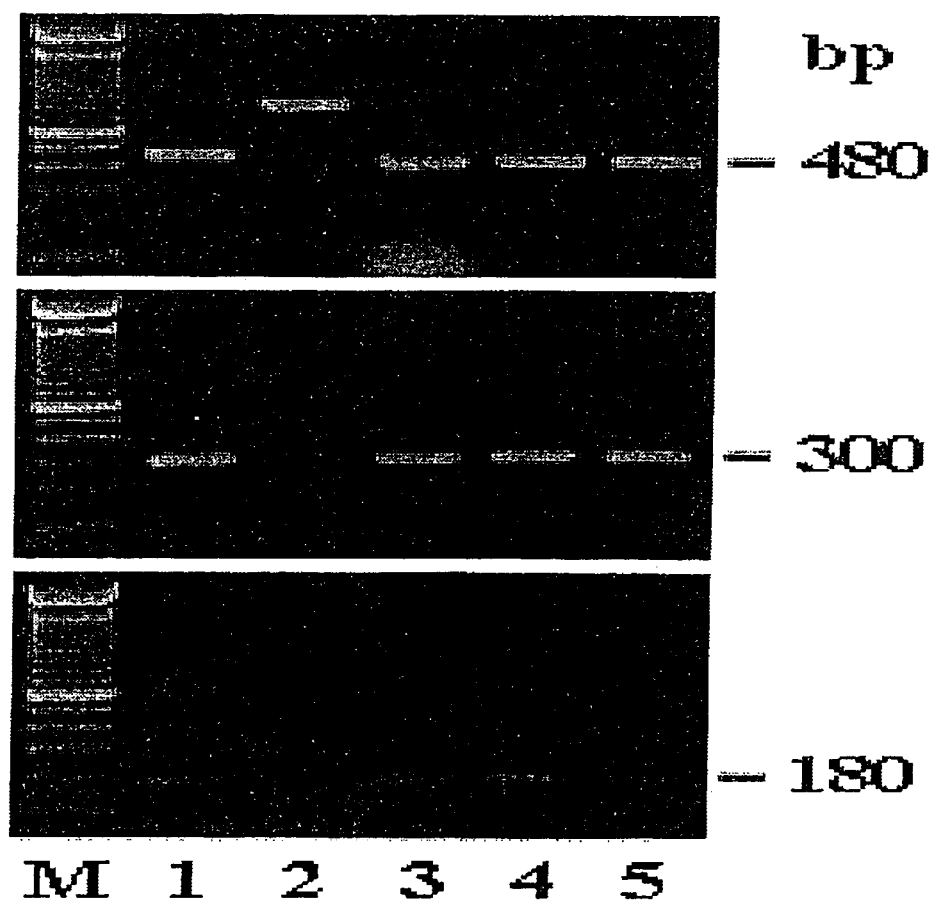
FIG. 6 shows an agarose gel electrophoresis of PCR reaction products using the sets of primers for the 5'-end, the middle region, and the 3'-end of the uromodulin gene.

For the isolation of the mouse uromodulin gene, a commercial genomic screening service (Genomic System, St. Louis, Mo.) was used. Briefly, two pairs of PCR primers located in exon 3 (exon information derived from human uromodulin gene, Pennica et al, 1987) were designed and pre-tested by the present inventors. These primers were then used by Genomic System to mass-screen by PCR pooled genomic (BAC) plasmid clones of the MAC ES Mouse II library which harbors 129/SVJ mouse genomic DNAs. The first pair of primers, sense 5'-AGGGCTTTACAGGGGATGGTTG-3' (SEQ ID NO:11), and antisense 5'-GATTGCACTCAGGGGGCTCTGT-3' (SEQ ID NO:12), was used for the initial screen which yielded two uromodulin clones, each about 60–70 kb in length. These clones were confirmed independently by using a second set of nested primers, sense 5'-GCCTCAGGGCCCGGATGGAAAG-3' (SEQ ID NO:13) and antisense 5'-GCAGCAGTGGTCGCTCCAGTGT-3' (SEQ ID NO:14). In addition, PCR reactions using the three pairs of primers located at the 5'-end, the middle region and the 3'-end (SEQ ID NOs:5–10) showed that these two clones contained all the coding sequence information, indicating that it contained the entire uromodulin gene (FIG. 6).

Identification of the Uromodulin Gene in Multiple Animal Species

Figure 7B:
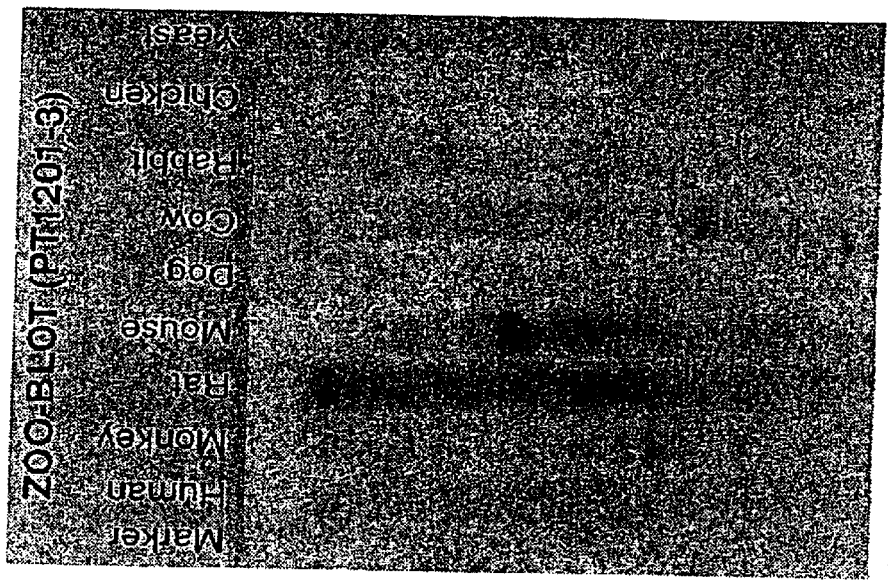
FIGS. 7A and 7B show agarose gel electrophoresis (FIG. 7A) of EcoRI restriction digests of genomic DNA from various animal species and Southern blot hybridization (FIG. 7B) of the restriction digested genomic DNA with the middle region probe.
Figure 7A:
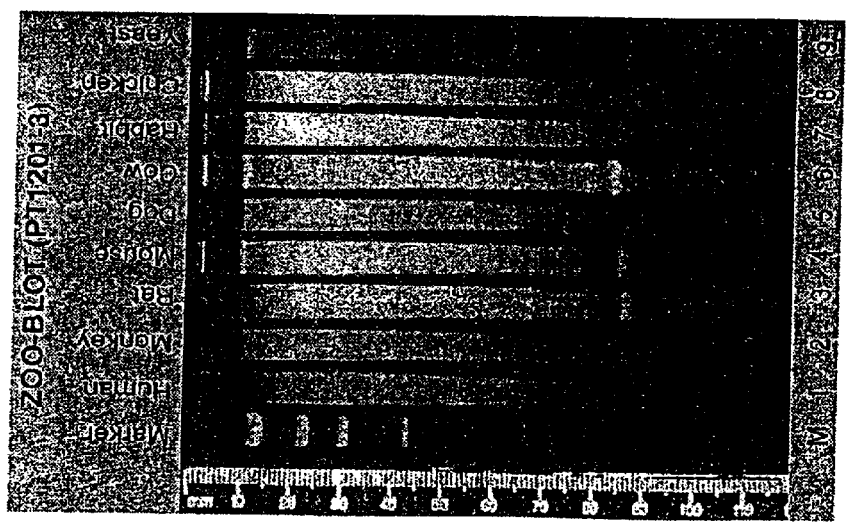
Figure 8:
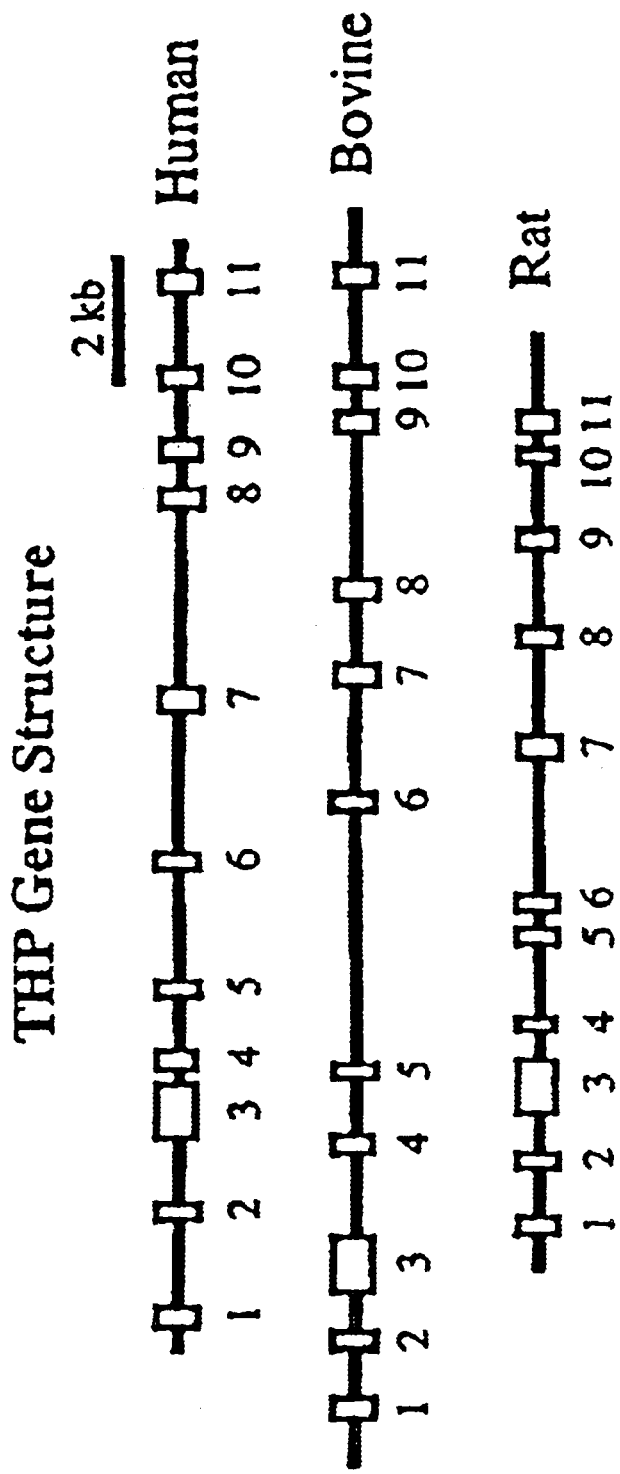
FIG. 8 is a schematic representation of the uromodulin (THP) gene structure in the human, bovine and rat genome. The open boxes represent exons with the exon numbering provided, and the thick bars represent the introns, the lengths of which are variable.

An analysis of the conservation of the uromodulin gene sequence in other animal species is shown in FIGS. 7A and 7B. The genomic DNA of human, monkey, rat, mouse, dog, cow, rabbit, chicken and yeast were digested with EcoRI restriction enzyme and hybridized with the uromodulin middle region probe described above, using the same Southern blot hybridization conditions used above for screening the mouse kidney cDNA library. The results of the Southern blot hybridization shown in FIG. 7B show that the uromodulin gene is conserved in mammals and is present as a single copy in human, monkey, rat, mouse, dog, cow and rabbit. Pennica et al (1987) and Yu et al (1994) reported that the gene structure (exons and introns) of human, bovine and rat uromodulin are highly conserved (FIG. 8).

Identification of Gene Fragments Containing the Mouse Uromodulin Gene Promoter

Figure 9:
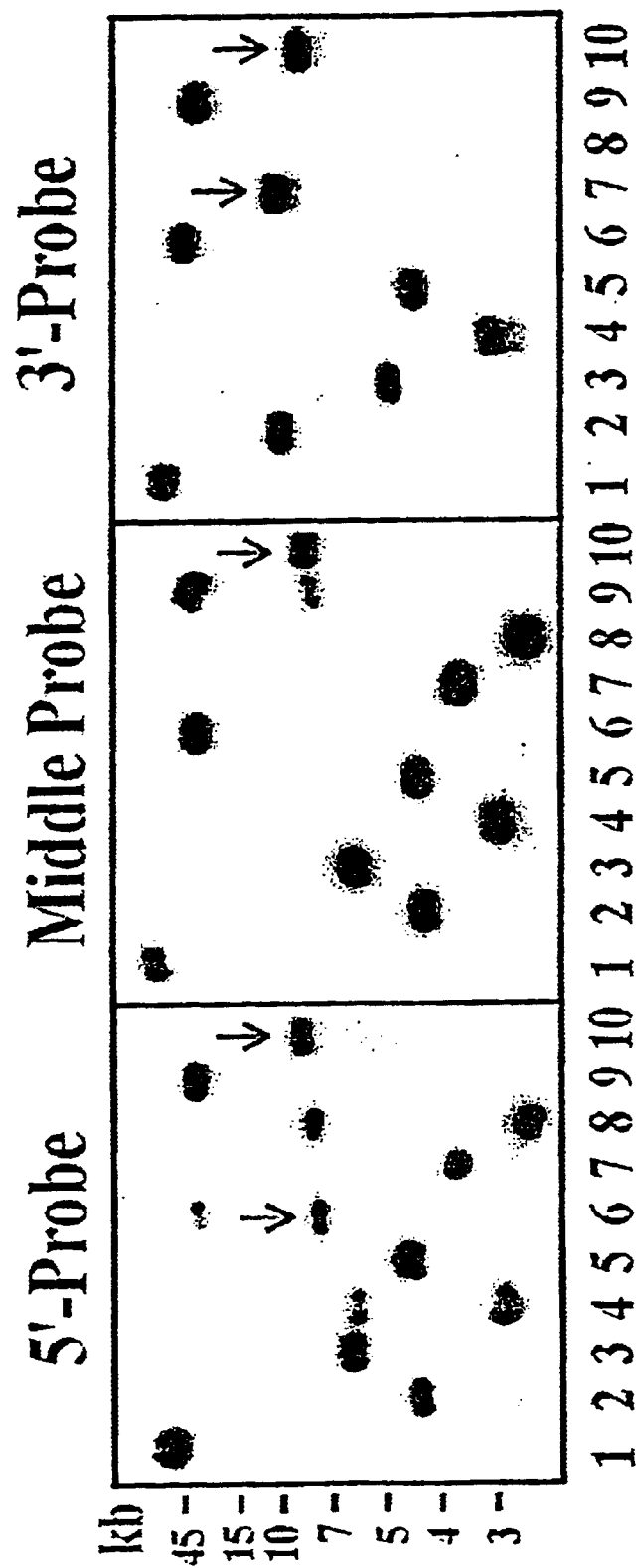
FIG. 9 shows Southern blot hybridization of BAC plasmid clone 1 digested with the restriction enzymes, PstI (lane 4), ApaI (lane 6), EcoRI (lane 7), SacI (lane 8), and KpnI (lane 10) and hybridized separately with 5'-end, middle region and 3'-end probes.

Southern blotting was performed to identify DNA fragments containing the uromodulin promoter sequence. This approach is based on the differential reactivity of DNA restriction fragments of BAC clone 1 DNA with three different uromodulin probes located in the 5'-end, middle region, and 3'-end of the uromodulin cDNA. Thus, BAC plasmid clone 1 was digested with the restriction enzymes NotI, BamHI, HindIII, PstI, EcoRI, ApaI, NcoI, SacI, XhoI and KpnI. After agarose gel electrophoresis, DNA fragments were transferred onto nylon membrane, UV-crosslinked and hybridized with the 5'-end, middle region, and 3'-end cDNA probes. A 6.9 kb PstI DNA fragment (FIG. 9, lane 4), an 8.3 kb ApaI DNA fragment (FIG. 9, lane 6), and an 8.5 kb SacI DNA fragment (FIG. 9, lane 8) reacted with only the 5'-end probe, but not with middle region probe or the 3'-end probe. This strongly indicates that these three DNA fragments contain portions of the 5'-end of the uromodulin coding sequence and, more importantly, a large fragment of the 5'-upstream region of the mouse uromodulin gene. In contrast, a 9 kb KpnI fragment reacted with all three probes (FIG. 9, lane 10), indicating that this fragment contains all the coding sequences for mouse uromodulin. Finally, a 10 kb EcoRI fragment reacted only with the 3'-probe (FIG. 9, lane 7), indicating that this fragment contains the 3'-end of the coding region and the non-coding region. The identification of DNA fragments containing the entire mouse uromodulin gene, particularly the 5'-upstream sequence facilitates the cloning of the uromodulin gene promoter.

Sequencing of Mouse Uromodulin Promoter

The 8.3 kb ApaI DNA fragment was used for further promoter analysis. A genomic walking method was employed to sequence the entire mouse uromodulin promoter from both 5'- and 3'-ends by sequentially walking the sequence and synthesizing the new primers based on newly obtained sequences. Sequences were determined by the dideoxynucleotide chain termination method of Sanger et al (1977) on an automatic DNA sequencer. Listed below are sense- and anti-sense primers used for the sequencing purposes.

Sense Primers

S1: 5'-TGTCCTATGTGACTCCAGCT-3' (SEQ ID NO:15)

S2: 5'-TCTCCTCAGCTCTCCTGGTC-3' (SEQ ID NO:16)

S3: 5'-TCCTGCCACCACCATGACCA-3' (SEQ ID NO:17)

S4: 5'-AAGCACCGGTGTGCTTGTAT-3' (SEQ ID NO:18)

S5: 5'-ATGGGGCTGCTGAGACTAAG-3' (SEQ ID NO:19).

Anti-sense Primers

AS1: 5'-AAGTCAGACTGTGTTAGGAT-3' (SEQ ID NO:20)

AS2: 5'-ATTGACTGAGCAGGAAGCAT-3' (SEQ ID NO:21)

AS3: 5'-ATTTTATAACCTCCCTCTAG-3' (SEQ ID NO:22)

AS4: 5'-ATGCATTCCAGTCTCAGTGC-3' (SEQ ID NO:23)

AS5: 5'-TGGGGAGAGGACAAAGCCTTG-3' (SEQ ID NO:24)

AS6: 5'-TGACGTGCCAACTCCACTGA-3' (SEQ ID NO:25)

AS7: 5'-AGGACCTGTAGGGTAAGAAA-3' (SEQ ID NO:26)

AS8: 5'-TCTGGCTGTGGGCTCTATAT-3' (SEQ ID NO:27).

Analysis of the Mouse Uromodulin Promoter

The 9,345 bp nucleotide sequence of the promoter region and the genomic coding region including exon 3 of the mouse uromodulin gene is shown in FIG. 10. These results (1) establish the authenticity of the isolated uromodulin clone, (2) indicate that a 7 kb uromodulin promoter has been obtained which is more than adequate to be used in the urine-based transgenic bioreactor system. This mouse promoter can be used in other mammalian species, such as farm animals, to drive the kidney-specific expression of any heterologous gene.

Subcloning of Mouse Uromodulin Promoter

Having identified the mouse uromodulin promoter region, this region can be subcloned for further amplification, and for constructing transgenes. Since the clone containing the uromodulin promoter region is at least 70 kb in size, restriction digestion of each of this clone gives rise to multiple bands. Although the relative sizes of uromodulin promoter-containing bands can be determined by Southern blotting using the 5'-end probe, this does not allow for pinpointing a specific band for subcloning, as most bands are not well-resolved. To circumvent this problem, a dot-blot approach by gel-purifying each individual band in the close vicinity of the area where Southern blot hybridization revealed a positive band will be taken. DNA in each band will be eluted using a QIAEX column (QIAGEN), and then blotted onto nylon membrane, UV-crosslinked and hybridized with a uromodulin 5α-probe. The bands reacting with the probe will then be subjected to subcloning.

The plasmid pBluescript (Stratagene, LaJolla, Calif.), which was used as the cloning vector, is to be restriction-digested using PstI, ApaI and SacI, respectively, phosphatase-treated, and the linearized pBluescript cloning vectors will be mixed with the correspondingly digested inserts, ligation buffer, T4 DNA ligase, and incubated at 16° C. for 16 hours. Half of this ligation mixture will be used to transform CaCl₂-prepared competent JM109 bacterial cells and then screened using small-scale plasmid preparations, which are carried out using mini-prep columns (Promega) and then restriction-digested to release the inserts. Through these procedures, the DNA fragments containing mouse uromodulin promoter are to be subcloned.

Detailed Restriction Mapping of Mouse Uromodulin Promoter

Restriction mapping of the 5'-flanking sequence of uromodulin, an important step for determining the restriction fragments for constructing transgenes has been performed. Although the detailed restriction map is not shown here, such a restriction map can be generated quite readily using any of the numerous publicly or commercially available DNA analysis software programs. A schematic presentation of the mouse uromodulin promoter with several restriction sites denoted is shown in FIG. 11.

EXAMPLE 2

Isolation of Goat Uromodulin Gene Promoter

Isolation of Goat Uromodulin cDNA

The goat uromodulin cDNA was isolated using reverse transcriptase/polymerase chain reaction (RT-PCR) approach (Wu, et al., 1993). Briefly, a sense and an antisense primer were synthesized based on the mouse uromodulin gene sequence that was isolated in the laboratory of the present inventors. The sequences of these two primers are: 5'-GACTGAGTACTGGCGCAGCACAG-3' (SEQ ID NO:28) and 5'-GATTGCACTCAGGGGGCTCTGT-3' (SEQ ID NO:29). Total RNA was isolated from goat kidneys using the guanidine isothiocyanate method, reverse-transcribed using AMV reverse transcriptase, and the second strand of cDNA was synthesized using DNA polymerase I. PCR amplification was performed using total kidney cDNAs as templates and the two mouse uromodulin as primers, in the presence of dNTP, Taq polymerase, and PCR buffer. The PCR reaction was performed for 35 cycles of denaturation at 94° C., annealing at 55° C. and extension at 72° C. and the resulting PCR products were resolved by agarose gel. The products having the predicted size were subcloned into the TA cloning vector (Invitrogen, Carlsbad, Calif.) and sequenced.

RT-PCR of goat kidney-derived mRNAs, using the pair of primers derived from mouse uromodulin, yielded a single, approximately 300 bp product upon agarose gel electrophoresis. The PCR product was subcloned and sequenced. A Blast search of Genbank of the PCR product sequence (SEQ ID NO:2; FIG. 12) showed that the top four hits were uromodulin sequences from several species. Thus, the sequence of the PCR product shared a 96% identity (287 bp/297 bp) with bovine uromodulin, 90% identity (218/241) with human uromodulin, a 78% identity (239/304) with rat uromodulin, and an 80% identity in a shorter stretch (125/156) with mouse uromodulin. The high degree of sequence identity of the PCR product with known uromodulin sequences firmly established that the product is a partial goat uromodulin cDNA.

Isolation of Goat Uromodulin Genomic DNA By Genomic Walking, Cloning and Sequencing A genomic walking approach was employed to isolate the goat uromodulin gene using specific sequence information obtained from goat uromodulin cDNA. Genomic DNA was isolated from goat kidneys and used as templates for PCR-based genomic walking (Clontech, Palo Alto, Calif.). The genomic DNA was digested using five restriction enzymes (DraI, ScaI, EcoRV, PvuII, StuI), each of which created a blunt end in the genomic DNAs. The ends were ligated with adaptors. PCR was then performed using the ligated DNA library as templates, and two independent anti-sense primers synthesized based on the newly obtained uromodulin cDNA sequence as well as a sense primer located on the adaptor. The sequences for the two anti-sense primers are 5'-GTACCAGCCGCCCAGACTGACATCACAG-3' (SEQ ID NO:30; primer AS14), and 5'-CAGGTTGTACACGTAGTAGCCGCCGGCA-3' (SEQ ID NO:31; primer AS17). The PCR was performed for 1 cycle of denaturation at 99° C. for 5 sec, annealing and extension at 68° C. for 4 min., followed by 7 cycles of denaturation at 94° C. for 2 sec, annealing and extension at 68° C. for 4 min., followed by 32 cycles of denaturation at 94° C. for 2 sec, annealing and extension at 63° C. for 4 min., and followed by 1 cycle at 63° C. for 4 min. After the first round of PCR, the products were used as templates and subjected to a second round of PCR amplification using two new, nesting sense and anti-sense primers. The specific products were subcloned into the TA cloning vector and the identity of the goat uromodulin gene was confirmed by DNA sequencing of both ends of the product.

Based on the newly identified goat uromodulin cDNA, the two above anti-sense primers were designed for genomic walking using goat genomic DNA to identify DNA sequences that are located in the upstream region. After the first and second rounds of PCR and nesting PCR amplifications, a 1.5 kb, single PCR product was obtained. Subcloning and sequencing of this product revealed that its 3'-end shares 94% identity (494/522) with bovine uromodulin cDNA sequence, thus confirming that the PCR product is a portion of the goat uromodulin gene. The 5'-sequence did not share any significant homology with any of the known uromodulin cDNA sequences and therefore most likely represents intron sequences. Based on the gene structure of mouse uromodulin and the relative length (1.5 kb) of the PCR product, this 5'-sequence is most likely located in intron 1. The nucleotide sequences of intron 1 (SEQ ID NO:3) and exon 3 (SEQ ID NO:4) of the goat uromodulin gene are shown in FIGS. 13A and 13B, respectively.

Isolation of Goat Uromodulin Promoter by Secondary Genomic Walking

For the isolation of goat uromodulin promoter, the 5'-end of the genomic clone that was isolated from the first round of genomic walking was used to design new antisense "walking primers" located in intron 1. The five primers are:

5'-AAGATTTACCAGCCCGGGCCGTCGACC-3' (SEQ ID NO:32; AS1)

5'-AATAAAGTGCCAGGGCAGGGGGGCTTA-3' (SEQ ID NO:33; AS2)

5'-CTTGTGTGGTTGAGTGTGTTCTTGACC-3' (SEQ ID NO:34; AS3)
5'-TGTGAAAGGGGATGTCTTTGGGTACCA-3' (SEQ ID NO:35; AS4)
5'-ACAGCAATGTGCAACCCAATGGAAGGG-3' (SEQ ID NO:36; AS5).

Fresh goat genomic DNA as template was digested by the five blunt-ending restriction enzymes (see above) and subjected to PCR walking using these five anti-sense primers and the aforementioned conditions.

PCR and nesting PCR yielded a highly specific, 1.0 kb product in three independent primer combinations. A further round of genomic walking resulted in a 1.6 kb fragment which was subcloned as smaller fragments. Subcloning and DNA sequencing of the subcloned fragments provided the 1.6 kb goat uromodulin promoter sequence of SEQ ID NO:37 and its structural features as shown in FIGS. 14A and 14B. A computer comparison/alignment of the nucleotide sequences of the mouse and goat uromodulin promoter regions is presented in FIGS. 15A and 15B.

EXAMPLE 3

Construction of Kidney-Based Bioreactor System
Construction of Chimeric Genes

To test the tissue-specificity of the uromodulin gene promoter and its utility in a kidney-based bioreactor system, a chimeric gene containing a uromodulin promoter and a gene encoding a pharmaceutically-important protein is to be constructed. For this purpose, human growth hormone (hGH), whose expression has been recently assessed in a uroplakin II-based, bladder bioreactor system (Kerr et al, 1998) will be tested first. A potential limitation has been recognized with the bladder bioreactor system in that it produced relatively low amounts of hGH. Such a potential limitation may possibly be associated with the less than optimal secretory activity of the urothelium. Since uromodulin is normally synthesized in the ascending limb of Henle's loop and the distal tubules where active secretion takes place, the present inventors expect that there will be an active secretion of synthesized hGH into the urine of mice, resulting in high protein yield. The presence of this uromodulin/hGH gene in transgenic mice will allow a comparison of the efficiency between the kidney-based and the bladder-based reactor systems.

Figure 16:
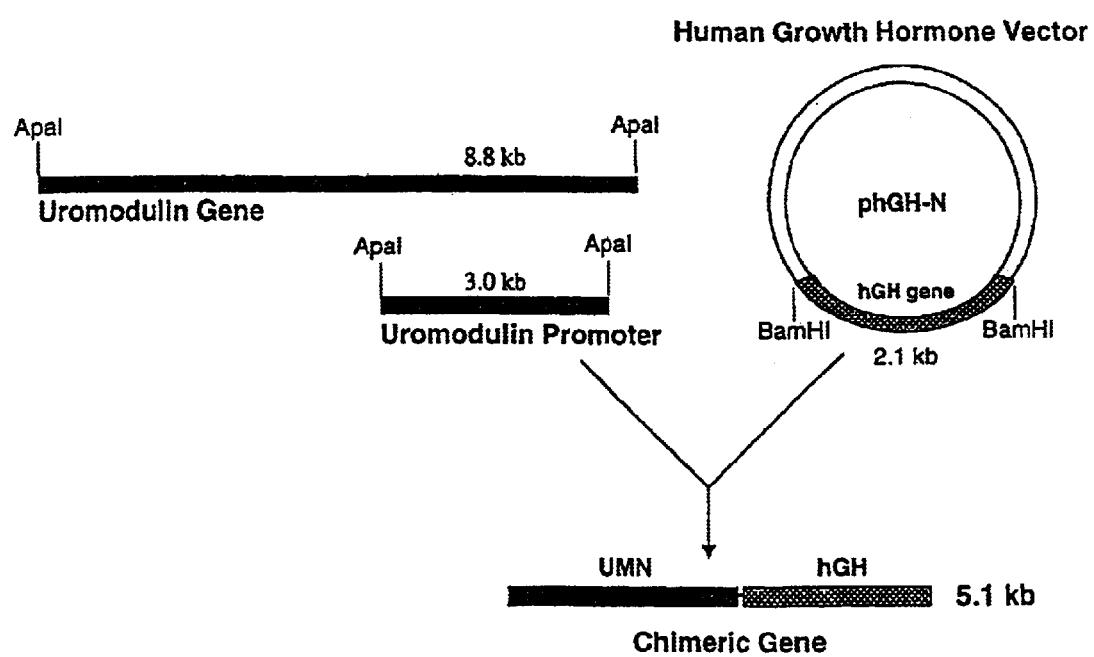
FIG. 16 is a schematic diagram illustrating the construction of chimeric gene with a mouse uromodulin promoter and the coding sequence of human growth hormone. A 3.0 kb 5'-upstream sequence of the mouse uromodulin gene was cloned upstream of a 2.1 kb human growth hormone coding sequence.

An 8.8 kb genomic fragment containing the 5'-upstream region of the mouse uromodulin gene was used as a template for PCR amplification to yield a 3.0 kb uromodulin promoter fragment. PCR sense (SEQ ID NO:53) and antisense (SEQ ID NO:54) primers were designed so that their ends included an ApaI enzyme cleavage site to facilitate cloning. The 3.0 kb PCR fragment was subcloned into the ApaI site of the pBluescript vector. A 2.1 kb genomic fragment of human growth hormone gene (Genbank accession number M13438 for complete coding sequence of hGH) containing the entire coding sequences was excised from phGH-N vector (obtained from Brian M. Shewchuk, Department of Genetics, University of Pennsylvania, Philadelphia, Pa.), gel-purified and subcloned into the BamHI site of the above-mentioned pBluescript vector so that human growth gene is positioned downstream of the mouse uromodulin promoter (FIG. 16). The correct orientation of the chimeric gene was verified by restriction digestion and DNA sequencing. The uromodulin-hGH chimeric gene was retrieved en bloc by restriction digestion using KpnI and XbaI. The 5.1 kb fragment was resolved by agarose gel electrophoresis, electroeluted and dialyzed extensively against Tris-EDTA buffer. The purified chimeric gene was then microinjected into the fertilized eggs of FVB/N inbred mice and implanted into the uteri of pseudopregnant mice as previously described by Brinster et al. (1981).

Figure 17:
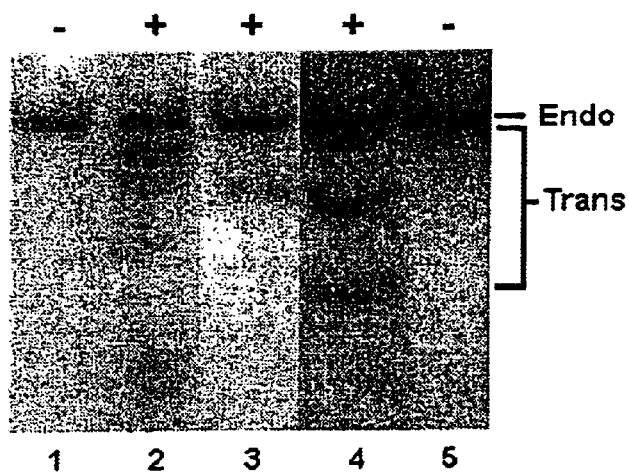
FIG. 17 shows a Southern blot analysis of mouse tail DNA of founder mice. Lanes 1 and 5 are non-transgenic control mice showing the endogenous fragment (Endo) of uromodulin coding sequence that hybridized with the uromodulin probe.

Southern blotting was employed to identify transgenic mice harboring the chimeric uromodulin-hGH gene. DNA was extracted from mouse tail using proteinase K digestion and NaCl precipitation. The DNA was digested with BglII, electrophoresed and transferred onto nylon membrane and hybridized with a 500 bp probe located at the 3'-end of the uromodulin promoter (FIG. 17). Out of 42 live-born animals, three carried the transgene as evidenced by the appearance of a 5.1 kb transgene fragment in the Southern blot of mouse tail DNA (FIG. 17). In FIG. 17, lanes 1 and 5 are non-transgenic control mice showing the endogenous fragment (Endo) of uromodulin gene, transgene fragments (Trans), in mouse 2 (15 kb), mouse 3 (9 kb) and mouse 4 (5.5 kb and 4.9 kb). These different fragment sizes may reflect the particular transgene orientation and the chromosomal site of transgene integration.

Expression of hGH in Mouse Kidney

The expression of hGH in transgenic mouse kidney is to be assessed at both the mRNA and protein levels. RT-PCR will be performed to determine the expression of mRNA using primers specific for hGH. Total RNAs will be extracted from transgenic mouse kidneys and from control tissues, including rat liver, skin, intestine, stomach, brain, skeletal muscle, thymus, thyroid gland, bladder, lungs, heart, pancreas, spleen, prostate, seminal vesicles, uterus and ovaries. The total RNAs are to be reverse-transcribed, PCR amplified and analyzed by agarose gel electrophoresis. The results will reveal whether hGH is expressed in kidney-dependent fashion. To determine whether hGH was synthesized in the ascending limb of Henle's loop and the distal tubules of the kidney, immunofluorescent staining of the kidney using anti-hGH antibody will be performed. Frozen kidney sections are to be stained using an indirect immunofluorescent method (Wu et al, 1993).

The laboratory of the present inventors have now performed radioimmunoassays (RIA) to determine the level of hGH in the urine and the serum of the transgenic mice. Urine samples were collected from transgenic mice by gently massaging the lower abdomen of the mice. Fresh samples were subjected to RIA without further processing. An RIA assay kit from Nichols Institute Diagnostics (San Juan Capistrano, Calif.) was used and $^{125}$I-labeled hGH was obtained from Dupont NEN, (Billerica, Mass.). The standard curve was prepared by plotting the corrected CPM of each standard level against the standard concentration of hGH. The value of the urinary hGH concentration was obtained by referencing the CPM reading of the urine samples. For serum hGH measurement, whole blood was obtained from mouse tails and serum was isolated and subjected to RIA as described above.

Figure 18:
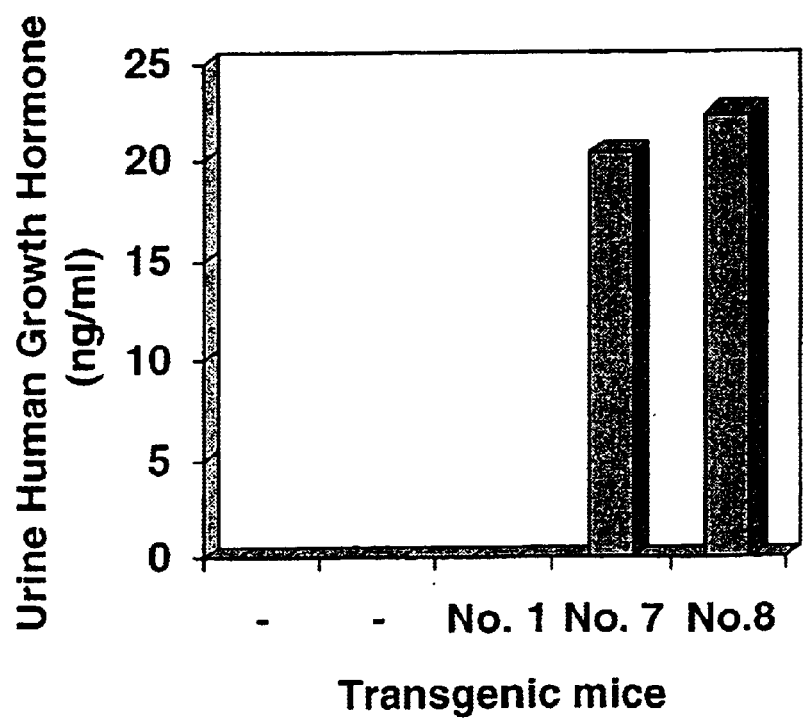
FIG. 18 shows the results of a radioimmunoassay in the detection of hGH in the urine of transgenic mice.

FIG. 18 shows the results from urine samples of two transgene-negative (−) and three transgene-positive mice (NOs. 1, 7, and 8) subjected to RIA. Human growth hormone was detected in transgenic mice Nos. 7 and 8, but not in transgenic mouse No. 1 or in the transgene-negative mice. The concentration of hGH in the two positive Nos. 7 and 8 mice were 20 and 22 ng/ml, respectively.

Figure 19:
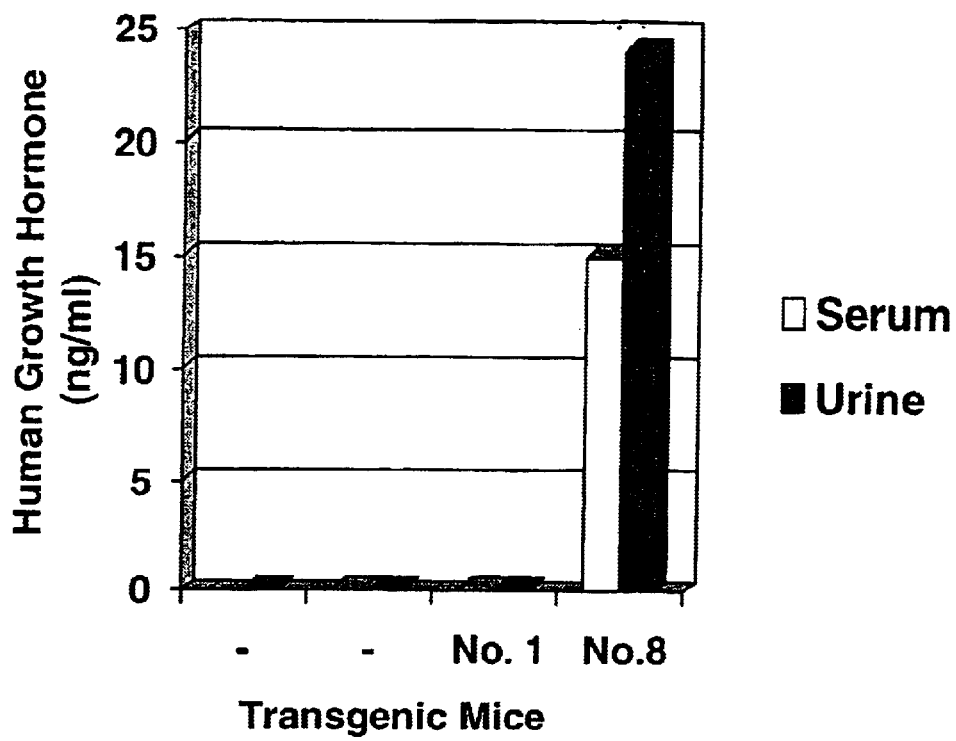
FIG. 19 shows a comparison of the urine and serum concentrations of hGH in transgenic mice.

The urine and serum concentration of hGH in transgenic mice were also compared by RIA. FIG. 19 shows the results of RIA performed on serum and urine samples from transgenic mice. The high concentration of hGH in transgenic mouse No. 8 (15 ng/ml) indicates leakage into the blood of hGH synthesized by kidney epithelial cells.

Figure 20:
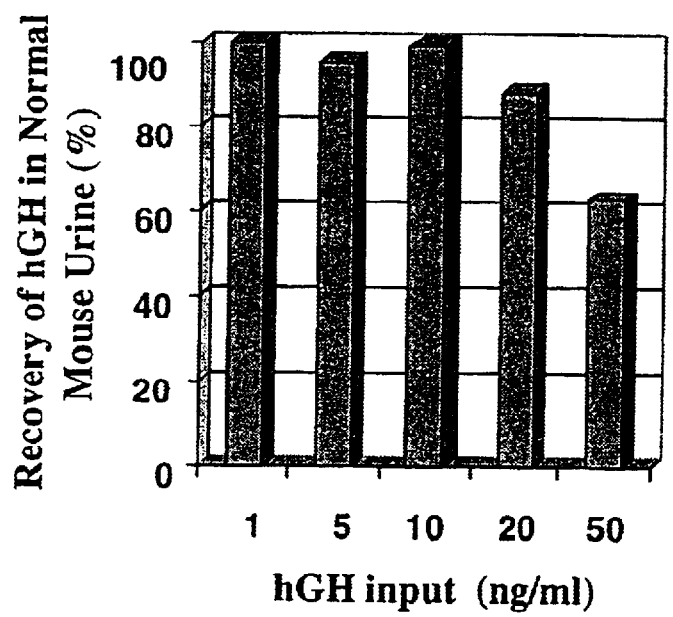
FIG. 20 shows a radioimmunoassay recovery test of hGH in test mice.

In order to assess the sensitivity of the RIA assay for hGH, known amounts of hGH were added into the same volume of urine sample from non-transgenic (normal) mice and then subjected to RIA. From FIG. 20, the recovery of hGH by this assay is observed to be nearly 100% for hGH amounting to 10 ng/ml with the recovery being observed to decrease to 90% and 60%, respectively, when the hGH concentration increases to 20 to 50 ng/ml.

Having now fully described this invention, it will be appreciated that by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional method steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Bachmann et al, Tamm-Horsfall protein-mRNA synthesis is localized to the thick ascending limb of Henle's loop in rat kidney, *Histochemistry* 94:517–523 (1990)

Belecky-Adams et al, Intragenic sequences are required for cell type-specific and injury-induced expression of the rat peripherin gene, *J. Neurosicence* 13:5056–5065 (1993)

Boothroyd et al, A variant surface glycoprotein of *Trypanosoma brucei* synthesized with a C-terminal hydrophobic 'tail' absent from purified glycoprotein, *Nature*, 288 (5791):624–6 (1980)

Brinster et al, Somatic expression of herpes thymidine kinase in mice following injection of a fusion gene into eggs, *Cell* 27:223–231 (1981)

Cameron et al, Transgenic science, *Br. Vet. J.* 150(1):9–24 (1994)

Cameron, Recent advances in transgenic technology, *Mol. Biotechnol.* 7(3):253–265 (1997)

Chaka et al, *Nature* 314:377 (1985)

Chaka et al, *Nature* 319:685 (1986)

Charnay et al, Differences in human alpha- and beta-globin gene expression in mouse erythroleukemia cells: the role of intragenic sequences, *Cell* 38:251–263 (1984)

Clayton et al., The procyclic acidic repetitive proteins of *Trypanosoma brucei*. Purification and post-translational modification, *J. Biol. Chem.* 264(25):15088–93 (1989)

Costantini et al, Introduction of a rabbit beta-globin gene into the mouse germ line, *Nature* 294:92–94 (1981)

Deschambeault et al., Polarized human immunodeficiency virus budding in lymphocytes involves a tyrosine-based signal and favors cell-to-cell viral transmission, *J. Virol.* 73(6):5010–5017 (1999)

Diatchenko et al, Suppression subtractive hybridization: a method for generating differentially regulated or tissue-specific cDNA probes and libraries, *Proc. Natl. Acad. Sci. USA* 93:6025–6030 (1996)

Drohan, W. N., The past, present and future of transgenic bioreactors, *Thromb. Haemost.* 78:542–547 (1997)

Englund, P. T., The structure and biosynthesis of glycosyl phosphatidylinositol protein anchors, *Annu. Rev. Biochem.* 62:121–138 (1993)

Fukuoka et al, GP-2/THP gene family encodes self-binding glycosylphosphatidylinositol-anchored proteins in apical secretory compartments of pancreas and kidney, *Proc. Natl. Acad. Sci. USA* 89:1189–1193 (1992)

Gillies et al, A tissue-specific transcription enhancer element is located in the major intron of a rearranged immunoglobulin heavy chain gene, *Cell* 33:717–728 (1983)

Gordon et al, Secretion of macrophage neutral proteinase is enhanced by colchicine. *Proc. Natl. Acad. Sci. USA* 73:1260 (1976)

Hammer et al, , *Nature* 315:680 (1985)

Hammer et al, *J. Animal Sci.* 63:269 (1986)

Hammer et al, *Science* 235:53 (1987)

Harbers et al, *Nature* 315:680 (1981)

Hennighausen, L., The prospects for domesticating milk protein genes, *J. Cell Biochem.* 49:325–332 (1992)

Hession et al, Uromodulin (Tamm-Horsfall glycoprotein): a renal ligand for lymphokines, *Science* 237:1479–1484 (1987)

Hogan et al, *Manipulating the Mouse Embryo: A Laboratory Manual*, Cold Spring Harbor Laboratory (1986)

Houdebine, Generating biological models through gene transfer to domestic animals, *Vet. Res.* 28(3):201–205 (1997)

Hunt et al, Affinity-purified antibodies of defined specificity for use in a solid-phase microplate radioimmunoassay of human Tamm-Horsfall glycoprotein in urine, *Biochem. J.* 227(3):957–963 (1985)

Hunziker et al., A di-leucine motif mediates endocytosis and basolateral sorting of macrophage IgG Fc receptors in MDCK cells, *EMBO J.* 13(13)2963–2967 (1994)

Hyttinen et al, , *Int. J. Biochem.* 26:859–870 (1994)

James-Pederson et al, Flanking and intragenic sequences regulating the expression of the rabbit alpha-globin gene, *J. Biol. Chem.* 270:3965–3973 (1995)

Jaenisch, R., Transgenic animals, *Science* 240:1468–1474 (1988)

Kahari et al, Deletion analyses of 5'-flanking region of the human elastin gene. Delineation of functional promoter and regulatory cis-elements, *J. Biol. Chem.* 265:9485–9490 (1990)

Karin et al, Characterization of DNA sequences through which cadmium and glucocorticoid hormones induce human metallothionein-IIA gene, *Nature* 308:513–519 (1984)

Kerr et al, The bladder as a bioreactor: urothelium production and secretion of growth hormone into urine, *Nature Biotechnol.* 16:75–79 (1998)

Kollias et al, Regulated expression of human A gamma-, beta-, and hybrid gamma beta-globin genes in transgenic mice: manipulation of the developmental expression patterns, *Cell* 46:89–94 (1986).

Kumar et al, Tamm-Horsfall protein—uromodulin (1950–1990), *Kidney Int.* 37(6):1395–1401 (1990)

Lin et al, A tissue-specific promoter that can drive a foreign gene to express in the suprabasal urothelial cells of transgenic mice, *Proc. Nat. Acad. Sci. USA* 92:679–683 (1995)

Lubon et al, Vitamin K-dependent protein production in transgenic animals, *Thromb. Haemost.* 78(1):532–536 (1997)

McKnight et al, Transcriptional control signals of a eukaryotic protein-coding gene, *Science* 217:316–324 (1982)

Micanovic et al., Aspartic acid-484 of nascent placental alkaline phosphatase condenses with a phosphatidylinositol glycan to become the carboxyl terminus of the mature enzyme, *Proc Natl Acad Sci U.S.A.* 85(5):1398–402 (1988)

Moran et al., Glycophospholipid membrane anchor attachment. Molecular analysis of the cleavage/attachment site, *J. Biol. Chem.* 266(2):1250–7 (1991)

Morcol et al, The porcine mammary gland as a bioreactor for complex proteins, *Ann. NY Acad. Sci.* 721:218–233 (1994)

Niemann, *Transgenic Res.* 7(1):73–75 (1997)

Palmiter et al, Metallothionein-human GH fusion genes stimulate growth of mice, *Science* 222:809 (1983)

Payvar et al, Sequence-specific binding of glucocorticoid receptor to MTV DNA at sites within and upstream of the transcribed region, *Cell* 35:381–392 (1983)

Pennica et al, Identification of human uromodulin as the Tamm-Horsfall urinary glycoprotein, *Science* 236(4797):83–88 (1987)

Prasadan et al, Nucleotide sequence and peptide motifs of mouse uromodulin (Tamm-Horsfall protein)—the most abundant protein in mammalian urine, *Biochim. Biophys. Acta* 1260:328–332 (1995)

Reecy et al, Multiple regions of the porcine alpha-skeletal actin gene modulate muscle-specific expression in cell culture and directly injected skeletal muscle, *Anim. Biotechnol.* 9:101–120 (1998)

Reinhart et al, A new ELISA method for the rapid quantification of Tamm-Horsfall protein in urine, *Am. J. Clin. Pathol.* 92(2):199–205 (1989)

Renkawitz et al, Sequences in the promoter region of the chicken lysozyme gene required for steroid regulation and receptor binding, *Cell* 37:503–510 (1984)

Rindler et al, Uromodulin (Tamm-Horsfall glycoprotein/uromucoid) is a phosphatidylinositol-linked membrane protein, *J. Biol. Chem.* 265:20784–20789 (1990)

Sadeghi et al., O-glycosylation of the $V_2$ vasopressin receptor, *Glycobiology* 9(7):731–737 (1999)

Sanger et al, DNA sequencing with chain-terminating inhibitors, *Proc. Nat. Acad. Sci. USA* 74:5463–5467 (1977)

Seki et al, Structural organization of the rat thy-1 gene *Nature* 313(6002):485–7 (1985).

Shani, M., Tissue-specific and developmentally regulated expression of a chimeric actin-globin gene in transgenic mice, *Mol. Cell. Biol.* 6:26242631 (1986)

Sikorav et al., Complex alternative splicing of acetylcholinesterase transcripts in Torpedo electric organ; primary structure of the precursor of the glycolipid-anchored dimeric form. *EMBO J.* 7(10):2983–93 (1988)

Sikri et al, Localization of Tamm-Horsfall glycoprotein in the human kidney using immuno-fluorescence and mmuno-electron microscopical techniques, *J. Anat.* 132:597–605 (1981)

Simon et al, *Bio/Technology* 6:179–183 (1988)

Stahl et al., Differential release of cellular and scrapie prion proteins from cellular membranes by phosphatidylinositol-specific phospholipase C *Biochemistry,* 29(22):5405–12 (1990).

Stephens et al., Specificity of interaction between adaptor-complex medium chains and the tyrosine-based sorting motifs of TGN 38 and lgp120, *Biochem J.* 335:567–572 (1998)

Sternberg et al, Identification of upstream and intragenic regulatory elements that confer cell-type-restricted and differentiation-specific expression on the muscle creatine kinase gene, *Mol. Cell Biol.* 8:2896–2909 (1988)

Stewart et al, *Science* 217:1046–1048 (1982)

Townes et al, Erythroid-specific expression of human beta-globin genes in transgenic mice, *EMBO J.* 4:1715–1723 (1985)

Udenfriend et al., How glycosyl-phosphatidylinositol-anchored membrane proteins are made, *Annu. Rev. Biochem.* 64:563–591 (1995)

Van Cott et al, Phenotypic and genotypic stability of multiple lines of transgenic pigs expressing recombinant human protein C, *Transgenic Res.* 6(3):203–212 (1997)

Velander et al, Transgenic livestock as drug factories, *Sci. Amer.* 276(1):70–74 (1997)

Wagner et al, The human beta-globin gene and a functional viral thymidine kinase gene in developing mice, *Proc. Natl. Acad. Sci. USA* 78:5016–5020 (1981)

Wagner et al, , *Theriogenology* 21:29 (1984)

Wall et al, Transgenic dairy cattle: genetic engineering on a large scale, *J. Dairy Sci.* 80:2213–2224 (1997a)

Wall et al, Transgenic animal technology, *J. Androl.* 18(3):236–239 (1997b)

Wilkins et al, Isolation of recombinant proteins from milk, *J. Cell Biochem.* 49:333–338 (1992)

Williams, L. S., Canada's huge pregnant-mare-urine industry faces growing pressure from animal-rights lobby, *Can. Med. Assoc. J.* 151:1009–1012 (1994)

Wu et al, Molecular cloning of a 47 kDa tissue-specific and differentiation-dependent urothelial cell surface glycoprotein, *J. Cell. Sci.* 106:31–43 (1993)

Yoshida et al., Discovery of the shortest sequence motif for high level mucin-type O-glycosylation, *J. Biol. Chem.* 272(27):16884–16888 (1997)

Yu et al, Uroplakins Ia and Ib, two major differentiation products of bladder epithelium, belong to a family of four transmembrane domain (4TM) proteins, *J. Cell Biol.,* 125:171–182 (1994)

What is claimed is:

1. A method for producing a recombinant biologically active polypeptide, comprising:
   introducing an isolated DNA molecule comprising a mammalian uromodulin promoter operably linked to a heterologous DNA sequence encoding a heterologous polypeptide, wherein said mammalian uromodulin promoter directs expression of said heterologous polypeptide in vivo to the ascending limb of Henle's loop and the early distal tubules of the kidneys to produce a recombinant biologically active polypeptide in the urine, into a fertilized embryo of a non-human mammal selected from the group consisting of goat, cattle, sheep, pig, and mouse to generate a transgenic non-human mammal which expresses and secretes the heterologous polypeptide into the urine of the transgenic non-human mammal as a recombinant biologically active polypeptide;
   collecting urine from the transgenic non-human mammal; and
   recovering the secreted polypeptide to produce a recombinant biologically active polypeptide.

2. The method of claim 1 wherein said heterologous polypeptide contains a non-native apical surface membrane targeting sequence.

3. The method of claim 1, wherein said non-native apical surface membrane targeting sequence is a C-terminal glycosyl phosphatidylinositol (GPI) signal sequence.

4. The method of claim 1, wherein said apical surface membrane targeting sequence is one or more non-native sites for glycosylation at predicted β-turns of said heterologous polypeptide.

5. The method of claim 4, wherein said one or more non-native sites for glycosylation are sites for Asn-linked glycosylation.

6. The method of claim 4, wherein said one or more non-native sites for glycosylation are sites for O-glycosylation.

7. The method of claim 1, wherein said heterologous polypeptide is a fusion polypeptide.

8. The method of claim 7, wherein said fusion polypeptide is a fusion between a heterologous polypeptide of interest and uromodulin via a chemically or enzymatically cleavable linker, said uromodulin having a GPI signal sequence at its C-terminus.

9. The method of claim 8, wherein said linker is a protease-sensitive linker.

10. The method of claim 1, further comprising a DNA sequence encoding phosphatidylinositol-specific phospholipase C (PIPLC), wherein said DNA sequence is disposed downstream of said heterologous DNA sequence and is operably linked to said mammalian uromodulin promoter, whereby said mammalian uromodulin promoter is capable of driving the expression of said DNA sequence encoding PIPLC.

11. The method of claim 1, wherein any basolateral surface membrane targeting signals native to said heterologous polypeptide is inactivated or deleted.

12. A transgenic non-human mammal all of whose germ cells and somatic cells contain a recombinant construct corresponding to a DNA molecule comprising a mammalian uromodulin promoter operably linked to a heterologous DNA sequence encoding a heterologous polypeptide, wherein:
   said mammalian uromodulin promoter directs expression of said heterologous polypeptide in vivo to the ascending limb of Henle's loop and the early distal tubules of the kidneys to produce a recombinant biologically active polypeptide in the urine
   said DNA molecule has been introduced into said mammal selected from the group consisting of goat, sheep, cattle, pig and mouse, at an embryonic stage; and
   said mammal produces recoverable amounts of a recombinant biologically active polypeptide in its urine.

13. A transgenic non-human mammal according to claim 12, in which all germ cells and somatic cells further contains a recombinant construct comprising a mammalian uromodulin promoter operably linked to a DNA sequence encoding PIPLC, wherein said mammalian uromodulin promoter expresses PIPLC in the kidneys of said transgenic mammal.

14. A method according to claim 1, wherein said introducing step comprises injecting the isolated DNA molecule into a pronucleus of a fertilized embryo.

15. A method according to claim 1, wherein the mammalian uromodulin promoter is a mouse, goat, bovine, human or rat uromodulin promoter.

16. A method according to claim 1, wherein the mammalian uromodulin promoter is a goat uromodulin promoter.

17. A transgenic non-human mammal according to claim 12, which is a transgenic goat.

18. A method according to claim 1, wherein the mammalian uromodulin promoter is a mouse uromodulin promoter.

19. A method according to claim 1, wherein said non-human mammal is a goat.

20. A method according to claim 1, wherein said non-human mammal is cattle.

21. A method transgenic non-human mammal according to claim 12, wherein said non-human mammal is cattle.

22. The transgenic non-human mammal of claim 12, wherein sad heterologous polypeptide contains a non-native apical surface membrane targeting sequence.

23. A method for producing a recombinant biologically active polypeptide, comprising:
   introducing an isolated DNA molecule comprising a mammalian uromodulin promoter, selected from the group consisting of mouse, goat, human, rat, and bovine uromodulin promoters and operably linked to a heterologous DNA sequence encoding a heterologous polypeptide, into a fertilized embryo of a non-human mammal selected from the group consisting of goat, cattle, sheep, pig and mouse to generate a transgenic non-human mammal which expresses said heterologous polypeptide in vivo to the ascending limb of Henle's loop and the early distal tubules of the kidneys to produce and secrete the heterologous polypeptide into the urine of the transgenic non-human mammal as a recombinant biologically active polypeptide;

collecting urine from the transgenic non-human mammal; and recovering the secreted polypeptide as a recombinant biologically active polypeptide.

24. A method according to claim 23, wherein said heterologous polypeptide contains a non-native apical surface membrane targeting sequence.

25. A transgenic non-human mammal all of whose germ cells and somatic cells contain a recombinant construct corresponding to a DNA molecule comprising a mammalian uromodulin, selected from the group consisting of mouse, goat, human, rat and bovine uromodulin promoters and operably linked to a heterologous DNA sequence encoding a heterologous polypeptide, said DNA molecule having been introduced into said mammal selected from the group consisting of goat, sheep, cattle, pig and mouse at an embryonic stage, wherein said mammalian uromodulin promoter directs expression of said heterologous polypeptide in vivo to the ascending limb of Henle's loop and the early distal tubules of the kidneys to produce recoverable amounts of a recombinant biologically active polypeptide in its urine.

26. A transgenic non-human mammal according to claim 25, wherein said heterologous polypeptide contains a non-native apical surface membrane targeting sequence.

* * * * *

SEQUENCE LISTING

<160> NUMBER OF SEQ ID NOS: 54

<210> SEQ ID NO 1
<211> LENGTH: 9345
<212> TYPE: DNA
<213> ORGANISM: Mouse Uromodulin
<220> FEATURE:
<221> NAME/KEY: misc_feature
<222> LOCATION: (1832)..(1832)
<223> OTHER INFORMATION: n is unknown.
<221> NAME/KEY: misc_feature
<222> LOCATION: (7777)..(7777)
<223> OTHER INFORMATION: n is unknown.

<400> SEQUENCE: 1

```
ggggggggccc tcgggagttt ggctaagtct tgcaaatgag ctgtgatgac aggtttgcgc      60
catatgagat ccagtgacaa gctcatctct agatgtctgc ataccaataa gtgacccatc     120
attatgcaat caggccggac tcatcctctg tggctttgtc tcttactact gtaaacttga     180
taacctatat gattttaccc atttcccctc catggcactc aactctcctc ttcctatgtg     240
accctactta tgtcctatgt gactccagct gcttcctttg atgagagcca tcctgttctt     300
tctatgtgac tctgctcact tcttccacgt gactccacca atctgtctac attgcagagt     360
cactcacagt ttcttgagag cagaagactc agaactgatc tgtcctcaat gtcctcccta     420
cactttctcc tcataatcca catatctaaa gctatagaga taatttcatg cactatagct     480
ttcagtacta tcgtatctac tgtctctacc ctgtaactgg tatcttcatg acatctcgaa     540
tatttccaat ttctctattg ctgcaaagtc ttgagaagtc tagtcttatg gatctccttt     600
tctcctcagg tctcctggtc tccacacacc attcacactt cttgaatatt ctttgaacat     660
aacaaattct ctccatgggt ttgttccctc tacccaaatt catgccttca ggatacttac     720
tctgccccat cttcactcat ctctgctttg gtcattcaaa tctcaaatgt agccatttct     780
aaaaggctct ccaagagaat aatatttgaa agcattttgc tattctatca agtgatcata     840
caatgtctgc tcctgccacc accatgacca tccccatgaa tacagacact gccttcttag     900
tgtttgctgt atgtgttctg tgtggtacat tgtagataaa tgctgtaata acatctgtg     960 gagcaaattg aatcatcaga tagcaccctc tctctgagag gcatgatctc atggttatcc    1020
ccaaagcatg aggtaaggac attatcccag gtccatgctg gtttccgtat tgattgtttc    1080
taacacaaac ttaatagatt aaaacagcac ggatttattc tcacatgttt tgagacgcca    1140
gaaatctgac accagtttca atgtttagac ttgatgcaca cctgtaattc tggtacttag    1200
gaggcagatg caggggggact atgatttaaa gcccattttt aagctgctgg gtgagaacct    1260
gtcttgattt ttttttcaca ttgggctaaa agtcaaggat catcagggtt ggtgcattct    1320
ggaagaaacc tttgccttgc agcttcccag agggccgcca gcattccttg gcttgtgttt    1380
ggtcctggaa tcactgtgac cttatgctcc atcctcacat tccctctgca tttatcctct    1440
aagcaccggt gtgcttgtat ccaacctta ggagccccat agatccccca tttctcctcg    1500
acttaatcac acctgtataa gtacttttca ctctgcaaag caatatttgt gggtccaagg    1560
gattaggatg tgggtatatt tgtgggggtgt cattattcaa tgcttcatat ttacactgtt    1620
tctctgtttc actttattgg ggtacttgaa cttctaagaa gaactgaggg gtattgttgt    1680
aggaactaaa ttcccccatg gacctctgtg ctttccacct atcacacaag acagagggta    1740
tttgtatttt tagatcccca gaagaaattc ccactctcaa ccctccatcc ctgacttgct    1800
```

```
cacatctaga tgaagcaggg aacagcctga gncctggaac tcactggagc cagatgactc    1860
tatggagtta ggttttagta ttcaagacac gatgcaagac tcacctgcct tccctcaca    1920
gacatgtggc tgcctgtcaa aggtggggcc atggggctgc tgagactaag tcacgtggac    1980
agcgcccatg acaagcagtg acatggagac caaggctgca gtgtgcatgc tccacaggtg    2040
cacctgaagc ctcagagacg ggaagaggag agggagcaga agatggggt acagataccc    2100
ctctgttagg aagggcttca aaccgtctt ctaagttttt gatccttta aatgtatcca    2160
cctgtcactt gaccctctcc tgctctgtct gatcagcttc tcaaaaccct tcatccccott    2220
aactccaccc tactgaaaaa agatgaaacc acttgtcaat ataaacctca acagctaagc    2280
atggaatact gttaacccct caagacataa agctgactga agggataagt ttgaaaaaaa    2340
tgggcttcag tttgcactag ctaagtatgt aaccttgaag atattactca gtttctctga    2400
acttcagtct gctctcctat ttattgacaa catgtaagag cacataccgg gcatttcttg    2460
tcaccaaatg aagtttccag taccaggaat gggttatatc taatcgagtt gttggccaaa    2520
ggagttccat ggaaactccc aaacaatcca ggctattggc aagacttttg atgtctctcc    2580
acaaactgac agcaactgtt gaaagacaat acctacacag ctcactgaac acagagaagc    2640
tgagttggtg cctacataaa tcctctagct ctatgaaggt ccataatggt attcatggcc    2700
ctagaagata ctcttccctc caccaaagga gaaatgtaaa cactaagcca gccataaacc    2760
ctttggtctg ttagagtggc ctgcctgcaa gttctgctgg tgtaataatg gcacagagct    2820
tgtaggagta accaaacaat atctgatagg ttaaggccca ctccatgaga tcaaacccag    2880
acctaacaac acttgggtgg atgagaaccc gagaccagat aggccaggga cctatgggaa    2940
aactaaacat gactgttctg ctaaaagaac ctaccaataa aatagctcct agtgacattc    3000
tgccatattt atagatcagt tccttgttca tccatcatca gaaaacttcc tcttcagtag    3060
atagaaacaa atatagagcc cacagccaga taatatccag agagtgagat accctggaac    3120
actcagctct aaaagggatg tctccatcaa ccccccccc ccccacctttt caggactcat    3180
gaaaccctcc agaagacgag tcagaaagag tgtaagatcc agaagggatg gaggacatcc    3240
aaaacttaag gccttcaaga cacaactgta agggaacaca tatgaactta gagagatggt    3300
gcagcatgca cagagcctgc atgggcttgt accagatggg gttctagagc tgaaaggaga    3360
aatggatagc cactctgatt cctaacccag aagtgacccc taactgatag tgacttgcaa    3420
ataaaaaatt agtctttttt caagggagt ctcactggga aaataaacca ctctaaatag    3480
tagaccccat gcccagcagt agatggccaa cagaaaatga actcaatgtc atctttgacc    3540
ttcctttgtc ggaaagcttt ttgtttgctt tttcttaccc tacaggtcct ttgcatattt    3600
attatggttt cttgtttcag ttttttaatg gaactcctga gtgtgtgaat gtgtgtgtct    3660
ctgcatacat gtgtgtttct taagcccgtt cttttctttt tcttctcttt attgtttaaa    3720
aaaacaattg ttcttatttt tattattatt ccttattta gacagaaaca ttgtggatcc    3780
agatgggaga agaggttgga ggaattggga ggagtaaagg gacagaaacc ataatcaggg    3840
ggaaccataa tcaggagaa ccataatcag ggggagccat aatcaggggg agccataatc    3900
caagggaacc ataatcagaa tatactgtat gaaaaaaatt ctattttcaa taaaaaaaga    3960
ataaaaaaaa aacagtctga ctgaagaata gcacttggta agtaactctt gttataacaa    4020
tccatatcaa atgccctgcc tgtgttagca agttaagaga aaagattatt ccaagagatc    4080
caagtctcct tcaaaaccaa gtgtgtacag aacattgtct gaggagtaag attgcatttg    4140
gcaacatgca tgtctttaat ggtgtggaga atttcagtgg agttggcacg tcagaaagca    4200
```

```
cactggtgaa aaatggagag aatagatata tcctttgaga aatttggtct caaaaagtag    4260
ggtatcaaat tacttggtgt ctgtgagatc aattggttgt ctctgtaggt tagcttacat    4320
aggagacagg aataagtgaa ggagagaagg gaggacattg gagcacccaa ggagagaggg    4380
accttcctcc taaaagtgaa tgaggtggcc ttcattccaa ggagaagaga ttcaggtcgc    4440
ccgggaagat gagggaccaa catccacaag gaatggcagg aagtcatcct gtgtgcataa    4500
atggagagag ggggtcaaag atggagcaaa aaggatgag caagaaaatg gtggatgtgg     4560
atactctgag gatggcctgg ctgtggtgag caaaatgtgg gcaaagtggc actccatgaa    4620
caagacagct tgctctgttt gcagatcctt aaataaaggc acatggcatg ccatggaggc    4680
taggggagtg gaggggaaag gtatatagat agatgcagaa gtaccagagg agccaggaag    4740
gacaggagta ggagggacag gtttgcacaa ggctttgtcc tctccccacc agctctctct    4800
cccttctgta tatgcacata cacagtgagc tagtgtgcat atgtgtgcac atatgcatgt    4860
gatgaacaga ggccagtctt gggtgtcagt cttcaggccc tatctacctt gttttttgaga    4920 caatctcact tgagtgagtt gagtgactct cctagtattc tacagaggtt tcctcaggtg    4980
gggaggaatg ggtgggagaa gcaaatttaa gactggttga tttcttgaat ttcagtgggc    5040
ttgggaaata gcagctatat attcagtttc ctcgttcctg gctggcttcc tggggtgatc    5100
agagcagagt atagtagccc tgtgtggcag tcacaccaag cagacagaag ataggcatg     5160 gctctggtgt ggctggtaga cataggaaag gatccttgta gcaagatgtt tgccatctcc    5220
agagacttag acagcccagg aaagtttgtc ctcccaggac cagccagcac tgagactgga    5280
atgcatcaaa tccagagacc agaaagcacg gtgctagcac ttaggaagag acactagccc    5340
aaagtctcct tgctcctgcc taaagctttg ccaattctgc aaaccttgaa aaattagcat    5400
ctttaaattc agaagggata caagaagaga acttacatgg gaccttgtaa aaaagcatag    5460
ggcatcagta actaaagtta caaagataac aatcagtggt gagtgaacaa aggacatggc    5520 catgttttt ttgttatgaa acacacgcac aggcacaggc actcacgtgt gcgcacgcgc     5580
gcacacacac acacgcgcac acacacacac acgcatgcac acatgcacca cacacaaact    5640 gcaaagtga ataaaaagat atttctcact ttggcaaagt ggatggaaag ttgatcaaaa     5700
tgaaagttat actcagaact attttgtact agagggaggt tataaattat tgttattgtt    5760
atattctatt ttactgtttg tggcagccta agttggtctt gaactcacta tgaagctagc    5820
aatgaccttg agcttctgat ccttatatct acactctcaa gtgcccagat tataagtgtg    5880
caccactata ctcagtttat gctgtgctaa ggactaagcc caattataca aacacacaca    5940
catatataca cacatacaca cacacacaca cgtatatata tgtatatata tatacataca    6000
tacacacaca cacacacata tatgtaaaat ttgggaagat atatcaatct tctttaaagt    6060
acatgctact ttggtccaaa actttcactt ttaggaagtt aagaaggaag agacagaata    6120
agagatgtcc caagaaagtc agtgtggttg tcttagttat gcttcctgct cagtcaatgt    6180
ttcagatttt tctcagcaca atgacatcta ttctatcaag ttttttgataa ctctttacat    6240 gggactgggt gtggcttgtg gctctagcta tttctatttg tgactgccta tcagcaaagc    6300
atccacttca gactttgact caaacatcac caagtattcc cacttgcatt gtctctgtta    6360
accagcatca ctgttcacag gcagggcat cacatctcac aaagggaaag ggaaagggaa     6420
gagttaaatt ccctgggata ctagtcacgg tggactcagg caaacagcct cttcaattgt    6480
aagatgattc cctagtccaa ggaccctcta ctgtttggac tccagtcttg tctgacagag    6540
```

```
gtccagttca ggagtgtcca gatggtctga taacctgatg ccattctcag agactctttc    6600
ctgtctggaa tctagtgagg aggacttatc tggtgaagct gtcctttaga acaggagtgt    6660
gttccagtct tcaaagcaaa cattccttt atcctaacac agtctgactt cagatatact    6720
gtcttttcc tggctccttg gcttaggtc taccttgtcc ttgcccaggt ccaagaaaag    6780
gcccagaacc ttggcactgt tttgccagtt aatgtctaac tgaggaatgt cttgctgcca    6840
aaaggtgaaa acagagacct tgtatttcca ggcacaggtg tgaccccaat gtcaatcatt    6900
ttgtgtctaa ctcccagggg aaaaactaac aacaacagac tcatggcttg aaaaggtga    6960
attctatgcc aaaagggaag gaaagttcta cccccacaga acaatctca gagggcagaa    7020
gcagagaata atctgaggga gagggccagc caagggcagg caagtatata ttgatcacag    7080
gcacttactt gtgaatggac cagtcctgtc ctgggttcag gtaaggctgt atgaaactgt    7140
cacccccata tccacttctc ctctatctaa tcccattata tttcagggag gttgtggtag    7200
aagcttagct tctggacact gggtcccat gctaaccttc atggcatcct ggtatgctgc    7260
tgtaaaacct agggtaatgc ttgcatccat ctggaattat ttcacctgtt gcaaccacaa    7320
tcatttgaa aatactagta tgtattatag ttatgtatgt atatagagtt aatcatctct    7380
aaagctcctt atcttttgcc atttctttac atgagttgta tgaagatgta gacgatattc    7440
attattctct ttggtatcta gcaccttgtt tggcacataa tactactcaa taagggtttg    7500
ttgaatgaat aagtaggtga gagcaaattg taagttcagg taatcacgaa cttcctgtaa    7560
aactccaagg ctgcctccag taaggtataa gtcctgagtg agcctttccc catcttgcaa    7620
cttttgctc caaatgaaag actcagttct tcaaaatgtg cagcacatgg aggtttgcga    7680
catagggtg tattcacaga ggcttcggaa gcccaccaaa cctacagtta gatcactgta    7740
cagtcttcct tttacataca agctgtgcct cctggtntac atccatgctg ttttctgatc    7800
catatagagg gtacacaaca aaagcatttc ttctgtctat agggaagcaa attagatcat    7860
gcatgtgcct cacccaccte tgttctcatg atttcaggca tcagaaacac aagggaaatc    7920
caaagtacct aacccatcct tgcctttggg caggtgtttc caggacagag ggcagagtgt    7980
aaaggatggg gatccctttg acctggatgc tgctggtaat gatggtaacc tcctggttca    8040
ctctggctga agccagtaac tcaacagaag cgagtaagtg tgtgtgtgtg tgtgtgtgtg    8100
tgtgtgtgtg tgtgtagaga aatgttccct ttgcagaagc aatcttaatc cctcttttag    8160
cacacttgat gtgatcttta ttttaagccc atttctcaga ttgtaatgag cacaggactc    8220
acttcgaagt tttgttaaga tgcaaattct actttagtag gtctagcaag gggcccgaga    8280
ctctgaatta atagcagcgt gtgggtgatg tttctggtgg acaagggggc taaaacacct    8340
ctgaaccatt tctgcacttc acggtaaagt cacaagcatg cccagataca aagagattt    8400
gacccacctc tcctgtaagt gtgaagtcat cccatggggg tagctttgcc ttccaccctg    8460
gagtactctg gaattacact aagtataatt gtgaggtcat ggttaaaagc acatgttctg    8520
tggtcaggcc atgtgcgtgt accctgtttg acaactggct tgctcgttct gaatgtcaat    8580
attctttct gtaaatgaag aaaatgaaaa tgggttccag cggcaggggg tgtgccctgg    8640
ggaggattcg ctaaactcta gactgaaaag tcaatgaata gaggactcca ctcaggggag    8700
ctcggatggg tgtgttttga aggtgccaac aacttaacaa gtccagaaaa gcaagaaagt    8760
atgggcaggg gcacctgcca gctgcaggga ttctgaagct gggctcttct gtccgcagga    8820
cggtgttctg aatgccacaa ccacgccacc tgcacggtgg atggtgtggt cacaacgtgc    8880
tcctgccaga ccggcttcac tggtgatggg ctggtgtgtg aggacatgga tgagtgtgct    8940
```

-continued

```
acccatgga ctcacaactg ctccaacagc agctgtgtga acaccccggg ctcgtttaag      9000
tgctcctgtc aggatggttt tcgtctgacg cctgagctga gctgcactga tgtggatgag      9060
tgctcagagc aggggctcag taactgtcat gccctggcca cctgtgtcaa cacagaaggc      9120
gactacttgt gcgtgtgtcc cgagggcttt acagggatg gttggtactg tgagtgctcc       9180
ccaggctcct gtgagccagg actgactgc ttgccccagg gcccgatgg aaagctggtg        9240 tgtcaagacc cctgcaatac atatgagacc ctgactgagt actggcgcag cacagagtat      9300
ggtgtgggct actcctgtga cgcgggtctg cacggctggt accgg                      9345
```

<210> SEQ ID NO 2
<211> LENGTH: 297
<212> TYPE: DNA
<213> ORGANISM: Goat Uromodulin

<400> SEQUENCE: 2

```
tactggcgca gcacagagta cggctccggc tacgtctgtg atgtcagtct gggcggctgg       60
taccgcttcg tgggccaggg cggcgtgcgc ctgcccgaga cctgcgtgcc cgtcctgcac      120
tgcaacacgg ccgcgcctat gtggctcaac ggcacgcacc catcgagcga cgagggcatc      180
gtgaaccgcg tggcctgtgc gcactggagc ggcgactgct gcctgtggga cgcgcctgtc      240
caagtgaagg cctgtgccgg cggctactac gtgtacaacc tgacagagcc ccctgag        297
```

<210> SEQ ID NO 3
<211> LENGTH: 653
<212> TYPE: DNA
<213> ORGANISM: Goat Uromodulin
<220> FEATURE:
<221> NAME/KEY: misc_feature
<222> LOCATION: (605)..(605)
<223> OTHER INFORMATION: n is unknown.
<221> NAME/KEY: misc_feature
<222> LOCATION: (609)..(609)
<223> OTHER INFORMATION: n is unknown.
<221> NAME/KEY: misc_feature
<222> LOCATION: (612)..(612)
<223> OTHER INFORMATION: n is unknown.

<400> SEQUENCE: 3

```
actatagggc acgcgtggtc gacggcccgg gctggtaaat cttaaaaaaa aaaaaaaaca       60 aaagaacat cactaagccc ccctgccctg gcactttatt ggaaggtcaa gaacacactc       120
aaccacacaa gagatgtgaa catacctgtg tggtacccaa agacatcccc tttcacacat      180
acatgaccct tccattgggt tgcacattgc tgttagcttt tgttggaga agggagctag        240 acacctctac acaaccccca actgagttc tctggaacag agtaaatacc atcgtgtcat       300
catggagcgc acacacactg tggtcctgca acctcgattt gtgtcctggc tctgctgctt      360
accaatgaag caagtagctt aaaccttctg aatctcaagt ttcctcaccc tcaaactata     420
gctaaataca aaagtcattt cccagggcca ctggagagga ttctatcaga taatggatag     480
aagatgccta tcccagtgtt tgacatatcc taagtgctta atacacgaga gctcaccatc     540
tttactggta ttattgcaca gagaaacaca caaagtgtca gtgcccctgc taggtagaga    600
gggangcang gnaaggagat ctgagcaaaa ggcatagaat atatcaagct ggg             653
```

<210> SEQ ID NO 4
<211> LENGTH: 655
<212> TYPE: DNA
<213> ORGANISM: Goat Uromodulin
<220> FEATURE:

<221> NAME/KEY: misc_feature
<222> LOCATION: (42)..(42)
<223> OTHER INFORMATION: n is unknown.
<221> NAME/KEY: misc_feature
<222> LOCATION: (58)..(58)
<223> OTHER INFORMATION: n is unknown.
<221> NAME/KEY: misc_feature
<222> LOCATION: (85)..(85)
<223> OTHER INFORMATION: n is unknown.

<400> SEQUENCE: 4

```
cggggaagg tttattttgt ttcttttcaa aggggtctt gntctgtctc aaagaccnta      60
aggaccatga aaaatctct ttgtnaaaag tgccaagcgg tccccactct gaatctgggc    120
ttttctgcct gcagaaagct gctctgaatg tcacgccaat gccacttgta cggtggacgg   180
ggcttgccac gacctgcgcc tgccaggagg gcttcactgc gacggcctcg aatgtgcgga   240
tctggatgaa tgcgccattc tgggggcgca caactgctcc gccaccaaca gctgcgtgaa   300
cgcgctgggc tcctacacat gcgtctgccc tgaaggtttc ctcctgagct cggagctcgg   360
ctgcgaggat gtggacgagt gtcagagcc agggctcagc cgctgccacg ccctggccac   420
ctgcatcaat ggcgagggca actactcatg cgtgtgtccc gcgggctacg tgggggacgg   480
gaggcactgt gagtgttccc cgggctcctg cgggcctggg ctagactgcg tgcgggaggg   540
tgacgcgcta gtgtgcgctg acccgtgcca ggcgcaccac atcctggacg aatactggcg   600
cagcacagag tacggctccg gctacgtctg tgatgtcagt ctgggcggct ggtac         655
```

<210> SEQ ID NO 5
<211> LENGTH: 24
<212> TYPE: DNA
<213> ORGANISM: Mouse Uromodulin

<400> SEQUENCE: 5

```
tggaccagtc ctgtcctggt tcag                                            24
```

<210> SEQ ID NO 6
<211> LENGTH: 24
<212> TYPE: DNA
<213> ORGANISM: Mouse Uromodulin

<400> SEQUENCE: 6

```
gggtgttcac acagctgctg ttgg                                            24
```

<210> SEQ ID NO 7
<211> LENGTH: 22
<212> TYPE: DNA
<213> ORGANISM: Mouse Uromodulin

<400> SEQUENCE: 7

```
agggctttac aggggatggt tg                                              22
```

<210> SEQ ID NO 8
<211> LENGTH: 22
<212> TYPE: DNA
<213> ORGANISM: Mouse Uromodulin

<400> SEQUENCE: 8

```
gattgcactc aggggctct gt                                               22
```

<210> SEQ ID NO 9
<211> LENGTH: 24
<212> TYPE: DNA
<213> ORGANISM: Mouse Uromodulin

```
<400> SEQUENCE: 9
ggaacttcat agatcagacc cgtg                                            24

<210> SEQ ID NO 10
<211> LENGTH: 24
<212> TYPE: DNA
<213> ORGANISM: Mouse Uromodulin

<400> SEQUENCE: 10
tgccacattc cttcaggaga cagg                                            24

<210> SEQ ID NO 11
<211> LENGTH: 22
<212> TYPE: DNA
<213> ORGANISM: Mouse Uromodulin

<400> SEQUENCE: 11
agggctttac aggggatggt tg                                              22

<210> SEQ ID NO 12
<211> LENGTH: 22
<212> TYPE: DNA
<213> ORGANISM: Mouse Uromodulin

<400> SEQUENCE: 12
gattgcactc aggggctct gt                                               22

<210> SEQ ID NO 13
<211> LENGTH: 22
<212> TYPE: DNA
<213> ORGANISM: Mouse Uromodulin

<400> SEQUENCE: 13
gcctcagggc ccggatggaa ag                                              22

<210> SEQ ID NO 14
<211> LENGTH: 22
<212> TYPE: DNA
<213> ORGANISM: Mouse Uromodulin

<400> SEQUENCE: 14
gcagcagtgg tcgctccagt gt                                              22

<210> SEQ ID NO 15
<211> LENGTH: 20
<212> TYPE: DNA
<213> ORGANISM: Mouse Uromodulin

<400> SEQUENCE: 15
tgtcctatgt gactccagct                                                 20

<210> SEQ ID NO 16
<211> LENGTH: 20
<212> TYPE: DNA
<213> ORGANISM: Mouse Uromodulin

<400> SEQUENCE: 16
tctcctcagc tctcctggtc                                                 20

<210> SEQ ID NO 17
<211> LENGTH: 20
<212> TYPE: DNA
```

-continued

```
<213> ORGANISM: MouseUromodulin

<400> SEQUENCE: 17
tcctgccacc accatgacca                                              20

<210> SEQ ID NO 18
<211> LENGTH: 20
<212> TYPE: DNA
<213> ORGANISM: Mouse Uromodulin

<400> SEQUENCE: 18
aagcaccggt gtgcttgtat                                              20

<210> SEQ ID NO 19
<211> LENGTH: 20
<212> TYPE: DNA
<213> ORGANISM: Mouse Uromodulin

<400> SEQUENCE: 19
atggggctgc tgagactaag                                              20

<210> SEQ ID NO 20
<211> LENGTH: 20
<212> TYPE: DNA
<213> ORGANISM: Mouse Uromodulin

<400> SEQUENCE: 20
aagtcagact gtgttaggat                                              20

<210> SEQ ID NO 21
<211> LENGTH: 20
<212> TYPE: DNA
<213> ORGANISM: Mouse Uromodulin

<400> SEQUENCE: 21
attgactgag caggaagcat                                              20

<210> SEQ ID NO 22
<211> LENGTH: 20
<212> TYPE: DNA
<213> ORGANISM: Mouse Uromodulin

<400> SEQUENCE: 22
attttataac ctccctctag                                              20

<210> SEQ ID NO 23
<211> LENGTH: 20
<212> TYPE: DNA
<213> ORGANISM: Mouse Uromodulin

<400> SEQUENCE: 23
atgcattcca gtctcagtgc                                              20

<210> SEQ ID NO 24
<211> LENGTH: 21
<212> TYPE: DNA
<213> ORGANISM: Mouse Uromodulin

<400> SEQUENCE: 24
tggggagagg acaaagcctt g                                            21

<210> SEQ ID NO 25
<211> LENGTH: 20
```

<212> TYPE: DNA
<213> ORGANISM: Mouse Uromodulin

<400> SEQUENCE: 25
tgacgtgcca actccactga                    20

<210> SEQ ID NO 26
<211> LENGTH: 20
<212> TYPE: DNA
<213> ORGANISM: Mouse Uromodulin

<400> SEQUENCE: 26
aggacctgta gggtaagaaa                    20

<210> SEQ ID NO 27
<211> LENGTH: 20
<212> TYPE: DNA
<213> ORGANISM: Mouse Uromodulin

<400> SEQUENCE: 27
tctggctgtg ggctctatat                    20

<210> SEQ ID NO 28
<211> LENGTH: 23
<212> TYPE: DNA
<213> ORGANISM: Goat Uromodulin

<400> SEQUENCE: 28
gactgagtac tggcgcagca cag                23

<210> SEQ ID NO 29
<211> LENGTH: 22
<212> TYPE: DNA
<213> ORGANISM: Goat Uromodulin

<400> SEQUENCE: 29
gattgcactc aggggctct gt                  22

<210> SEQ ID NO 30
<211> LENGTH: 28
<212> TYPE: DNA
<213> ORGANISM: Goat Uromodulin

<400> SEQUENCE: 30
gtaccagccg cccagactga catcacag            28

<210> SEQ ID NO 31
<211> LENGTH: 28
<212> TYPE: DNA
<213> ORGANISM: Goat Uromodulin

<400> SEQUENCE: 31
caggttgtac acgtagtagc cgccggca            28

<210> SEQ ID NO 32
<211> LENGTH: 27
<212> TYPE: DNA
<213> ORGANISM: Goat Uromodulin

<400> SEQUENCE: 32
aagatttacc agcccgggcc gtcgacc             27

<210> SEQ ID NO 33

```
<211> LENGTH: 27
<212> TYPE: DNA
<213> ORGANISM: Goat Uromodulin

<400> SEQUENCE: 33
aataaagtgc cagggcaggg gggctta                                           27

<210> SEQ ID NO 34
<211> LENGTH: 27
<212> TYPE: DNA
<213> ORGANISM: Goat Uromodulin

<400> SEQUENCE: 34
cttgtgtggt tgagtgtgtt cttgacc                                           27

<210> SEQ ID NO 35
<211> LENGTH: 27
<212> TYPE: DNA
<213> ORGANISM: Goat Uromodulin

<400> SEQUENCE: 35
tgtgaaaggg gatgtctttg ggtacca                                           27

<210> SEQ ID NO 36
<211> LENGTH: 27
<212> TYPE: DNA
<213> ORGANISM: Goat Uromodulin

<400> SEQUENCE: 36
acagcaatgt gcaacccaat ggaaggg                                           27

<210> SEQ ID NO 37
<211> LENGTH: 1630
<212> TYPE: DNA
<213> ORGANISM: Goat Uromodulin

<400> SEQUENCE: 37
actatagggc acgcgtggtc gacggcccgg gctggtaaag acacccagac ttaggttttg      60
acagagcctc atgttcacca accagaaatg acattcacca cctaggattg agaaaaagaa     120
tattaggaac ttttattttc ttctgaagtt atagcaaaga aagggaaaaa aaaaaaacat     180
tcttatgggg gataaacggg caaggatac aaacagttca gaaaagaata aatagtaagc      240
aaatgaaaag ataacttcct ttttcatcaa agaaccgcaa aagtaaataa tgataagatg     300
tttctcactt ttccacaaag atgaaagtta atgcccaggg tggctgagta ctgtgctggg     360
attgtgaact aactgttata gatctctctg gggtgctgtt tgggaagaaa catcgctgaa     420
aactgagcta cctcttttcc tatgaaattc ccctgaggag gtgagtgagc cgctgctgat     480
cgtcacccga gcactaggcc agacagaagg agaaagccct caagaggca atgctgtgga      540
tcactgtcat atttcctgct cagcctgagt tcacatgtgc ctgattttc tcaatatggc       600
attgccatta acgtggaatt aggtcaggag acctaaggct gaaccaagcc ctgtcattct     660
ctgccccatg actgcgcatc accaaaacag catcggcagt gacttccaca gatggtacca     720
ttgctatatg ccttaacttg catcatctcc tttaatggcc ataacaattc taggacacgg     780
gtattcttgt tttacagatg atgaaaatta ccctctggaag gaaaattact ggcacacaaa    840
aaacgctgac caggattcag atagactgac tccaaagtca gtctgttcat ctacaaaatt     900
atctacttct caaggacctt ccttcatggg aattcaaatt tcttgattca cagagcatct     960
ggtccaatga tgtctgaatt atctgctgtc tctgaccttc agccattctc agctcctttc    1020
```

-continued

```
ctgatcacat tgggacccca ggggagctgg ctgaatctgt gaggatggca tttgctttgg    1080
aattaagtgg ccacaagtac acatcctggt ggggacgatg agcacccctt ttctcctgga    1140
gcagcctggc ttcagattct ggcctctgct tggctccact ttgtgctttt caatgaccaa    1200
gaaaatccca ggcccttgga attgtttact cagttaattt ctaactaaag aacctcttgt    1260
tgccaaaagg tataaaacag agcccttgta gctgtgggca cagctgtgac ccccatgtca    1320
atcatttggg gtctctacct attagggaaa agaacaacaa ccacctcaca gcctagaaaa    1380
ggaaaacact gtgtcaaaag ggaaaaatat tccaccccca ttaaaataat taagaaacag    1440
aaccagagga tcattggagg agagattgcc agtgggggac agatgtatat atatagatat    1500
gaaagtcacc tacttgtaaa aggattaatt ctacctttct ggtttcaggt aaggctatct    1560
gcagctctca cttctcctag ccacttctcc catctagtct ttgctggctc ccattctgtt    1620
tgaaggatgg                                                           1630
```

<210> SEQ ID NO 38
<211> LENGTH: 644
<212> TYPE: PRT
<213> ORGANISM: Rat Uromodulin

<400> SEQUENCE: 38

```
Met Gly Gln Leu Leu Ser Leu Thr Trp Leu Leu Leu Val Met Val Val
1               5                   10                  15

Thr Pro Trp Phe Thr Val Ala Gly Ala Asn Asp Ser Pro Glu Ala Arg
            20                  25                  30

Arg Cys Ser Glu Cys His Asp Asn Ala Thr Cys Val Leu Asp Gly Val
        35                  40                  45

Val Thr Thr Cys Ser Cys Gln Ala Gly Phe Thr Gly Asp Gly Leu Val
    50                  55                  60

Cys Glu Asp Ile Asp Glu Cys Ala Thr Pro Trp Thr His Asn Cys Ser
65                  70                  75                  80

Asn Ser Ile Cys Met Asn Thr Leu Gly Ser Tyr Glu Cys Ser Cys Gln
                85                  90                  95

Asp Gly Phe Arg Leu Thr Pro Gly Leu Gly Cys Ile Asp Val Asn Glu
            100                 105                 110

Cys Thr Glu Gln Gly Leu Ser Asn Cys His Ser Leu Ala Thr Cys Val
        115                 120                 125

Asn Thr Glu Gly Ser Tyr Ser Cys Val Cys Pro Lys Gly Tyr Arg Gly
    130                 135                 140

Asp Gly Trp Tyr Cys Glu Cys Ser Pro Gly Phe Cys Glu Pro Gly Leu
145                 150                 155                 160

Asp Cys Leu Pro Gln Gly Pro Ser Gly Lys Leu Val Cys Gln Asp Pro
                165                 170                 175

Cys Asn Val Tyr Glu Thr Leu Thr Glu Tyr Trp Arg Ser Thr Asp Tyr
            180                 185                 190

Gly Ala Gly Tyr Ser Cys Asp Ser Asp Met His Gly Trp Tyr Arg Phe
        195                 200                 205

Thr Gly Gln Gly Gly Val Arg Met Ala Glu Thr Cys Val Pro Val Leu
    210                 215                 220

Arg Cys Asn Thr Ala Ala Pro Met Trp Leu Asn Gly Ser His Pro Ser
225                 230                 235                 240

Ser Arg Glu Gly Ile Val Ser Arg Thr Ala Cys Ala His Trp Ser Asp
                245                 250                 255
```

```
His Cys Cys Leu Trp Ser Thr Glu Ile Gln Val Lys Ala Cys Pro Gly
            260                 265                 270
Gly Phe Tyr Val Tyr Asn Leu Thr Glu Pro Pro Glu Cys Asn Leu Ala
        275                 280                 285
Tyr Cys Thr Asp Pro Ser Ser Val Glu Gly Thr Cys Glu Glu Cys Gly
    290                 295                 300
Val Asp Glu Asp Cys Val Ser Asp Asn Gly Arg Trp Arg Cys Gln Cys
305                 310                 315                 320
Lys Gln Asp Phe Asn Val Thr Asp Val Ser Leu Leu Glu His Arg Leu
                325                 330                 335
Glu Cys Glu Ala Asn Glu Ile Lys Ile Ser Leu Ser Lys Cys Gln Leu
            340                 345                 350
Gln Ser Leu Gly Phe Met Lys Val Phe Met Tyr Leu Asn Asp Arg Gln
        355                 360                 365
Cys Ser Gly Phe Ser Glu Arg Gly Glu Arg Asp Trp Met Ser Ile Val
    370                 375                 380
Thr Pro Ala Arg Asp Gly Pro Cys Gly Thr Val Leu Arg Arg Asn Glu
385                 390                 395                 400
Thr His Ala Thr Tyr Ser Asn Thr Leu Tyr Leu Ala Ser Glu Ile Ile
                405                 410                 415
Ile Arg Asp Ile Asn Ile Arg Ile Asn Phe Glu Cys Ser Tyr Pro Leu
            420                 425                 430
Asp Met Lys Val Ser Leu Lys Thr Ser Leu Gln Pro Met Val Ser Ala
        435                 440                 445
Leu Asn Ile Ser Leu Gly Gly Thr Gly Lys Phe Thr Val Gln Met Ala
    450                 455                 460
Leu Phe Gln Asn Pro Thr Tyr Thr Gln Pro Tyr Gln Gly Pro Ser Val
465                 470                 475                 480
Met Leu Ser Thr Glu Ala Phe Leu Tyr Val Gly Thr Met Leu Asp Gly
                485                 490                 495
Gly Asp Leu Ser Arg Phe Val Leu Leu Met Thr Asn Cys Tyr Ala Thr
            500                 505                 510
Pro Ser Ser Asn Ser Thr Asp Pro Val Lys Tyr Phe Ile Ile Gln Asp
        515                 520                 525
Arg Cys Pro His Thr Glu Asp Thr Thr Ile Gln Val Thr Glu Asn Gly
    530                 535                 540
Glu Ser Ser Gln Ala Arg Phe Ser Ile Gln Met Phe Arg Phe Ala Gly
545                 550                 555                 560
Asn Ser Asp Leu Val Tyr Leu His Cys Glu Val Tyr Leu Cys Asp Thr
                565                 570                 575
Met Ser Glu Gln Cys Lys Pro Thr Cys Ser Gly Thr Arg Tyr Arg Ser
            580                 585                 590
Gly Asn Phe Ile Asp Gln Thr Arg Val Leu Asn Leu Gly Pro Ile Thr
        595                 600                 605
Arg Gln Gly Val Gln Ala Ser Val Ser Lys Ala Ala Ser Ser Asn Leu
    610                 615                 620
Gly Phe Leu Ser Ile Trp Leu Leu Leu Phe Leu Ser Ala Thr Leu Thr
625                 630                 635                 640
Leu Met Val His

<210> SEQ ID NO 39
<211> LENGTH: 642
<212> TYPE: PRT
<213> ORGANISM: Mouse Uromodulin
```

-continued

<400> SEQUENCE: 39

```
Met Gly Ile Pro Leu Thr Trp Met Leu Leu Val Met Val Thr Ser
1               5                  10                  15

Trp Phe Thr Leu Ala Gly Ala Ser Asn Ser Thr Glu Ala Arg Arg Cys
                20                  25                  30

Ser Glu Cys His Asn Asn Ala Thr Cys Thr Val Asp Gly Val Val Thr
            35                  40                  45

Thr Cys Ser Cys Gln Thr Gly Phe Thr Gly Asp Gly Leu Val Cys Glu
        50                  55                  60

Asp Met Asp Glu Cys Ala Thr Pro Trp Thr His Asn Cys Ser Asn Ser
65                  70                  75                  80

Ser Cys Val Asn Thr Pro Gly Ser Phe Lys Cys Ser Cys Gln Asp Gly
                85                  90                  95

Phe Arg Leu Thr Pro Gly Leu Gly Cys Thr Asp Val Asp Glu Cys Ser
                100                 105                 110

Glu Gln Gly Leu Ser Asn Cys His Ala Leu Ala Thr Cys Val Asn Thr
            115                 120                 125

Glu Gly Asp Tyr Leu Cys Val Cys Pro Lys Gly Phe Thr Gly Asp Gly
        130                 135                 140

Trp Tyr Cys Glu Cys Ser Pro Ser Ser Cys Glu Pro Gly Leu Asp Cys
145                 150                 155                 160

Leu Pro Gln Gly Pro Asp Gly Lys Leu Val Cys Gln Asp Pro Cys Asn
                165                 170                 175

Thr Tyr Glu Thr Leu Thr Glu Tyr Trp Arg Ser Thr Glu Tyr Gly Val
                180                 185                 190

Gly Tyr Ser Cys Asp Ala Gly Gln His Gly Trp Tyr Arg Phe Thr Gly
            195                 200                 205

Gln Gly Gly Val Arg Met Ala Glu Thr Cys Val Pro Val Leu Ala Cys
        210                 215                 220

Asn Thr Ala Ala Pro Met Trp Leu Asn Gly Ser His Pro Ser Ser Ser
225                 230                 235                 240

Glu Gly Ile Val Ser Arg Thr Ala Cys Ala His Trp Ser Asp His Cys
                245                 250                 255

Cys Arg Trp Ser Thr Glu Ile Gln Val Lys Ala Cys Pro Gly Gly Phe
                260                 265                 270

Tyr Ile Tyr Asn Leu Thr Glu Pro Pro Glu Cys Asn Leu Ala Tyr Cys
            275                 280                 285

Thr Asp Pro Ser Ser Val Glu Gly Thr Cys Glu Glu Cys Arg Val Asp
        290                 295                 300

Glu Asp Cys Ile Ser Asp Asn Gly Arg Trp Arg Cys Gln Cys Lys Gln
305                 310                 315                 320

Asp Ser Asn Ile Thr Asp Val Ser Gln Leu Glu Tyr Arg Leu Glu Cys
                325                 330                 335

Gly Ala Asn Asp Ile Lys Met Ser Leu Arg Lys Cys Gln Leu Gln Ser
            340                 345                 350

Leu Gly Phe Met Asn Val Phe Met Tyr Leu Asn Asp Arg Gln Cys Ser
        355                 360                 365

Gly Phe Ser Glu Ser Asp Glu Arg Asp Trp Met Ser Ile Val Thr Pro
    370                 375                 380

Ala Arg Asn Gly Pro Cys Gly Thr Val Leu Arg Arg Asn Glu Thr His
385                 390                 395                 400

Ala Thr Tyr Ser Asn Thr Leu Tyr Leu Ala Asn Ala Ile Ile Ile Arg
```

```
                    405                 410                 415
Asp Ile Ile Ile Arg Met Asn Phe Glu Cys Ser Tyr Pro Leu Asp Met
                420                 425                 430
Lys Val Ser Leu Lys Thr Ser Leu Gln Pro Met Val Ser Ala Leu Asn
            435                 440                 445
Ile Ser Leu Gly Gly Thr Gly Lys Phe Thr Val Arg Met Ala Leu Phe
        450                 455                 460
Gln Ser Pro Thr Tyr Thr Gln Pro Tyr Gln Gly Pro Ser Val Met Leu
465                 470                 475                 480
Ser Thr Glu Ala Phe Leu Tyr Val Gly Thr Met Leu Asp Gly Gly Asp
                485                 490                 495
Leu Ser Arg Phe Val Leu Leu Met Thr Asn Cys Tyr Ala Thr Pro Ser
            500                 505                 510
Ser Asn Ser Thr Asp Pro Val Lys Tyr Phe Ile Ile Gln Asp Ser Cys
        515                 520                 525
Pro Arg Thr Glu Asp Thr Thr Ile Gln Val Thr Glu Asn Gly Glu Ser
    530                 535                 540
Ser Gln Ala Arg Phe Ser Val Gln Met Phe Arg Phe Ala Gly Asn Tyr
545                 550                 555                 560
Asp Leu Val Tyr Leu His Cys Glu Val Tyr Leu Cys Asp Ser Thr Ser
                565                 570                 575
Glu Gln Cys Lys Pro Thr Cys Ser Gly Thr Arg Phe Arg Cys Gly Asn
            580                 585                 590
Phe Ile Asp Gln Thr Arg Val Leu Asn Leu Gly Pro Ile Thr Arg Gln
        595                 600                 605
Gly Val Gln Ala Ser Val Ser Lys Ala Ala Ser Ser Asn Leu Arg Leu
    610                 615                 620
Leu Ser Ile Trp Leu Leu Phe Leu Ser Ala Thr Leu Ile Phe Met
625                 630                 635                 640
Val Gln

<210> SEQ ID NO 40
<211> LENGTH: 640
<212> TYPE: PRT
<213> ORGANISM: Human Uromodulin

<400> SEQUENCE: 40

Met Gly Gln Pro Ser Leu Thr Trp Met Leu Met Val Val Val Ala Ser
1               5                   10                  15
Trp Phe Ile Thr Thr Ala Ala Thr Asp Thr Ser Glu Ala Arg Trp Cys
                20                  25                  30
Ser Glu Cys His Ser Asn Ala Thr Cys Thr Glu Asp Glu Ala Val Thr
            35                  40                  45
Thr Cys Thr Cys Gln Glu Gly Phe Thr Gly Asp Gly Leu Thr Cys Val
        50                  55                  60
Asp Leu Asp Glu Cys Ala Ile Pro Gly Ala His Asn Cys Ser Ala Asn
65                  70                  75                  80
Ser Ser Cys Val Asn Thr Pro Gly Ser Phe Ser Cys Val Cys Pro Glu
                85                  90                  95
Gly Phe Arg Leu Ser Pro Gly Leu Gly Cys Thr Asp Val Asp Glu Cys
            100                 105                 110
Ala Glu Pro Gly Leu Ser His Cys His Ala Leu Ala Thr Cys Val Asn
        115                 120                 125
Val Val Gly Ser Tyr Leu Cys Val Cys Pro Ala Gly Tyr Arg Gly Asp
```

```
            130                 135                 140
Gly Trp His Cys Glu Cys Ser Pro Gly Ser Cys Pro Gly Leu Asp
145                 150                 155                 160

Cys Val Pro Glu Gly Asp Ala Leu Val Cys Ala Asp Pro Cys Gln Ala
                165                 170                 175

His Arg Thr Leu Asp Glu Tyr Trp Arg Ser Thr Glu Tyr Gly Glu Gly
                180                 185                 190

Tyr Ala Cys Asp Thr Asp Leu Arg Gly Trp Tyr Arg Phe Val Gly Gln
                195                 200                 205

Gly Gly Ala Arg Met Ala Glu Thr Cys Val Pro Val Leu Arg Cys Asn
210                 215                 220

Thr Ala Ala Pro Met Trp Leu Asn Gly Thr His Pro Ser Ser Asp Glu
225                 230                 235                 240

Gly Ile Val Ser Arg Lys Ala Cys Ala His Trp Ser Gly His Cys Cys
                245                 250                 255

Leu Trp Asp Ala Ser Val Gln Val Lys Ala Cys Ala Gly Tyr Tyr
                260                 265                 270

Val Tyr Asn Leu Thr Ala Pro Pro Glu Cys His Leu Ala Tyr Cys Thr
    275                 280                 285

Asp Pro Ser Ser Val Glu Gly Thr Cys Glu Glu Cys Ser Ile Asp Glu
    290                 295                 300

Asp Cys Lys Ser Asn Asn Gly Arg Trp His Cys Gln Cys Lys Gln Asp
305                 310                 315                 320

Phe Asn Ile Thr Asp Ile Ser Leu Leu Glu His Arg Leu Glu Cys Gly
                325                 330                 335

Ala Asn Asp Met Lys Val Ser Leu Gly Lys Cys Gln Leu Lys Ser Leu
                340                 345                 350

Gly Phe Asp Lys Val Phe Met Tyr Leu Ser Asp Ser Arg Cys Ser Gly
                355                 360                 365

Phe Asn Asp Arg Asp Asn Arg Asp Trp Val Ser Val Thr Pro Ala
    370                 375                 380

Arg Asp Gly Pro Cys Gly Thr Val Leu Thr Arg Asn Glu Thr His Ala
385                 390                 395                 400

Thr Tyr Ser Asn Thr Leu Tyr Leu Ala Asp Glu Ile Ile Arg Asp
                405                 410                 415

Leu Asn Ile Lys Ile Asn Phe Ala Cys Ser Tyr Pro Leu Asp Met Lys
                420                 425                 430

Val Ser Leu Lys Thr Ala Leu Gln Pro Met Val Ser Ala Leu Asn Ile
                435                 440                 445

Arg Val Gly Gly Thr Gly Met Phe Thr Val Arg Met Ala Leu Phe Gln
    450                 455                 460

Thr Pro Ser Tyr Thr Gln Pro Tyr Gln Gly Ser Ser Val Thr Leu Ser
465                 470                 475                 480

Thr Glu Ala Phe Leu Tyr Val Gly Thr Met Leu Asp Gly Gly Asp Leu
                485                 490                 495

Ser Arg Phe Ala Leu Leu Met Thr Asn Cys Tyr Ala Thr Pro Ser Ser
                500                 505                 510

Asn Ala Thr Asp Pro Leu Lys Tyr Phe Ile Ile Gln Asp Arg Cys Pro
                515                 520                 525

His Thr Arg Asp Ser Thr Ile Gln Val Val Glu Asn Gly Glu Ser Ser
    530                 535                 540

Gln Gly Arg Phe Ser Val Gln Met Phe Arg Phe Ala Gly Asn Tyr Asp
545                 550                 555                 560
```

-continued

Leu Val Tyr Leu His Cys Glu Val Tyr Leu Cys Asp Thr Met Asn Glu
            565                 570                 575

Lys Cys Lys Pro Thr Cys Ser Gly Thr Arg Phe Arg Ser Gly Ser Val
            580                 585                 590

Ile Asp Gln Ser Arg Val Leu Asn Leu Gly Pro Ile Thr Arg Lys Gly
            595                 600                 605

Val Gln Ala Thr Val Ser Arg Ala Phe Ser Ser Leu Gly Leu Leu Lys
            610                 615                 620

Val Trp Leu Pro Leu Leu Leu Ser Ala Thr Leu Thr Leu Thr Phe Gln
625                 630                 635                 640

<210> SEQ ID NO 41
<211> LENGTH: 459
<212> TYPE: PRT
<213> ORGANISM: Bovine Uromodulin

<400> SEQUENCE: 41

Met Lys Cys Ser Asn Met Trp Met Ala Ala Val Val Thr Ser Trp Val
1               5                   10                  15

Ala Ala Thr Asp Thr Ser Ser Ala Lys Ser Cys Ser Cys His Ser Asn
            20                  25                  30

Ala Thr Cys Thr Val Asp Gly Ala Ala Thr Thr Cys Ala Cys Gly Thr
            35                  40                  45

Gly Asp Gly Cys Val Asp Cys Ala Val Gly Ala His Asn Cys Ser
        50                  55                  60

Ala Thr Lys Ser Cys Val Asn Thr Gly Ser Tyr Thr Cys Val Cys Gly
65                  70                  75                  80

Ser Ser Gly Cys Asp Val Asp Cys Ala Gly Ser Arg Cys His Ala Ala
            85                  90                  95

Thr Cys Asn Gly Gly Asn Tyr Ser Cys Val Cys Ala Gly Tyr Gly Asp
            100                 105                 110

Gly Arg His Cys Cys Ser Gly Ser Cys Gly Gly Asp Cys Val Arg Gly
            115                 120                 125

Asp Ala Val Cys Val Asp Cys Val His Arg Asp Tyr Trp Arg Ser Thr
130                 135                 140

Tyr Gly Ser Gly Tyr Cys Asp Val Ser Gly Gly Trp Tyr Arg Val Gly
145                 150                 155                 160

Ala Gly Val Arg Thr Cys Val Val His Cys Asn Thr Ala Ala Met Trp
            165                 170                 175

Asn Gly Thr His Ser Ser Asp Gly Val Asn Arg Val Ala Cys Ala His
            180                 185                 190

Trp Ser Gly Asp Cys Cys Trp Asp Ala Val Lys Ala Cys Ala Gly Gly
            195                 200                 205

Tyr Tyr Val Tyr Asn Thr Ala Cys His Ala Tyr Cys Thr Asp Ser Ser
            210                 215                 220

Val Gly Thr Cys Cys Arg Val Asp Asp Cys Lys Ser Asp Asn Gly Trp
225                 230                 235                 240

His Cys Cys Lys Asp Asn Val Thr Asp Ser Arg Arg Cys Gly Val Asp
            245                 250                 255

Asp Lys Ser Ser Lys Cys Lys Ser Gly Lys Val Met Tyr His Asp Ser
            260                 265                 270

Cys Ser Gly Thr Arg Gly Asp Arg Asp Trp Met Ser Val Val Thr Ala
            275                 280                 285

Arg Asp Gly Cys Gly Thr Val Met Thr Arg Asn Thr His Ala Thr Tyr

-continued

```
                    290                 295                 300
Ser Asn Thr Tyr Ala Asp Arg Asp Asn Arg Asn Ala Cys Ser Tyr Asp
305                 310                 315                 320

Met Lys Val Ser Lys Thr Ser Met Val Ser Ala Asn Ser Met Gly Gly
                325                 330                 335

Thr Gly Thr Thr Val Arg Met Ala Ser Ala Tyr Thr Tyr Gly Ser Ser
            340                 345                 350

Val Thr Ser Thr Ala Tyr Val Gly Thr Met Asp Gly Gly Asp Ser Arg
        355                 360                 365

Val Met Thr Asn Cys Tyr Ala Thr Ser Ser Asn Ala Thr Asp Lys Tyr
    370                 375                 380

Asp Arg Cys Arg Ala Ala Asp Ser Thr Val Asn Gly Ser Gly Arg Ser
385                 390                 395                 400

Val Met Arg Ala Gly Asn Tyr Asp Val Tyr His Cys Val Tyr Cys Asp
                405                 410                 415

Thr Val Asn Lys Cys Arg Thr Cys Thr Arg Arg Ser Gly Ser Asp Thr
            420                 425                 430

Arg Val Asn Gly Thr Arg Lys Gly Gly Ala Ala Met Ser Arg Ala Ala
        435                 440                 445

Ser Ser Gly Val Trp Ser Ala Thr Thr Met Ser
    450                 455

<210> SEQ ID NO 42
<211> LENGTH: 34
<212> TYPE: PRT
<213> ORGANISM: Rat Uromodulin

<400> SEQUENCE: 42

Gly Val Gln Ala Ser Val Ser Lys Ala Ala Ser Ser Asn Leu Gly Phe
1               5                   10                  15

Leu Ser Ile Trp Leu Leu Leu Phe Leu Ser Ala Thr Leu Thr Leu Met
            20                  25                  30

Val His

<210> SEQ ID NO 43
<211> LENGTH: 34
<212> TYPE: PRT
<213> ORGANISM: Mouse Uromodulin

<400> SEQUENCE: 43

Gly Val Gln Ala Ser Val Ser Lys Ala Ala Ser Ser Asn Leu Arg Leu
1               5                   10                  15

Leu Ser Ile Trp Leu Leu Leu Phe Leu Ser Ala Thr Leu Ile Phe Met
            20                  25                  30

Val Gln

<210> SEQ ID NO 44
<211> LENGTH: 33
<212> TYPE: PRT
<213> ORGANISM: Human Uromodulin

<400> SEQUENCE: 44

Gly Val Gln Ala Thr Val Ser Arg Ala Phe Ser Ser Leu Gly Leu Leu
1               5                   10                  15

Lys Val Trp Leu Pro Leu Leu Leu Ser Ala Thr Leu Thr Leu Thr Phe
            20                  25                  30

Gln
```

<210> SEQ ID NO 45
<211> LENGTH: 34
<212> TYPE: PRT
<213> ORGANISM: Bovine Uromodulin

<400> SEQUENCE: 45

Gly Gly Gln Ala Ala Met Ser Arg Ala Ala Pro Ser Ser Leu Gly Leu
1               5                   10                  15

Leu Gln Val Trp Leu Pro Leu Leu Ser Ala Thr Leu Thr Leu Met
            20                  25                  30

Ser Pro

<210> SEQ ID NO 46
<211> LENGTH: 42
<212> TYPE: PRT
<213> ORGANISM: Torpedo

<400> SEQUENCE: 46

Asn Gln Phe Leu Pro Lys Leu Leu Asn Ala Thr Ala Cys Asp Gly Glu
1               5                   10                  15

Leu Ser Ser Ser Gly Thr Ser Ser Ser Lys Gly Ile Ile Phe Tyr Val
            20                  25                  30

Leu Phe Ser Ile Leu Tyr Leu Ile Phe Tyr
            35                  40

<210> SEQ ID NO 47
<211> LENGTH: 42
<212> TYPE: PRT
<213> ORGANISM: Placenta

<400> SEQUENCE: 47

Thr Ala Cys Asp Leu Ala Pro Pro Ala Gly Thr Thr Asp Ala Ala His
1               5                   10                  15

Pro Gly Arg Ser Val Val Pro Ala Leu Leu Pro Leu Leu Ala Gly Thr
            20                  25                  30

Leu Leu Leu Leu Glu Thr Ala Thr Ala Pro
            35                  40

<210> SEQ ID NO 48
<211> LENGTH: 41
<212> TYPE: PRT
<213> ORGANISM: Decay Accelerating Factor

<400> SEQUENCE: 48

His Glu Thr Thr Pro Asn Lys Gly Ser Gly Thr Thr Ser Gly Thr Thr
1               5                   10                  15

Arg Leu Leu Ser Gly His Thr Cys Phe Thr Leu Thr Gly Leu Leu Gly
            20                  25                  30

Thr Leu Val Thr Met Gly Leu Leu Thr
            35                  40

<210> SEQ ID NO 49
<211> LENGTH: 35
<212> TYPE: PRT
<213> ORGANISM: T. Brucei

<400> SEQUENCE: 49

Glu Pro Glu Pro Glu Pro Glu Pro Glu Pro Glu Pro Gly Ala Ala Thr
1               5                   10                  15

-continued

Leu Lys Ser Val Ala Leu Pro Phe Ala Ile Ala Ala Ala Leu Val
            20                  25                  30

Ala Ala Phe
        35

<210> SEQ ID NO 50
<211> LENGTH: 36
<212> TYPE: PRT
<213> ORGANISM: Hamster

<400> SEQUENCE: 50

Gln Lys Glu Ser Gln Ala Tyr Tyr Asp Gly Arg Arg Ser Ser Ala Val
1               5                   10                  15

Leu Phe Ser Ser Pro Pro Val Ile Leu Leu Ile Ser Phe Leu Ile Phe
            20                  25                  30

Leu Met Val Gly
        35

<210> SEQ ID NO 51
<211> LENGTH: 44
<212> TYPE: PRT
<213> ORGANISM: Rat

<400> SEQUENCE: 51

Lys Thr Ile Asn Val Ile Arg Asp Lys Leu Val Lys Cys Gly Gly Ile
1               5                   10                  15

Ser Leu Leu Val Gln Asn Thr Ser Trp Leu Leu Leu Leu Leu Leu Ser
            20                  25                  30

Leu Ser Phe Leu Gln Ala Thr Asp Phe Ile Ser Leu
        35                  40

<210> SEQ ID NO 52
<211> LENGTH: 36
<212> TYPE: PRT
<213> ORGANISM: T. Brucei

<400> SEQUENCE: 52

Glu Ser Asn Cys Lys Trp Glu Asn Asn Ala Cys Lys Asp Ser Ser Ile
1               5                   10                  15

Leu Val Thr Lys Lys Phe Ala Leu Thr Val Val Ser Ala Ala Phe Val
            20                  25                  30

Ala Leu Leu Phe
        35

<210> SEQ ID NO 53
<211> LENGTH: 29
<212> TYPE: DNA
<213> ORGANISM: Artificial Sequence
<220> FEATURE:
<223> OTHER INFORMATION: Synthetic

<400> SEQUENCE: 53
gaagggcccc caagagatcc aagtctcct                                       29

<210> SEQ ID NO 54
<211> LENGTH: 30
<212> TYPE: DNA
<213> ORGANISM: Artificial Sequence -continued
<220> FEATURE:
<223> OTHER INFORMATION: Synthetic

<400> SEQUENCE: 54
gaagggccct cacaagtaag tgcctgtgat                                    30